United States Patent
Jung et al.

(10) Patent No.: US 12,022,730 B2
(45) Date of Patent: Jun. 25, 2024

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR);
(Continued)

(73) Assignee: LG Chem, Ltd., Seoul (KR)

( * ) Notice: Subject to any disclaimer, the term of this patent is extended or adjusted under 35 U.S.C. 154(b) by 329 days.

(21) Appl. No.: 17/278,757

(22) PCT Filed: Nov. 27, 2019

(86) PCT No.: PCT/KR2019/016488
§ 371 (c)(1),
(2) Date: Mar. 23, 2021

(87) PCT Pub. No.: WO2020/111780
PCT Pub. Date: Jun. 4, 2020

(65) Prior Publication Data
US 2022/0037593 A1 Feb. 3, 2022

(30) Foreign Application Priority Data

Nov. 27, 2018 (KR) .......... 10-2018-0148563
Nov. 26, 2019 (KR) .......... 10-2019-0153522

(51) Int. Cl.
*H10K 85/60* (2023.01)
*C07D 401/14* (2006.01)
(Continued)

(52) U.S. Cl.
CPC ......... *H10K 85/654* (2023.02); *C07D 401/14* (2013.01); *C07D 403/14* (2013.01); *H10K 85/6572* (2023.02); *H10K 50/11* (2023.02)

(58) Field of Classification Search
CPC .......... C07D 403/14; C07D 251/24; C07D 209/82; C07D 491/048; C07D 519/00; H10K 85/654; H10K 85/657; H10K 85/6572
See application file for complete search history.

(56) References Cited

U.S. PATENT DOCUMENTS 9,577,199 B2 * 2/2017 Lecloux .............. C07D 209/86
2004/0251816 A1 12/2004 Leo et al.
(Continued)

FOREIGN PATENT DOCUMENTS

CN 101087776 A 12/2007
CN 100366703 2/2008
(Continued)

OTHER PUBLICATIONS

Park, H. et al., "A directly coupled dual emitting core based molecular design of thermally activated delayed fluorescent emitters," J. Mater. Chem. C., 5:12143-12150 (2017).
(Continued)

*Primary Examiner* — Vu A Nguyen
(74) *Attorney, Agent, or Firm* — Bryan Cave Leighton Paisner LLP

(57) ABSTRACT

Provided is a compound of Chemical Formula 1:

Chemical Formula 1

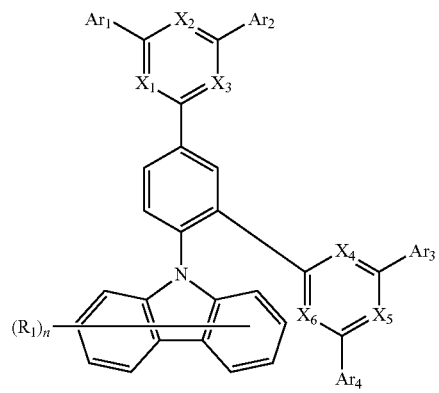

wherein, in Chemical Formula 1:
$X_1$ to $X_6$ are each independently CH or N, with the proviso that at least one of $X_1$ to $X_6$ is N;
(Continued)

Ar₁ to Ar₄ are each independently a substituted or unsubstituted $C_{6-60}$ aryl, with the proviso that at least one of Ar₁ to Ar₄ is a $C_{6-60}$ aryl containing deuterium as a substituent;

R₁ is hydrogen, deuterium, a substituted or unsubstituted $C_{6-60}$ aryl, or a substituted or unsubstituted $C_{2-60}$ heteroaryl containing one or more heteroatoms selected from the group consisting of N, O, and S; and n is an integer of 0 to 8, and an organic light emitting device including the using same.

4 Claims, 1 Drawing Sheet

(72) Inventors: Boon Jae Jang, Daejeon (KR); Wanpyo Hong, Daejeon (KR); Sang Duk Suh, Daejeon (KR); Jungha Lee, Daejeon (KR); Su Jin Han, Daejeon (KR); Seulchan Park, Daejeon (KR); Sunghyun Hwang, Daejeon (KR)

(51) Int. Cl.
C07D 403/14 (2006.01)
H10K 50/11 (2023.01)

(56) References Cited

U.S. PATENT DOCUMENTS

| | | |
|---|---|---|
| 2009/0191426 A2 | 7/2009 | Yabe et al. |
| 2010/0187505 A1 | 7/2010 | Stoessel et al. |
| 2012/0126221 A1 | 5/2012 | Kitamura et al. |
| 2012/0126692 A1 | 5/2012 | Ise et al. |
| 2012/0205640 A1 | 8/2012 | Kai et al. |
| 2013/0240796 A1 | 9/2013 | Parham et al. |
| 2013/0292654 A1 | 11/2013 | Matsunaga et al. |
| 2014/0114069 A1 | 4/2014 | Kim et al. |
| 2015/0218191 A1 | 8/2015 | Sannomiya et al. |
| 2015/0380662 A1 | 12/2015 | Kim et al. |
| 2016/0329502 A1 | 11/2016 | Dyatkin et al. |
| 2017/0047522 A1 | 2/2017 | Noda et al. |
| 2017/0117488 A1 | 4/2017 | Ahn et al. |
| 2017/0244043 A1 | 8/2017 | Kim et al. |
| 2018/0123049 A1 | 5/2018 | Lee et al. |
| 2018/0145262 A1 | 5/2018 | Zeng et al. |
| 2018/0170914 A1 | 6/2018 | Miyata et al. |
| 2018/0248127 A1 | 8/2018 | Lee et al. |
| 2019/0019960 A1* | 1/2019 | Zink ............ H10K 85/654 |
| 2019/0237680 A1 | 8/2019 | Kim et al. |
| 2019/0288222 A1 | 9/2019 | Moon et al. |
| 2020/0044163 A1 | 2/2020 | Hung et al. |
| 2020/0115364 A1 | 4/2020 | Aguilera-Iparraguirre et al. |
| 2020/0331898 A1 | 10/2020 | Seifermann |
| 2022/0271233 A1 | 8/2022 | Yoon et al. |

FOREIGN PATENT DOCUMENTS

| | | |
|---|---|---|
| CN | 103764786 | 4/2014 |
| CN | 107667102 | 2/2018 |
| CN | 107880028 | 4/2018 |
| CN | 107935914 | 4/2018 |
| CN | 107954922 | 4/2018 |
| CN | 107987009 | 5/2018 |
| CN | 109251199 A | 1/2019 |
| CN | 112533900 A | 3/2021 |
| DE | 102016112377 | 1/2018 |
| JP | 2009-155300 A | 7/2009 |
| JP | 2009-158848 A | 7/2009 |
| JP | 2010-030937 | 2/2010 |
| JP | 4474493 | 6/2010 |
| JP | 4590020 | 12/2010 |
| JP | 4729642 | 7/2011 |
| JP | 2014-141571 | 8/2014 |
| JP | 2018-035129 | 3/2018 |
| KR | 10-2000-0051826 | 8/2000 |
| KR | 10-2010-0131939 | 12/2010 |
| KR | 10-2012-0018231 | 2/2012 |
| KR | 10-2012-0033711 | 4/2012 |
| KR | 10-2012-0098694 | 9/2012 |
| KR | 10-2012-0109744 | 10/2012 |
| KR | 10-2013-0020398 | 2/2013 |
| KR | 10-2013-0130236 | 12/2013 |
| KR | 10-2014-0014959 | 2/2014 |
| KR | 10-2014-0015240 | 2/2014 |
| KR | 10-1396171 | 5/2014 |
| KR | 10-2014-0139307 | 12/2014 |
| KR | 10-2015-0061174 | 6/2015 |
| KR | 10-2015-0063462 | 6/2015 |
| KR | 10-2015-0105201 | 9/2015 |
| KR | 10-2015-0129282 A | 11/2015 |
| KR | 10-2015-0139459 | 12/2015 |
| KR | 10-2016-0003362 | 1/2016 |
| KR | 10-2016-0041768 | 4/2016 |
| KR | 10-2016-0066339 | 6/2016 |
| KR | 10-2016-0129190 | 11/2016 |
| KR | 10-2017-0049291 | 5/2017 |
| KR | 10-2017-0060836 | 6/2017 |
| KR | 10-2017-0076292 A | 7/2017 |
| KR | 10-2017-0079348 | 7/2017 |
| KR | 10-2017-0097820 | 8/2017 |
| KR | 10-2017-0113808 | 10/2017 |
| KR | 10-2017-0116993 | 10/2017 |
| KR | 10-2018-0027468 | 3/2018 |
| KR | 10-2018-0047306 | 5/2018 |
| KR | 10-2018-0063708 | 6/2018 |
| KR | 10-2018-0065276 | 6/2018 |
| KR | 10-2018-0092035 | 8/2018 |
| KR | 10-2018-0098809 | 9/2018 |
| KR | 10-2018-0109747 | 10/2018 |
| KR | 10-1926771 | 12/2018 |
| KR | 10-2019-0008129 | 1/2019 |
| KR | 10-2019-0108094 | 9/2019 |
| KR | 10-2020-0047418 | 5/2020 |
| KR | 10-2020-0063053 | 6/2020 |
| TW | 201912640 | 4/2019 |
| WO | 2003-012890 | 2/2003 |
| WO | 2003-012890 A3 | 8/2003 |
| WO | 2012-005362 | 1/2012 |
| WO | 2013-027906 | 2/2013 |
| WO | 2016-089080 | 6/2016 |
| WO | 2016-181846 | 11/2016 |
| WO | 2017-190885 | 11/2017 |
| WO | 2018/147638 A1 | 8/2018 |
| WO | 2018/237385 A1 | 12/2018 |
| WO | 2019-076844 | 4/2019 |
| WO | 2019/086297 A1 | 5/2019 |
| WO | 2019121112 | 6/2019 |

OTHER PUBLICATIONS

Chan Seok Oh et al., "Dihedral Angle Control of Blue Thermally Activated Delayed Fluorescent Emitters through Donor Substitution Position for Efficient Reverse Intersystem Crossing", ACS Appl. Mater. Interfaces 10: 35420-35429 (2018).

Lee, D. R. et al., "Bis(diphenyltriazine) as a new acceptor of efficient thermally activated delayed flourescent emitters," Dyes and Pigments (2018), doi: 10.1016/j.dyepig.2017.12.048, 32 pages.

Kang et al., "High-efficiency blue organic light-emitting Diodes using emissive carbazole-triazine-based donor-acceptor molecules with high reverse intersystem crossing rates," Organic Electronics 75 (2019), 105399, pp. 1-7.

(56) References Cited

OTHER PUBLICATIONS

Braveeth et al., "Triazine-Acceptor-Based Green Thermally Activated Delayed Fluorescence Materials for Organic Light-Emitting Diodes," Materials (2019) 12, 2646 (doi:10.3390/ma12162646), pp. 1-19.

* cited by examiner

[FIG. 1]
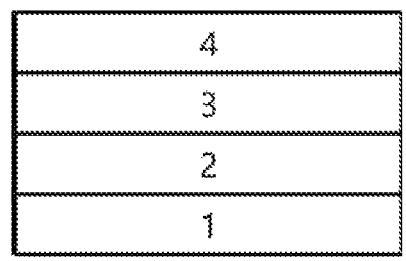
[FIG. 2]
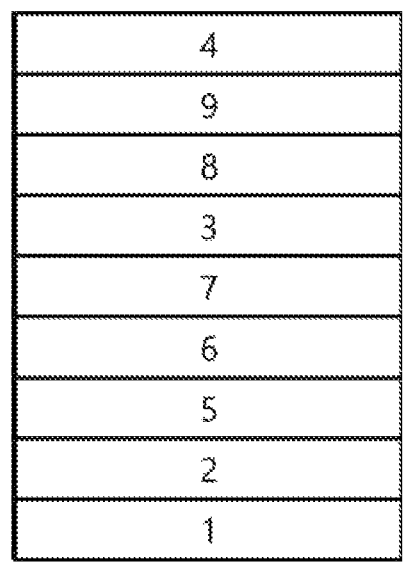

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/016488 filed on Nov. 27, 2019, which claims priority to or the benefit of Korean Patent Application No. 10-2018-0148563 filed with the Korean Intellectual Property Office on Nov. 27, 2018, and Korean Patent Application No. 10-2019-0153522 filed with the Korean Intellectual Property Office on Nov. 26, 2019, the disclosures of which are incorporated herein by reference in their entirety.

TECHNICAL FIELD

The present disclosure relates to a novel compound and an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 1) Korean Unexamined Patent Publication No. 10-2000-0051826

BRIEF DESCRIPTION

Technical Problem

It is an object of the present disclosure to provide a novel organic light emitting material and an organic light emitting device including the same.

Technical Solution

In one aspect of the present disclosure, provided is a compound of Chemical Formula 1:

Chemical Formula 1

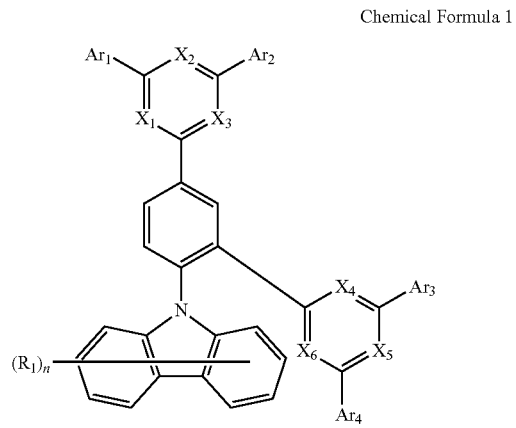

wherein, in Chemical Formula 1:
$X_1$ to $X_6$ are each independently CH or N, with the proviso that at least one of $X_1$ to $X_6$ is N;
$Ar_1$ to $Ar_4$ are each independently a substituted or unsubstituted $C_{6-60}$ aryl, with the proviso that at least one of $Ar_1$ to $Ar_4$ is a $C_{6-60}$ aryl containing deuterium as a substituent;
$R_1$ is hydrogen, deuterium, a substituted or unsubstituted $C_{6-60}$ aryl, or a substituted or unsubstituted $C_{2-60}$ heteroaryl containing one or more heteroatoms selected from the group consisting of N, O and S; and
n is an integer of 0 to 8.

In another aspect of the present disclosure, there is provided an organic light emitting device including a first electrode; a second electrode provided opposite to the first electrode; and one or more organic material layers provided between the first electrode and the second electrode, wherein one or more layers of the organic material layers include the compound of Chemical Formula 1.

Advantageous Effects

The compound of Chemical Formula 1 described above can be used as a material of an organic material layer of an organic light emitting device and can improve the efficiency, achieve low driving voltage and/or improve lifetime characteristics in the organic light emitting device. In particular, the compound of Chemical Formula 1 can be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, an electron blocking layer 7, a light emitting layer 3, an electron transport layer 8, an electron injection layer 9, and a cathode 4.

DETAILED DESCRIPTION

Hereinafter, embodiments of the present disclosure will be described in more detail to facilitate understanding of the invention.

One embodiment of the invention provides a compound of Chemical Formula 1.

As used herein, the notation ┊ or

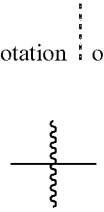

means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae but is not limited thereto:

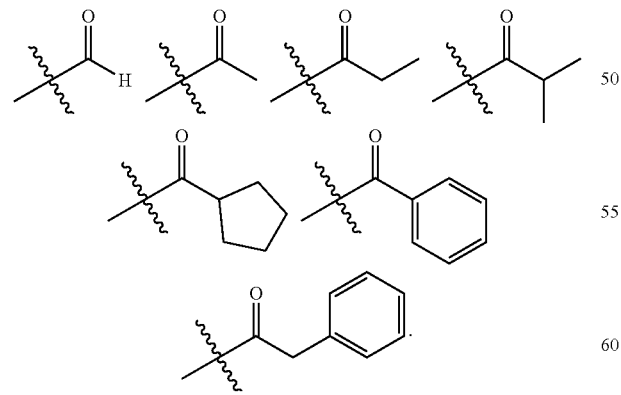

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

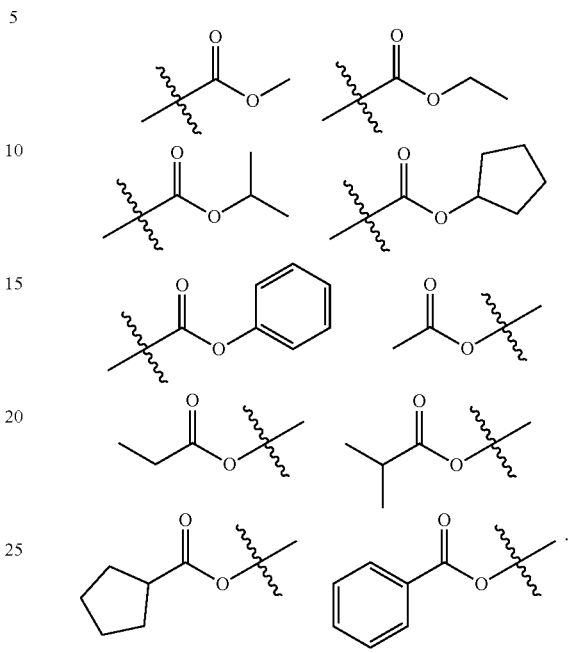

In the present specification, the number of carbon atoms of an imide group is not particularly limited, but is preferably 1 to 25. Specifically, the imide group can be a compound having the following structural formulae, but is not limited thereto:

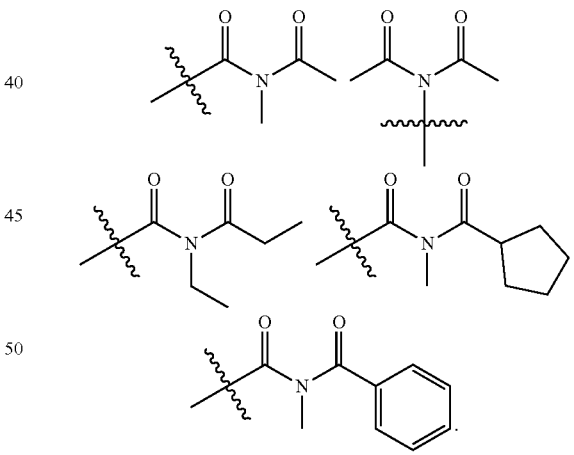

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be connected with each other to form a spiro structure. In the case where the fluorenyl group is substituted,

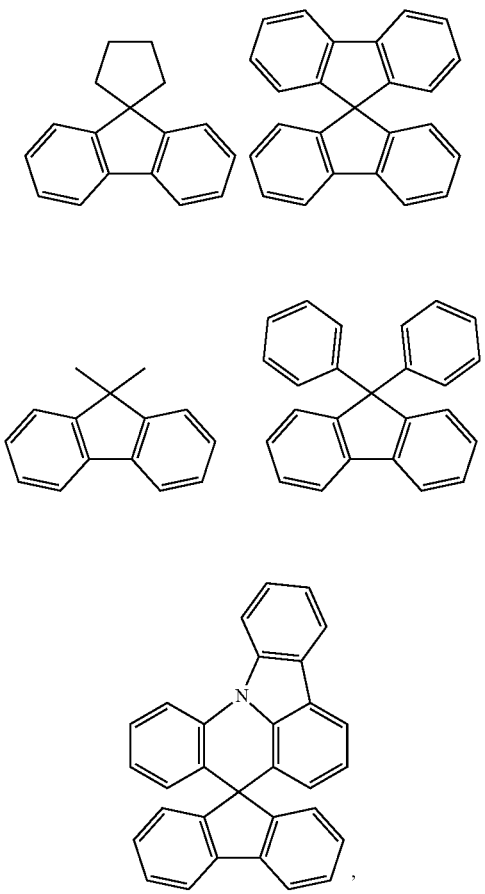

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazol group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an thiazolyl group, an isoxazolyl group, an oxadiazolyl group, an thiadiazolyl group, a benzothiazinyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Preferably, $X_1$ to $X_6$ can each independently be CH or N, with the proviso that at least one of $X_1$ to $X_3$ is N and at least one of $X_4$ to $X_6$ is N.

Preferably, $X_4$ to $X_6$ are each N.

More preferably, $X_1$ to $X_3$ can each independently be CH or N, with the proviso that at least one of $X_1$ to $X_3$ is N, and $X_4$ to $X_6$ can each be N.

Preferably, $Ar_1$ to $Ar_4$ can be each independently a substituted or unsubstituted $C_{6-20}$ aryl, with the proviso that at least one of $Ar_1$ to $Ar_4$ is a $C_{6-20}$ aryl containing deuterium as a substituent.

More preferably, $Ar_1$ to $Ar_4$ can be each independently a substituted or unsubstituted $C_{6-20}$ aryl, with the proviso that at least one of $Ar_1$ to $Ar_4$ is a phenyl substituted with five deuteriums.

Most preferably, $Ar_1$ to $Ar_4$ can be each independently a phenyl, biphenylyl, or phenyl substituted with five deuteriums, with the proviso that at least one of $Ar_1$ to $Ar_4$ is a phenyl substituted with five deuteriums.

Preferably, $R_1$ can be hydrogen, deuterium, a substituted or unsubstituted $C_{6-20}$ aryl, or a substituted or unsubstituted $C_{2-20}$ heteroaryl containing one or more heteroatoms selected from the group consisting of N, O and S.

More preferably, $R_1$ can be hydrogen or phenyl.

Preferably, n can be an integer of 0 to 2.

Preferably, Chemical Formula 1 can be any one of the following Chemical Formulae 1-1 to 1-7:

Chemical Formula 1-1

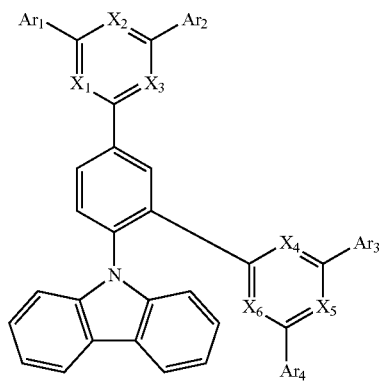

Chemical Formula 1-2

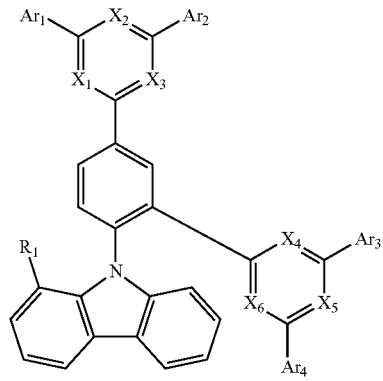

Chemical Formula 1-3

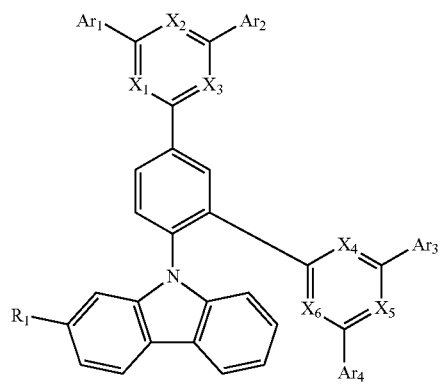

Chemical Formula 1-4

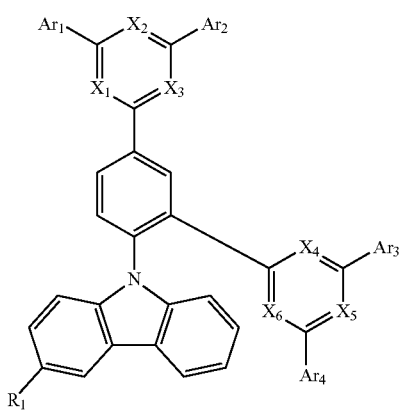

Chemical Formula 1-5
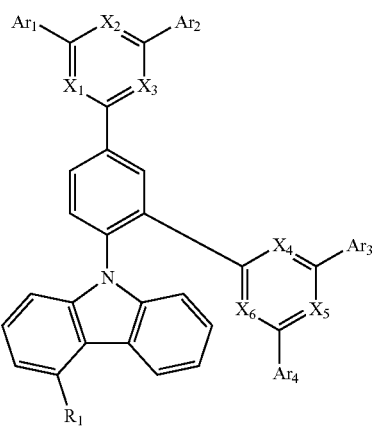
Representative examples of the compound of Chemical Formula 1 are as follows:
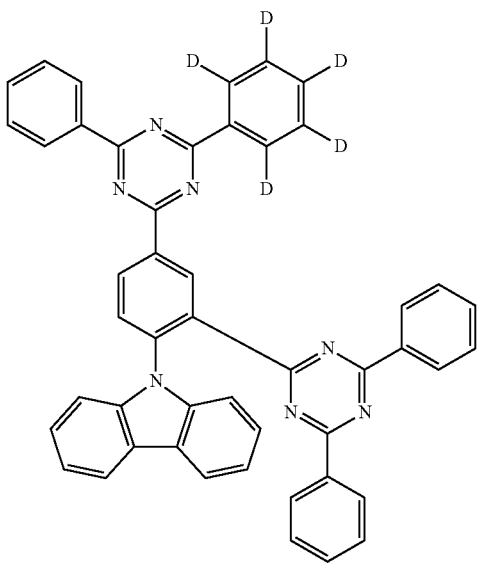
Chemical Formula 1-6
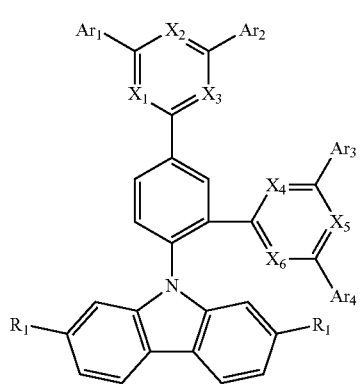
Chemical Formula 1-7
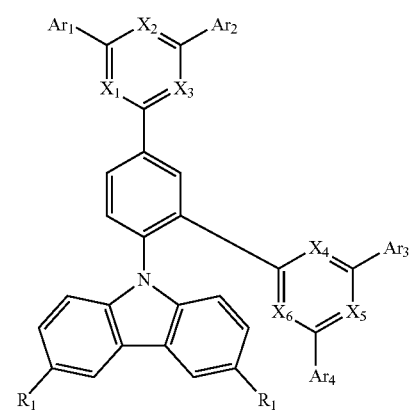
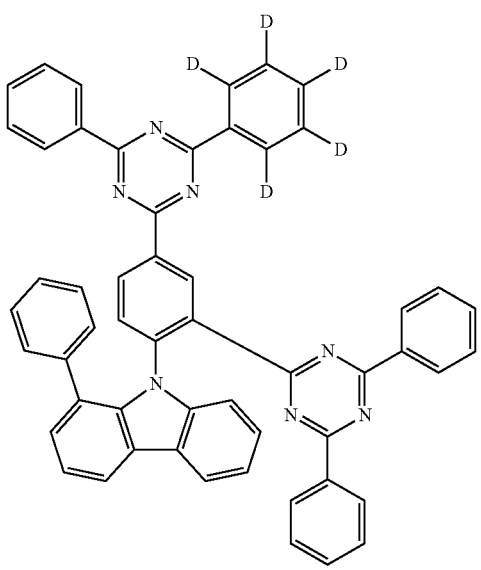
wherein, in Chemical Formulas 1-1 to 1-7:
$X_1$ to $X_6$, $Ar_1$ to $Ar_4$ and $R_1$ are the same as those defined in Chemical Formula 1.

11
-continued
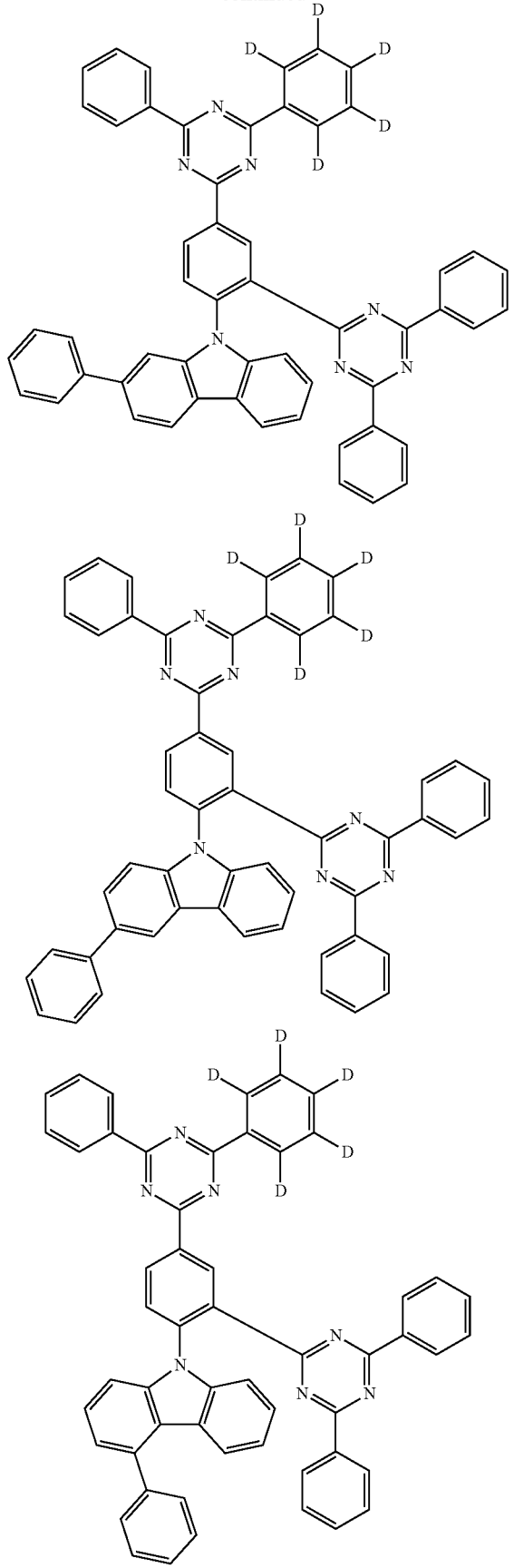
12
-continued
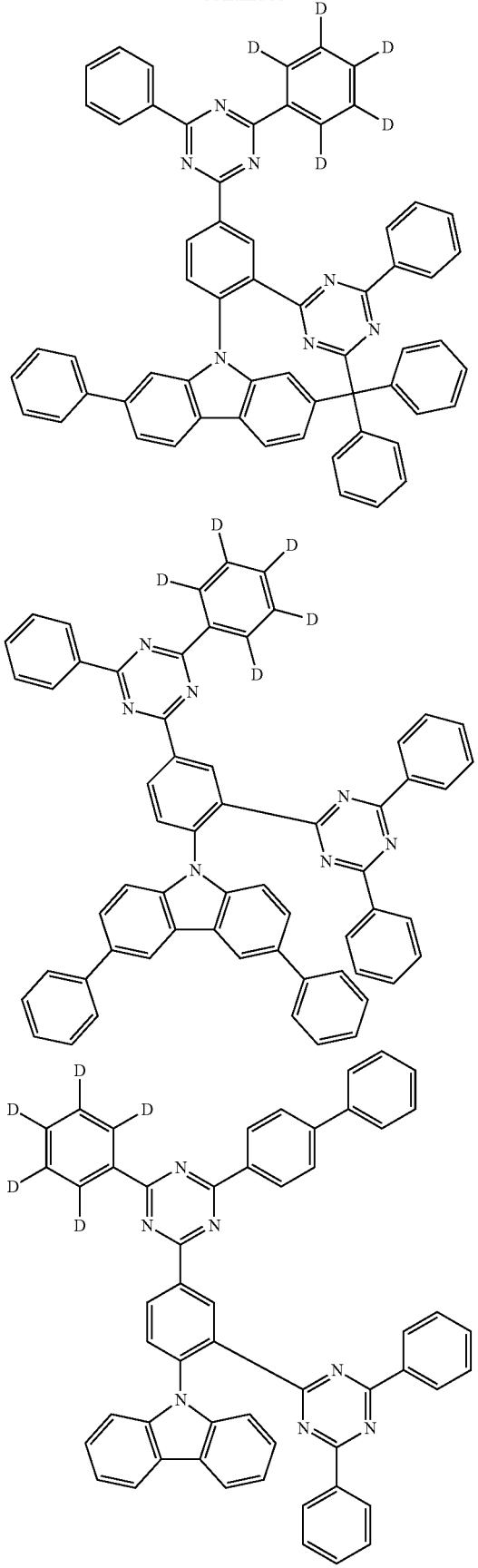

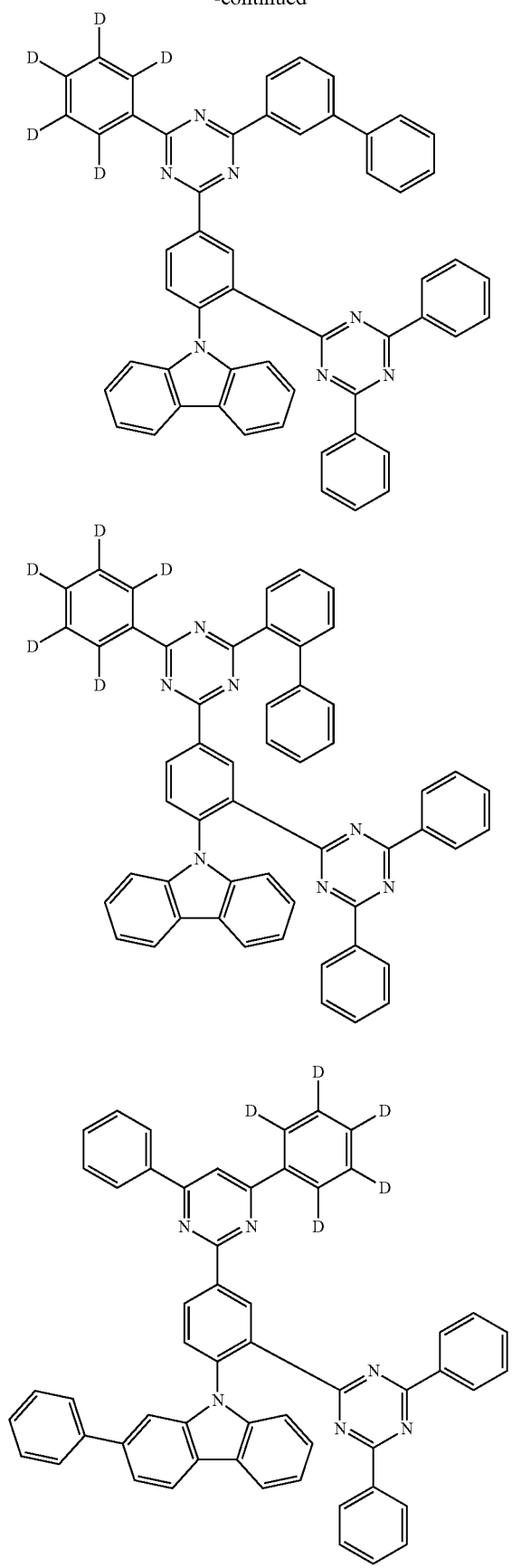
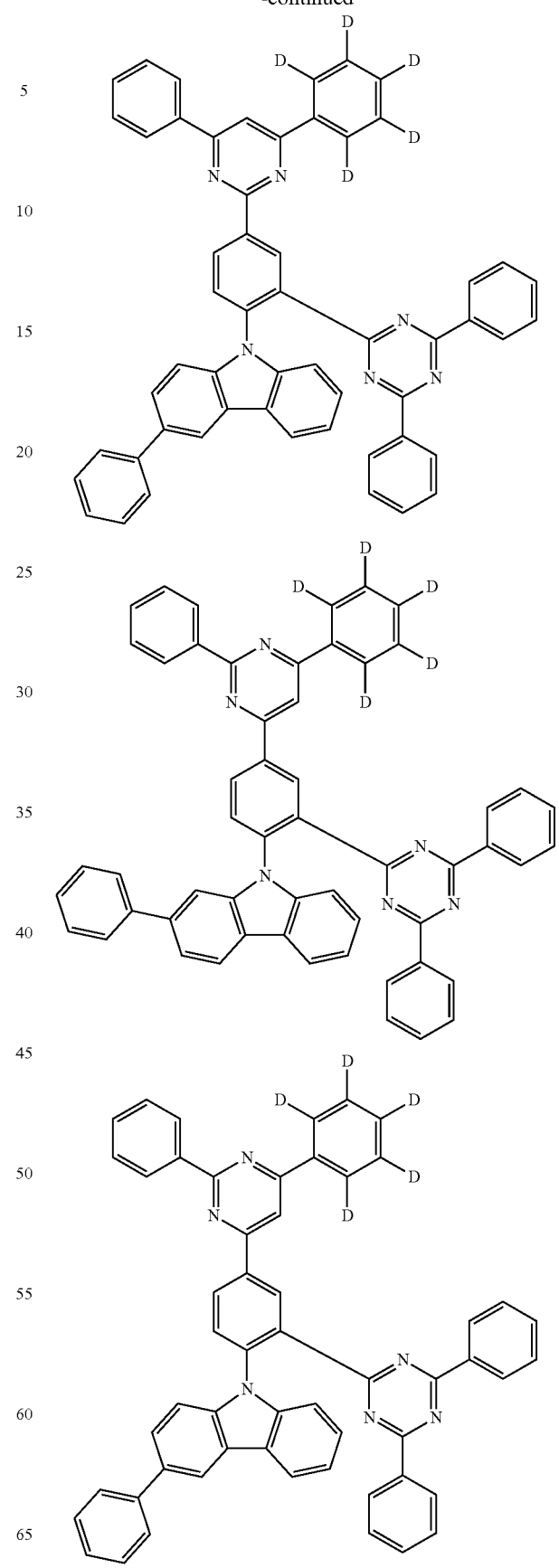

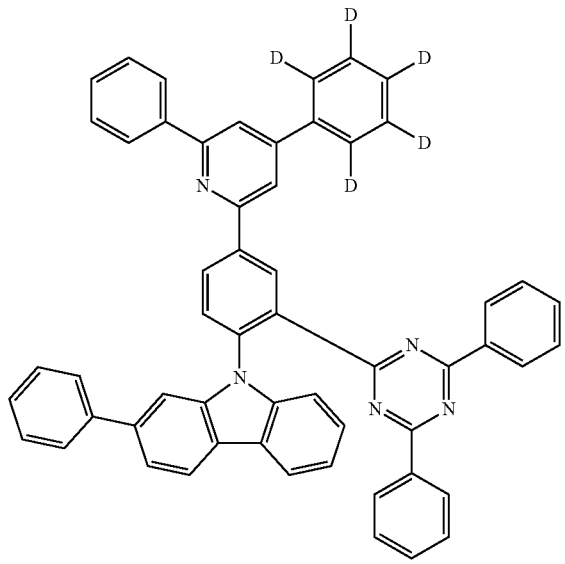
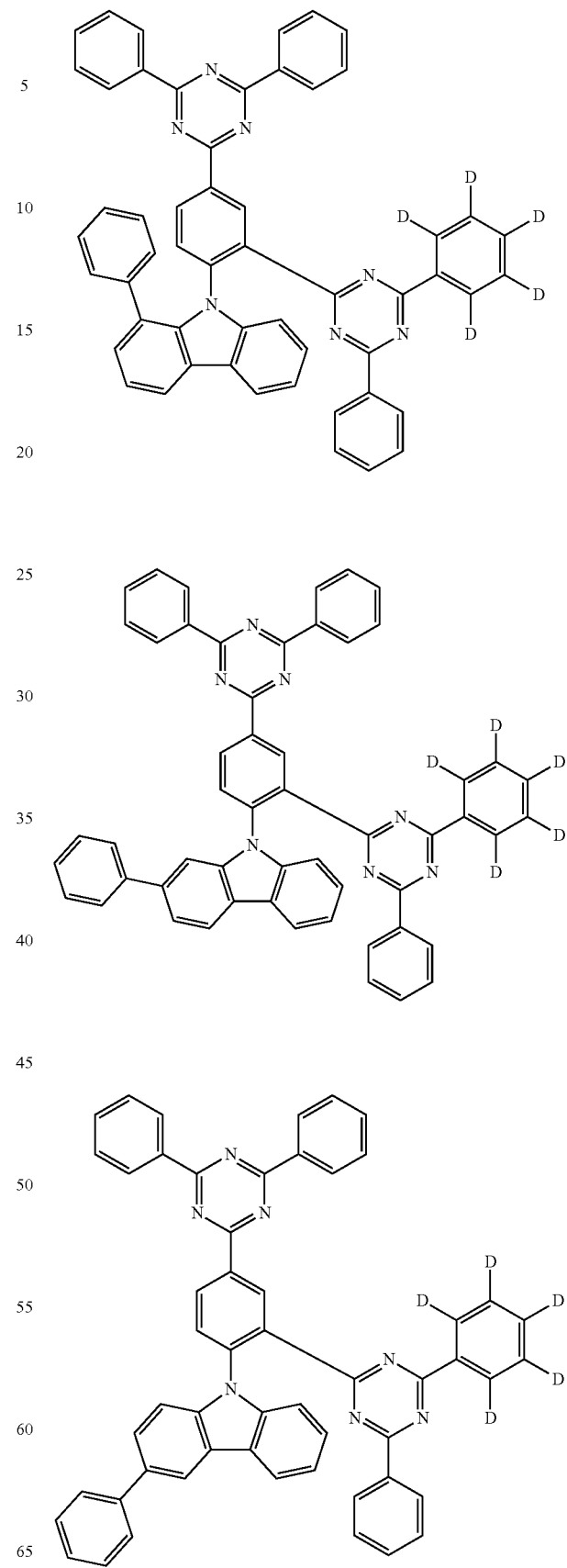

-continued
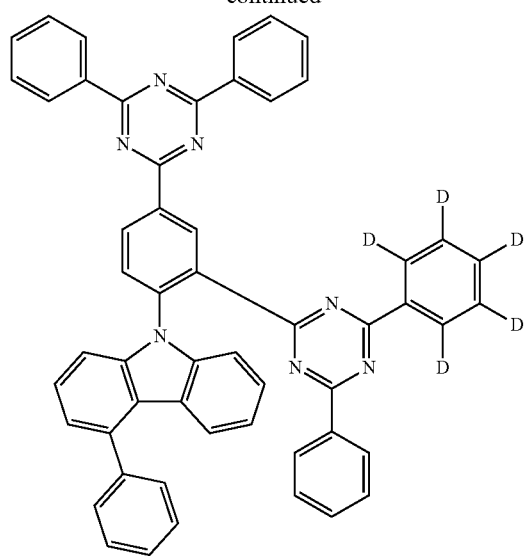
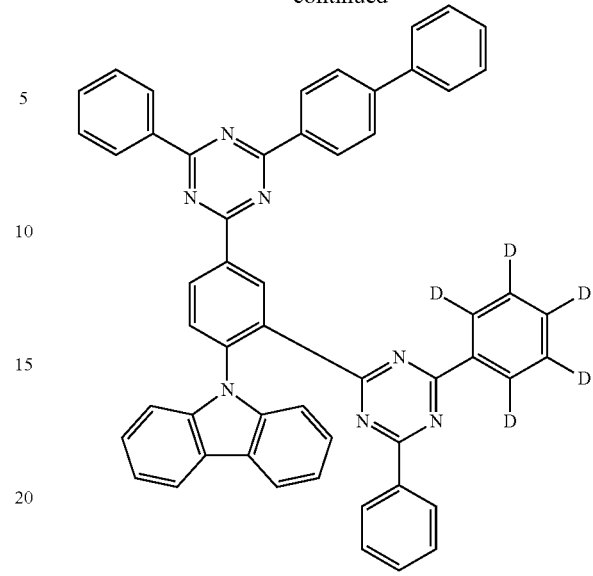
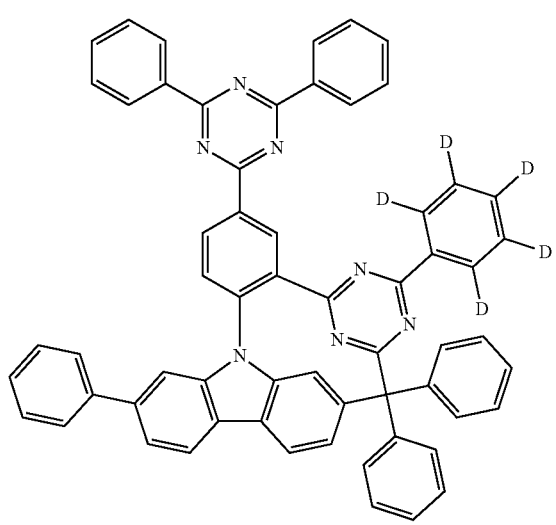
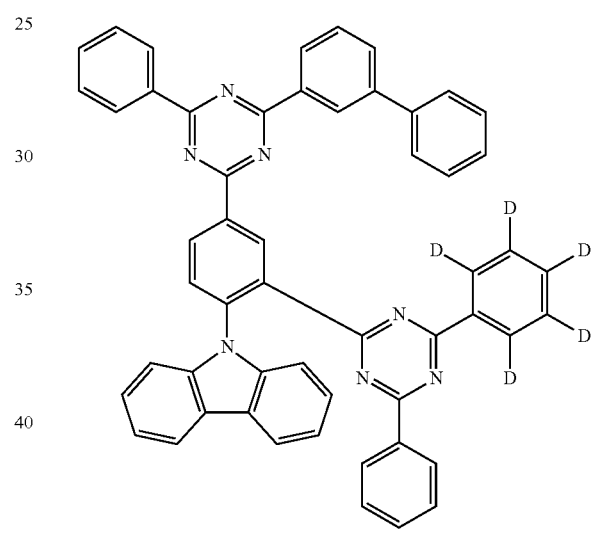
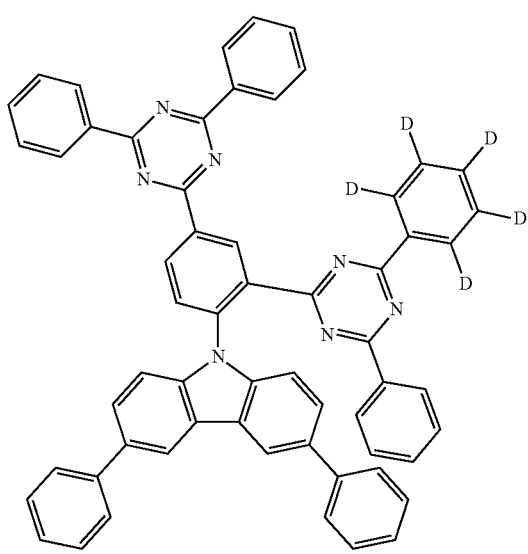
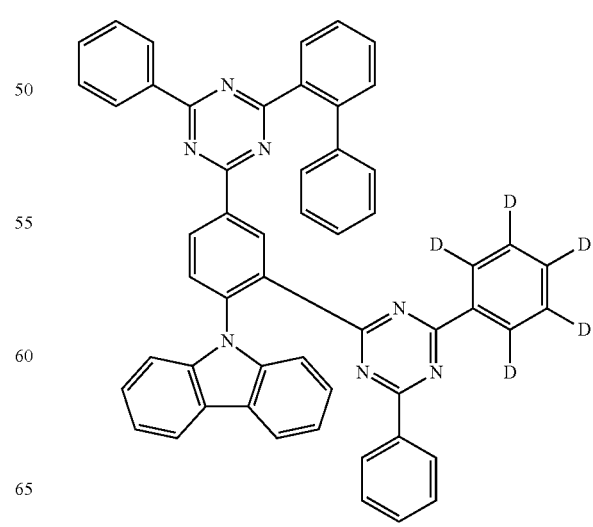

-continued
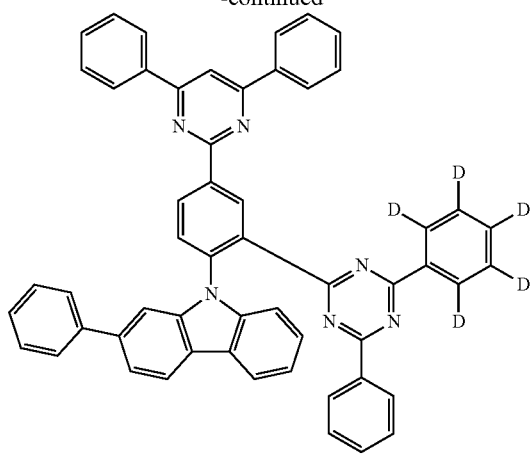
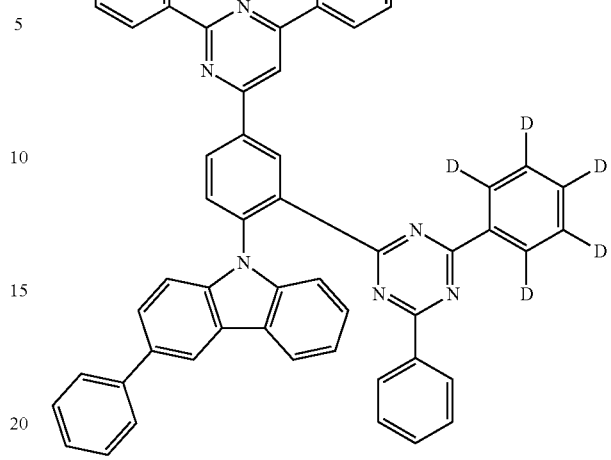
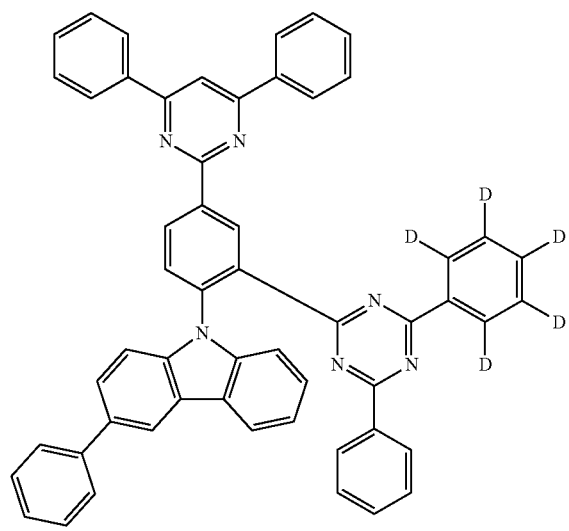
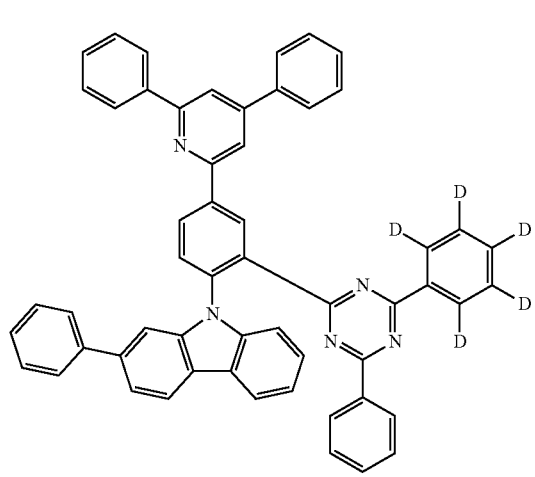
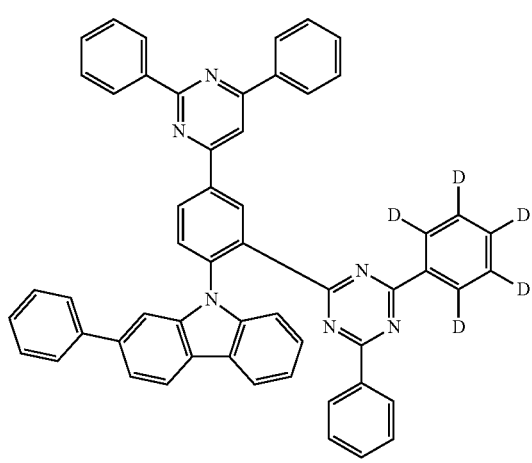
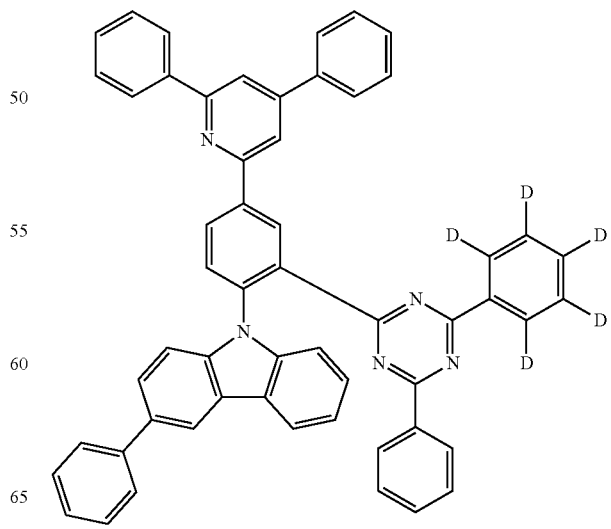

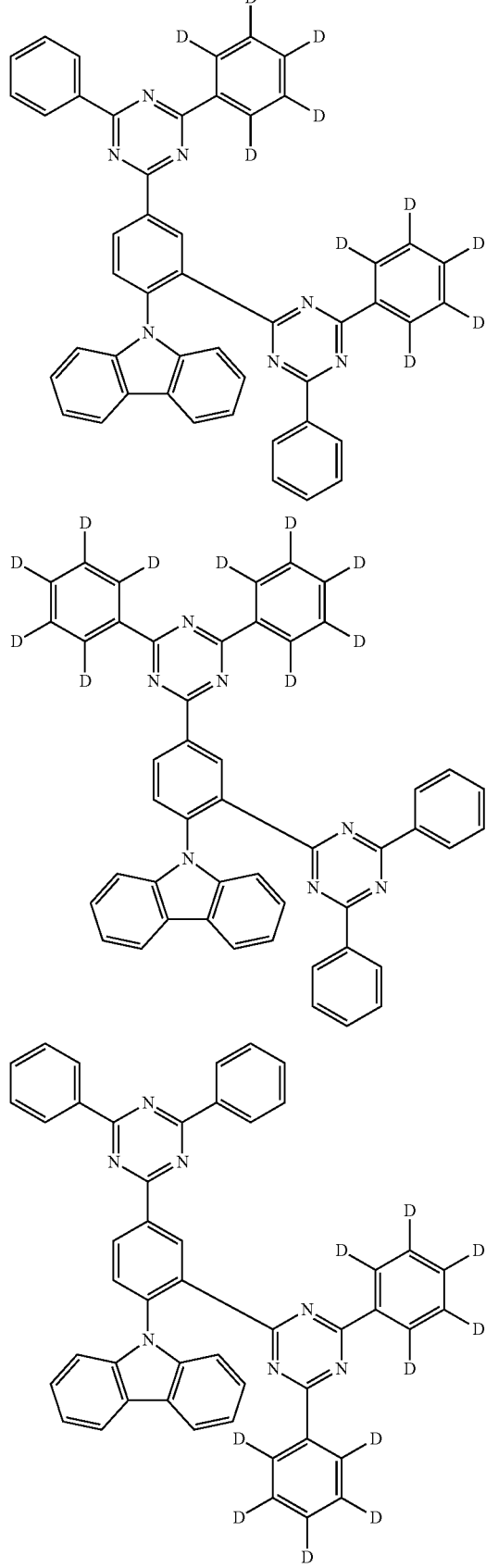
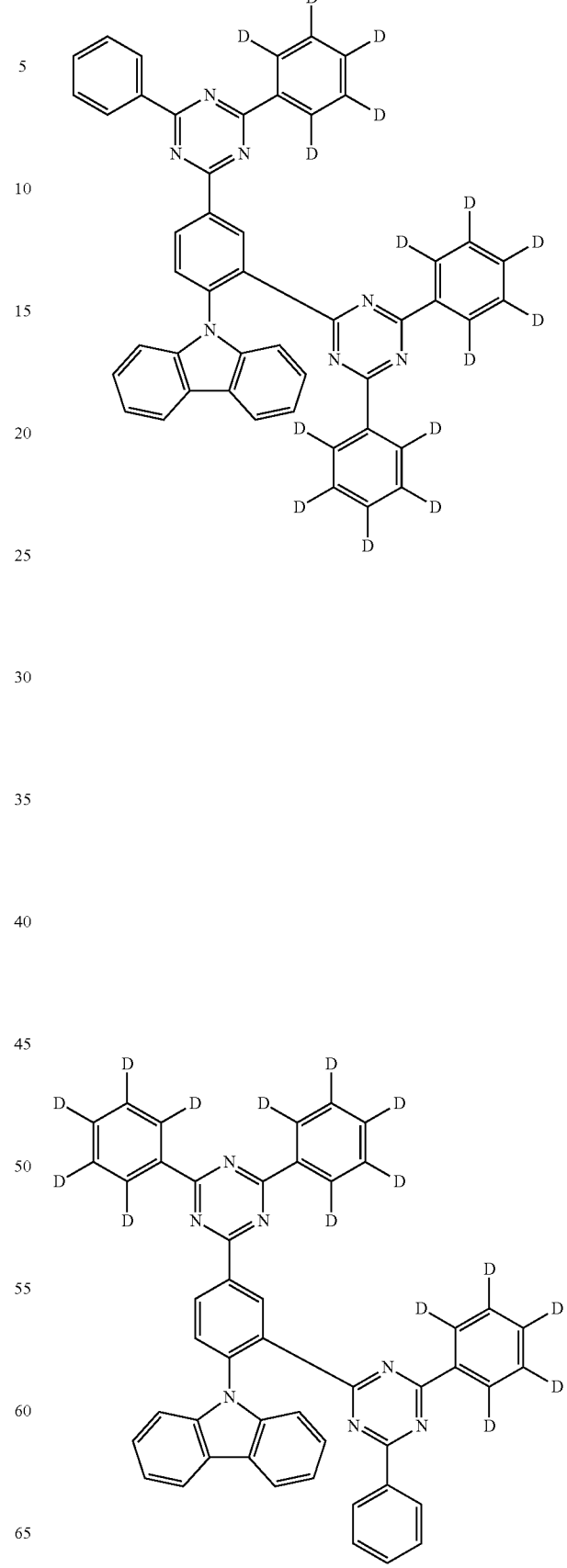

-continued
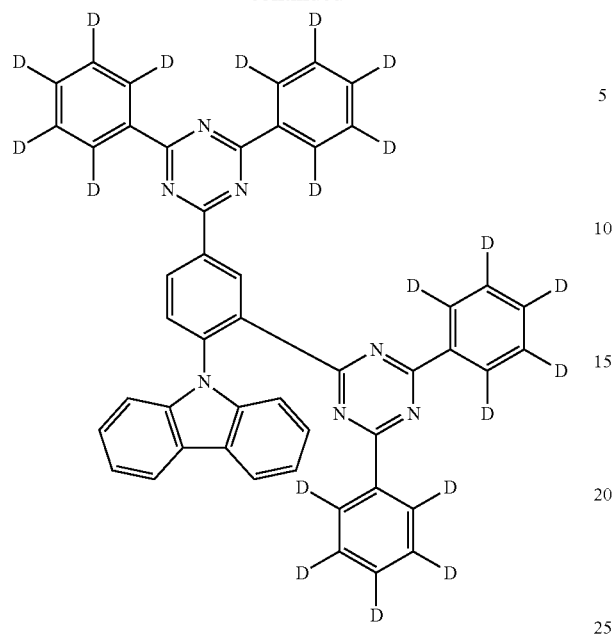
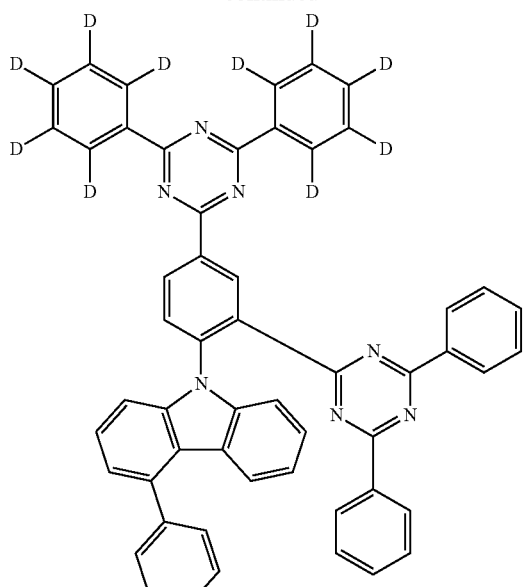
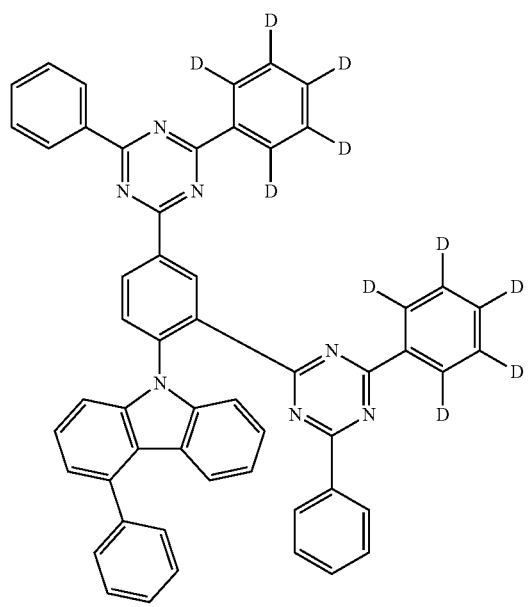
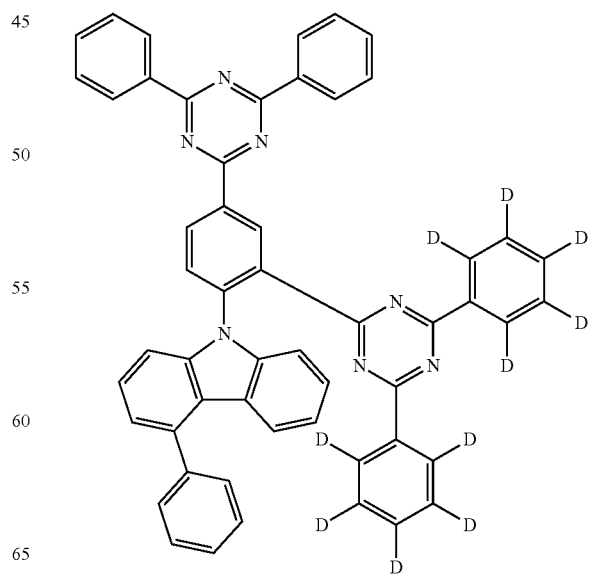

25
-continued
26
-continued
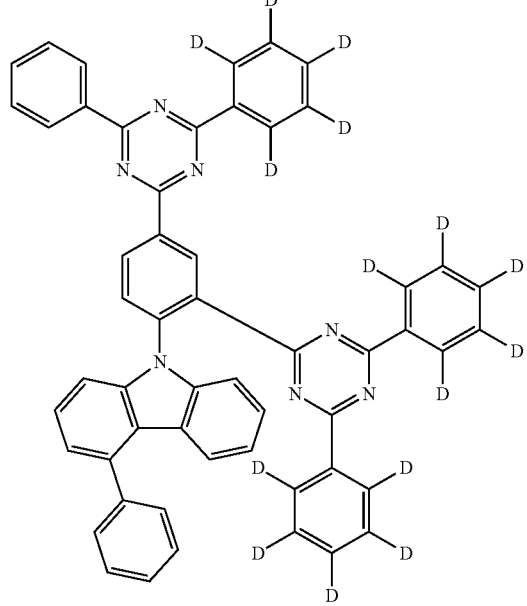
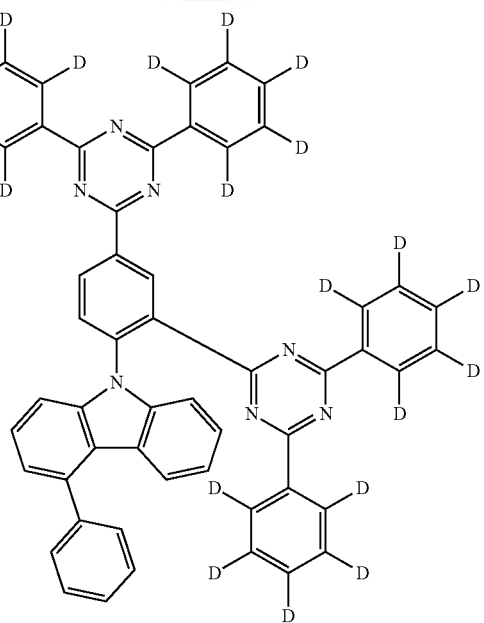
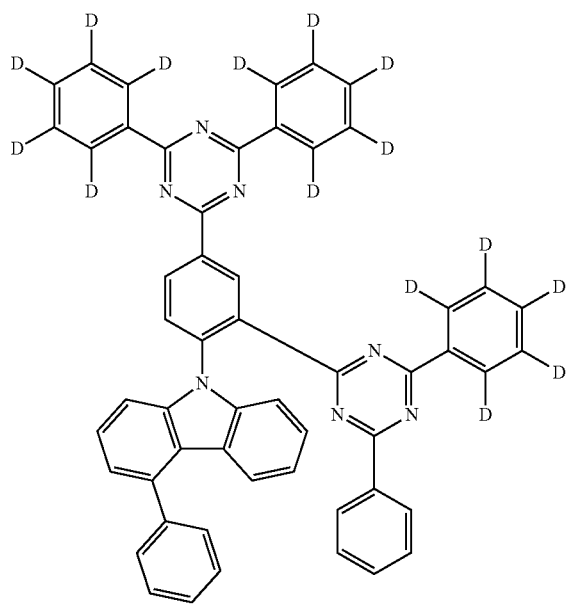

27
-continued
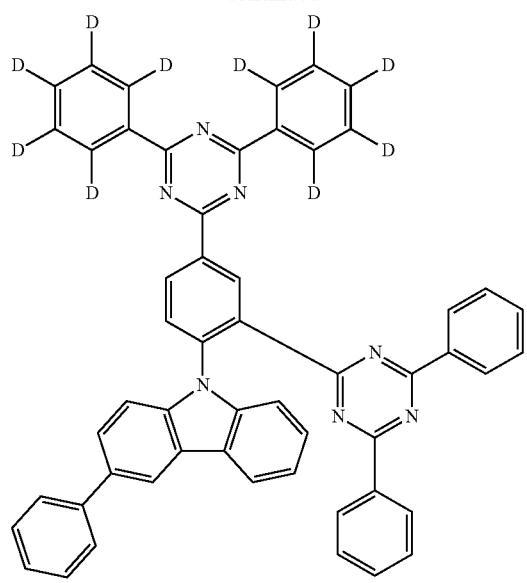
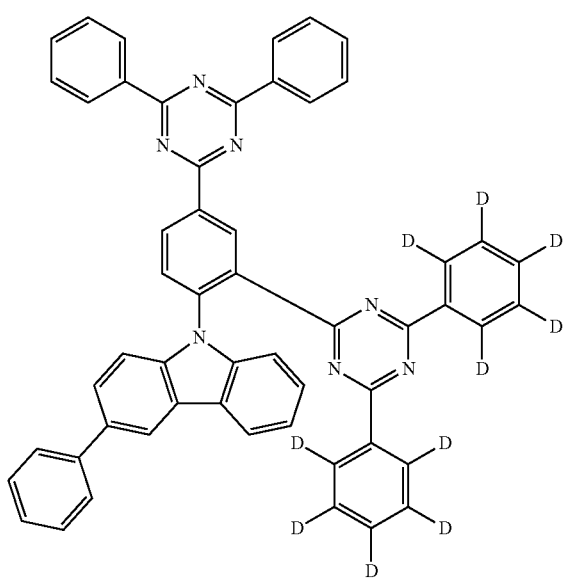
28
-continued
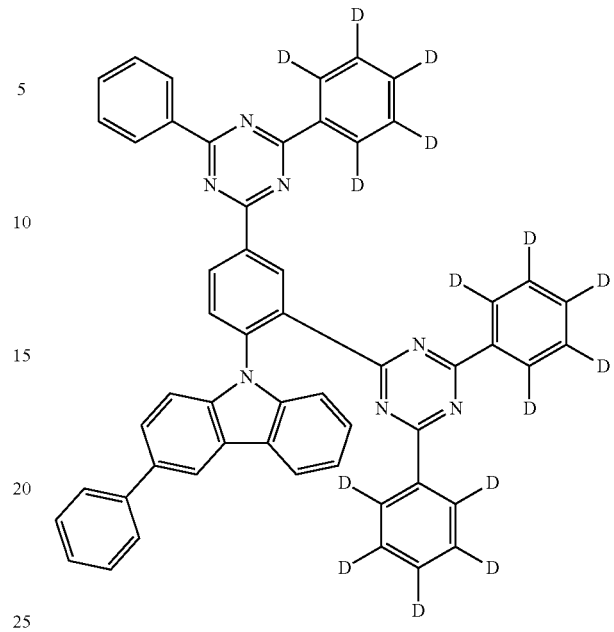
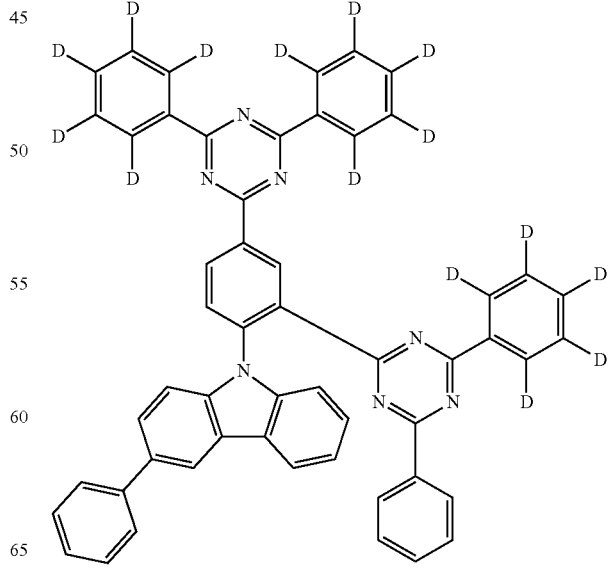

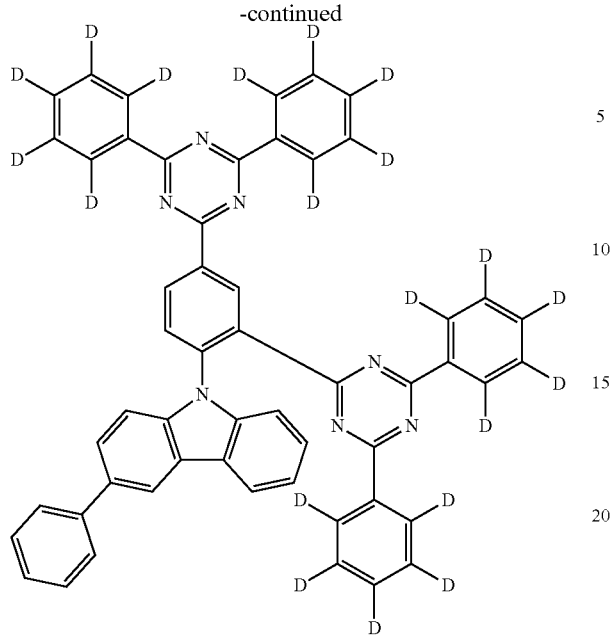
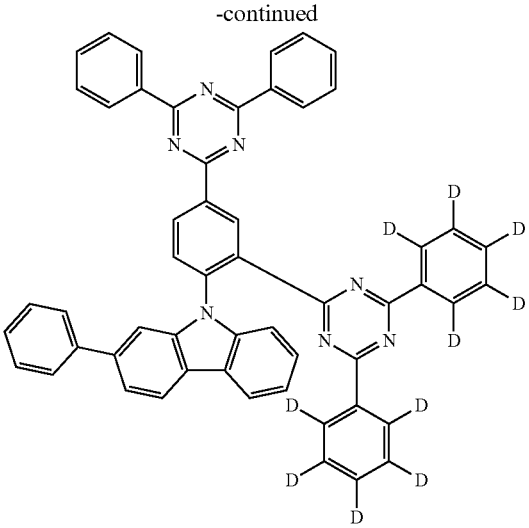
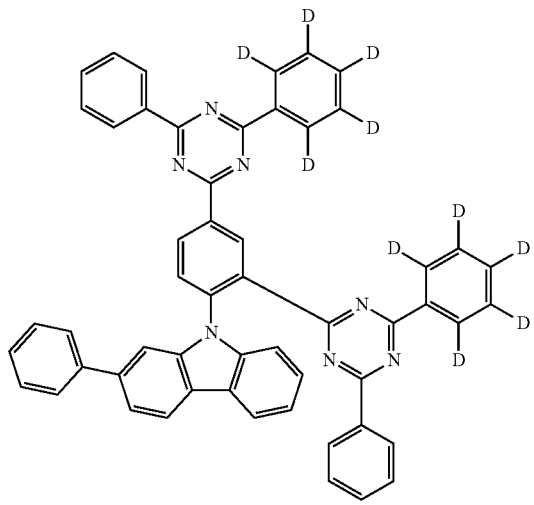
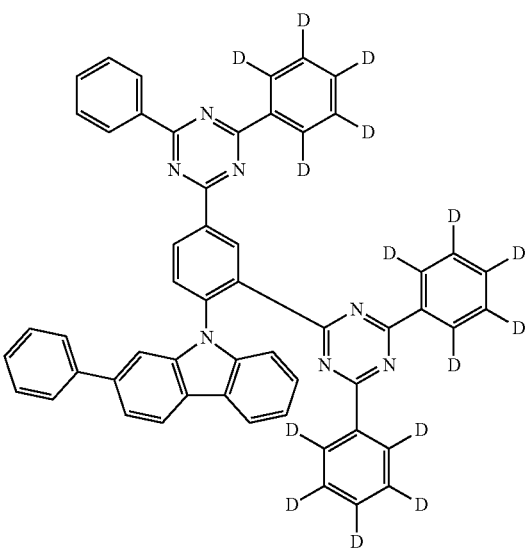
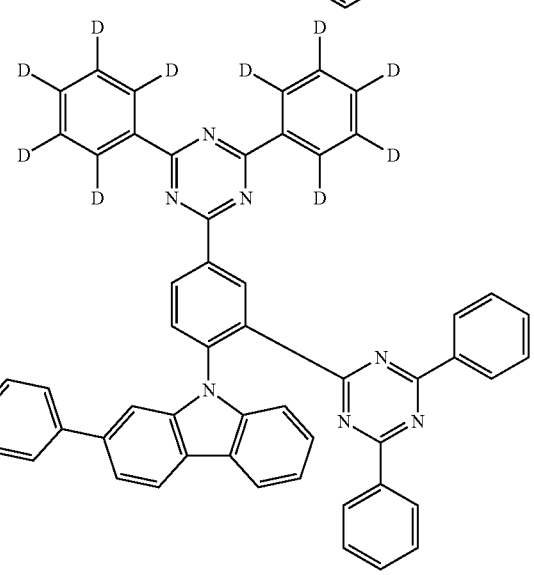
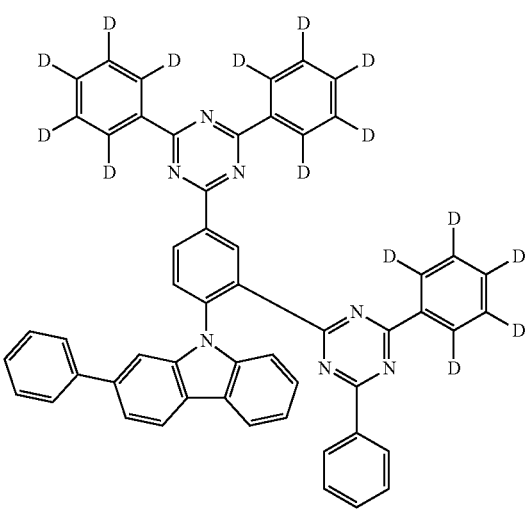

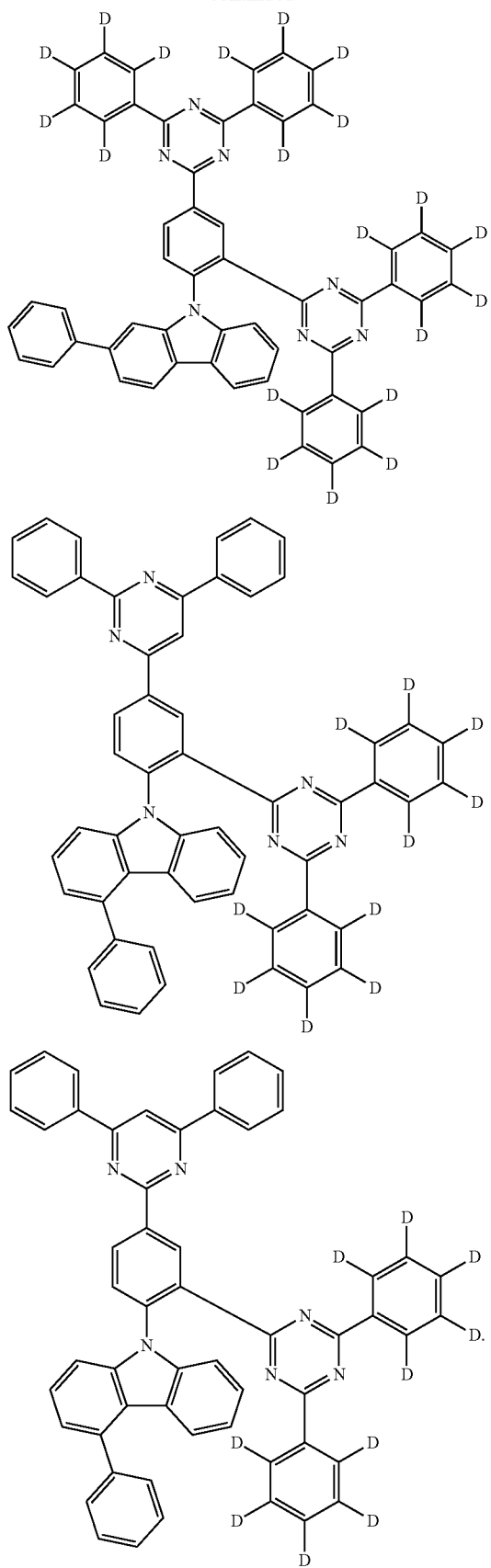
The compound of Chemical Formula 1 can be prepared, for example, in accordance with a preparation method as shown in Reaction Scheme 1 or Reaction Scheme 2 below, and the other remaining compounds can be prepared in a similar manner.
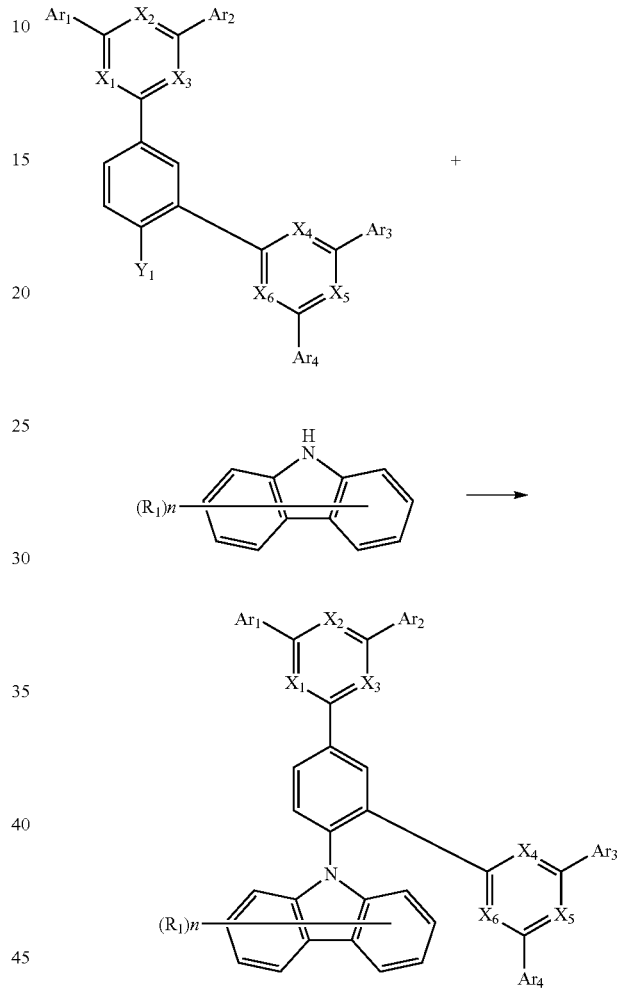
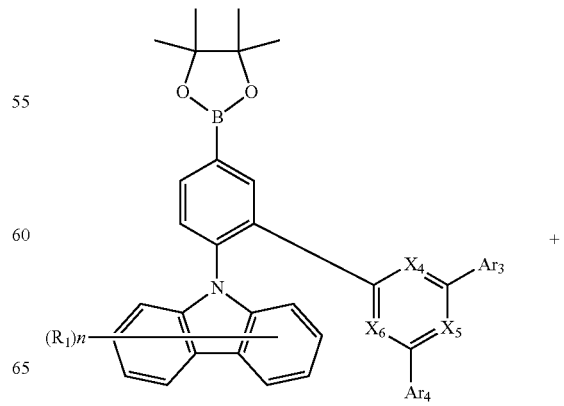

-continued

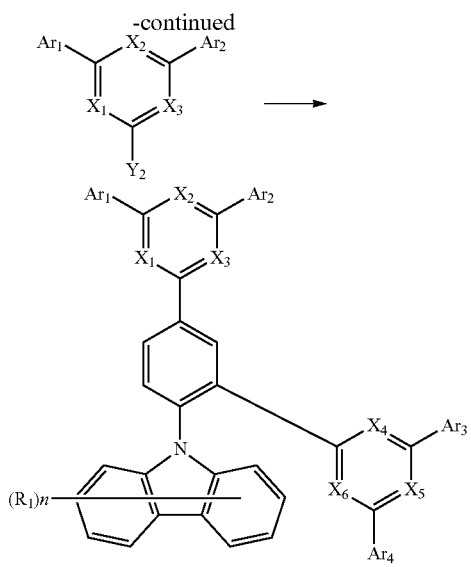

In Reaction Schemes 1 and 2, $X_1$ to $X_6$, $Ar_1$ to $Ar_4$, $R_1$ and n are the same as defined in Chemical Formula 1, $Y_1$ and $Y_2$ are each independently halogen, and preferably $Y_1$ and $Y_2$ are each independently chloro or bromo.

Reaction Scheme 1 is an amine substitution reaction, which is preferably carried out in the presence of a palladium catalyst and a base, and a reactive group for the amine substitution reaction can be modified as known in the art. Further, Reaction Scheme 2 is a Suzuki coupling reaction, which is preferably carried out in the presence of a palladium catalyst and a base, and a reactive group for the Suzuki coupling reaction can be modified as known in the art. The above preparation method can be further embodied in the Preparation Examples described hereinafter.

Another embodiment of the present disclosure provides an organic light emitting device including a compound of Chemical Formula 1 described above. As an example, there is provided an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present disclosure can have a single-layer structure, or it can have a multilayered structure in which two or more organic material layers are stacked. For example, the organic light emitting device of the present disclosure can have a structure comprising a hole injection layer, a hole transport layer, an electron blocking layer, a light emitting layer, an electron transport layer, an electron injection layer and the like as the organic material layer. However, the structure of the organic light emitting device is not limited thereto, and it can include a smaller number of organic material layers.

Further, the organic material layer can include a light emitting layer, wherein the light emitting layer can include the compound of Chemical Formula 1. In particular, the compound according to the present disclosure can be used as a host of the light emitting layer.

Further, the organic material layer can include a hole transport layer, a hole injection layer, or a layer for simultaneously performing hole transport and hole injection, wherein the hole transport layer, the hole injection layer, or the layer for simultaneously performing hole transport and hole injection can include the compound of Chemical Formula 1.

Further, the organic material layer can include an electron transport layer, an electron injection layer, and a layer for simultaneously performing electron transport and electron injection, wherein the electron transport layer, the electron injection layer, and the layer for simultaneously performing electron transport and electron injection can include the compound of Chemical Formula 1.

In addition, the organic material layer includes a light emitting layer and a hole transport layer, wherein the light emitting layer and the hole transport layer can include a compound of Chemical Formula 1.

Further, the organic light emitting device according to the present disclosure can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound of Chemical Formula 1 can be included in one or more layers of the hole injection layer, the hole transport layer, the electron blocking layer, the light emitting layer, the electron transport layer and the electron injection layer.

The organic light emitting device according to the present disclosure can be manufactured by materials and methods known in the art, except that one or more layers of the organic material layers include the compound of Chemical Formula 1. In addition, when the organic light emitting device includes a plurality of organic material layers, the organic material layers can be formed of the same material or different materials.

For example, the organic light emitting device according to the present disclosure can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as $LiF/Al$ or $LiO_2/Al$; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is a layer provided between the hole transport layer and the light emitting layer in order to prevent the electrons injected in the cathode from being transferred to the hole transport layer without being recombined in the light emitting layer, which can also be referred to as an electron inhibition layer. The electron blocking layer is preferably a material having a smaller electron affinity than the electron transport layer.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound, a dimerized styryl compound, BAlq, a 10-hydroxybenzoquinoline-metal compound, a benzoxazole, a benzothiazole, a benzimidazole-based compound, a poly(p-phenylenevinylene)(PPV)-based polymer, a spiro compound, polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto. Preferably, the compound of Chemical Formula 1 can be included as a host material.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has a large mobility for electrons. Specific examples of the electron transport material include: an Al complex of 8-hydroxyquinoline, a complex including $Alq_3$, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxy-benzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)-(2-naphtholato)gallium, and the like, but are not limited thereto.

The organic light emitting device according to the present disclosure can be a front side emission type, a back side emission type, or a double side emission type according to the used material.

In addition, the compound of Chemical Formula 1 can be included in an organic solar cell or an organic transistor in addition to an organic light emitting device.

Hereinafter, embodiments will be described in more detail to facilitate understanding of the invention. However, the following examples are provided for illustrative purposes only and are not intended to limit the scope of the present disclosure.

PREPARATION EXAMPLES

Preparation Example 1: Preparation of Intermediate Compounds T-1 to T-4

1) Preparation of Intermediate Compound T-1

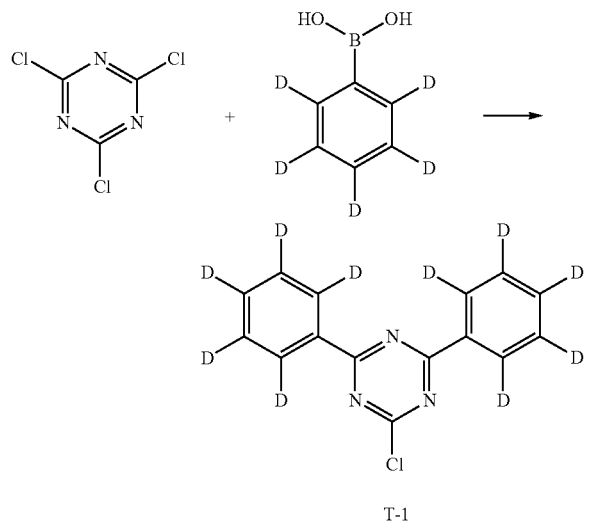

T-1

Cyanuric chloride (50 g, 273.3 mmol) and (phenyl-d5) boronic acid (34.7 g, 273.3 mmol) were added to 1000 ml of tetrahydrofuran under a nitrogen atmosphere, and the mixture was stirred and refluxed. Then, potassium carbonate (113.3 g, 820 mmol) was dissolved in 113 ml of water, added thereto and sufficiently stirred, and then tetrakistriphenyl-phosphinopalladium (9.5 g, 8.2 mmol) was added. After reacting for 3 hours, the reaction mixture was cooled to room temperature, the organic layer and the aqueous layer were separated, and then the organic layer was distilled. This was added again to 1515 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound T-1 (42.4 g, yield: 56%, MS: $[M+H]^+=278.1$).

2) Preparation of Intermediate Compound T-2

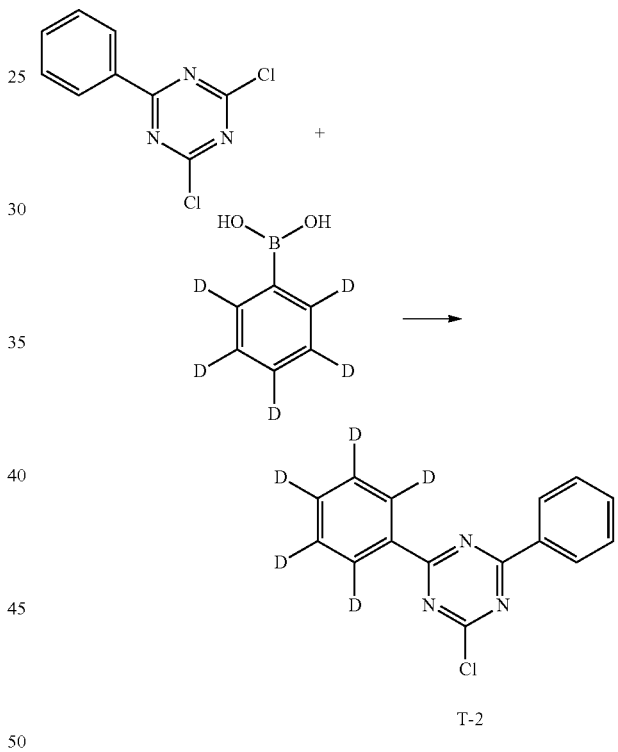

T-2

2,4-dichloro-6-phenyl-1,3,5-triazine (50 g, 222.2 mmol) and (phenyl-d5)boronic acid (28.2 g, 222.2 mmol) were added to 1000 ml of tetrahydrofuran under a nitrogen atmosphere, and the mixture was stirred and refluxed. Then, potassium carbonate (92.1 g, 666.7 mmol) was dissolved in 92 ml of water, added thereto and sufficiently stirred, and then tetrakistriphenyl-phosphinopalladium (7.7 g, 6.7 mmol) was added. After reacting for 1 hour, the reaction mixture was cooled to room temperature, the organic layer and the aqueous layer were separated, and then the organic layer was distilled. This was added again to 1209 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound T-2 (44.1 g, yield: 73%, MS: [M+H]$^+$=273.1).

3) Preparation of Intermediate Compound T-3

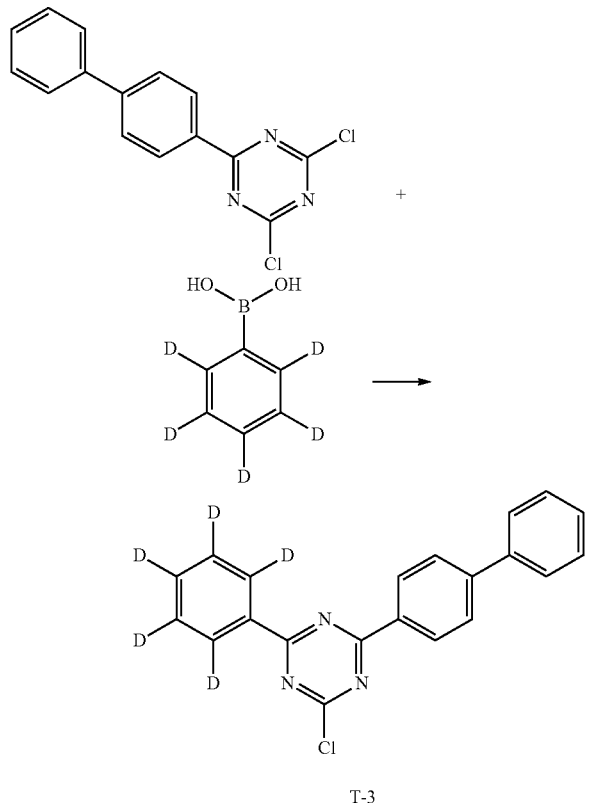

T-3

2-([1,1'-biphenyl]-4-yl)-4,6-dichloro-1,3,5-triazine (50 g, 166.1 mmol) and (phenyl-d5)boronic acid (21.1 g, 166.1 mmol) were added to 1000 ml of tetrahydrofuran under a nitrogen atmosphere, and the mixture was stirred and refluxed. Then, potassium carbonate (68.9 g, 498.3 mmol) was dissolved in 69 ml of water, added thereto and sufficiently stirred, and then tetrakistriphenyl-phosphinopalladium (5.8 g, 5 mmol) was added. After reacting for 3 hours, the reaction mixture was cooled to room temperature, the organic layer and the aqueous layer were separated, and then the organic layer was distilled. This was added again to 1156 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound T-3 (43.4 g, yield: 75%, MS: [M+H]$^+$=349.1).

4) Preparation of Intermediate Compound T-4

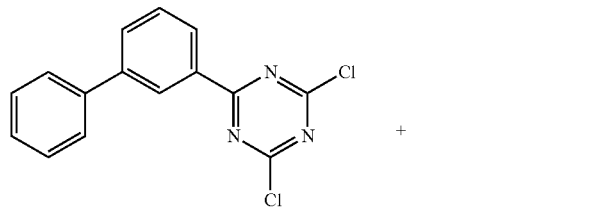

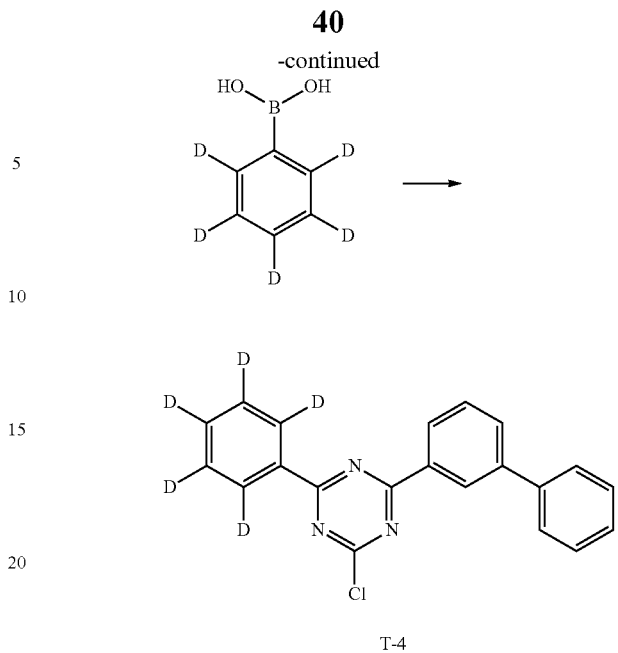

T-4

2-([1,1'-biphenyl]-3-yl)-4,6-dichloro-1,3,5-triazine (50 g, 166.1 mmol) and (phenyl-d5)boronic acid (21.1 g, 166.1 mmol) were added to 1000 ml of tetrahydrofuran under a nitrogen atmosphere, and the mixture was stirred and refluxed. Then, potassium carbonate (68.9 g, 498.3 mmol) was dissolved in 69 ml of water, added thereto and sufficiently stirred, and then tetrakistriphenyl-phosphinopalladium (5.8 g, 5 mmol) was added. After reacting for 3 hours, the reaction mixture was cooled to room temperature, the organic layer and the aqueous layer were separated, and then the organic layer was distilled. This was added again to 1156 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound T-4 (44.5 g, yield: 77%, MS: [M+H]$^+$=349.1).

Preparation Example 2: Preparation of Intermediate Compound Sub 1

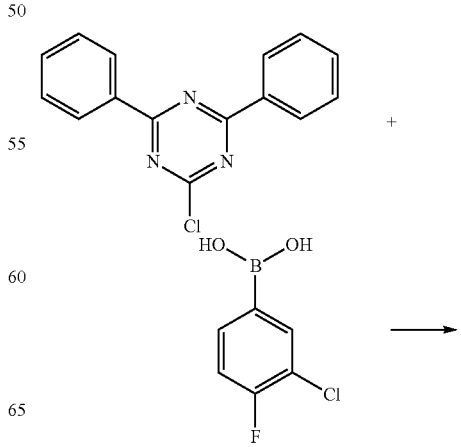

-continued

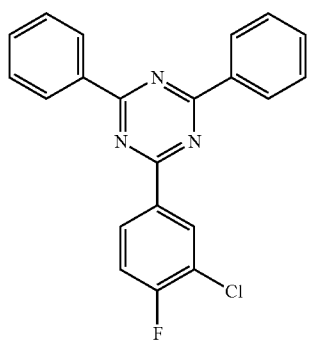

1-1

2-Chloro-4,6-diphenyl-1,3,5-triazine (30 g, 112.3 mmol) and (3-chloro-4-fluorophenyl)boronic acid (19.5 g, 112.3 mmol) were added to 600 ml of tetrahydrofuran under a nitrogen atmosphere, and the mixture was stirred and refluxed. Then, potassium carbonate (46.6 g, 337 mmol) was dissolved in 47 ml of water, added thereto and sufficiently stirred, and then tetrakistriphenyl-phosphinopalladium (3.9 g, 3.4 mmol) was added. After reacting for 1 hour, the reaction mixture was cooled to room temperature, the organic layer and the aqueous layer were separated, and then the organic layer was distilled. This was added again to 811 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound 1-1 (26.4 g, yield: 65%, MS: [M+H]$^+$=362.1).

-continued

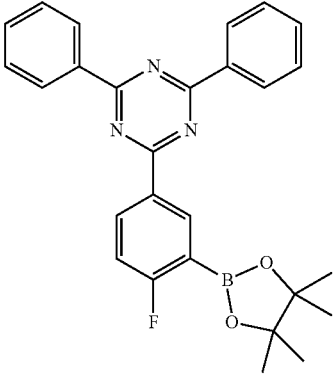

1-2

Compound 1-1 (20 g, 55.4 mmol) and bis(pinacolato)diboron (28.2 g, 110.8 mmol) were added to 400 ml of dioxane under a nitrogen atmosphere, and the mixture was stirred and refluxed. Then, potassium acetate (16 g, 166.2 mmol) was added thereto and sufficiently stirred, and then palladium dibenzylidene acetone palladium (1 g, 1.7 mmol) and tricyclohexylphosphine (0.9 g, 3.3 mmol) were added. After reacting for 7 hours, the reaction mixture was cooled to room temperature and then the organic layer was subjected to filtration treatment to remove a salt, and then the filtered organic layer was distilled. This was added again to 251 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound 1-2 (22.3 g, yield: 89%, MS: [M+H]+=454.2).

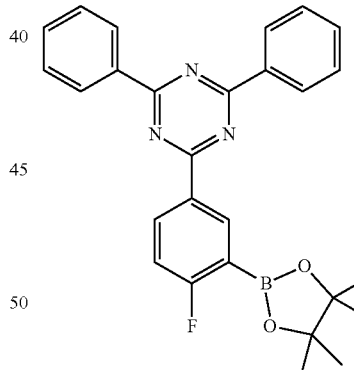

1-2

+

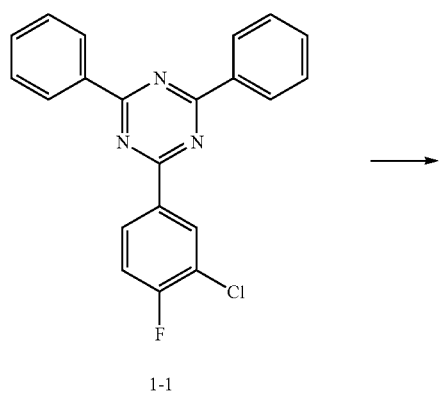

1-1

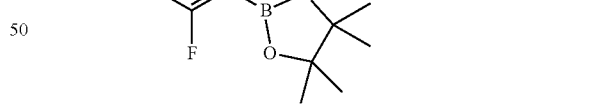

T-2

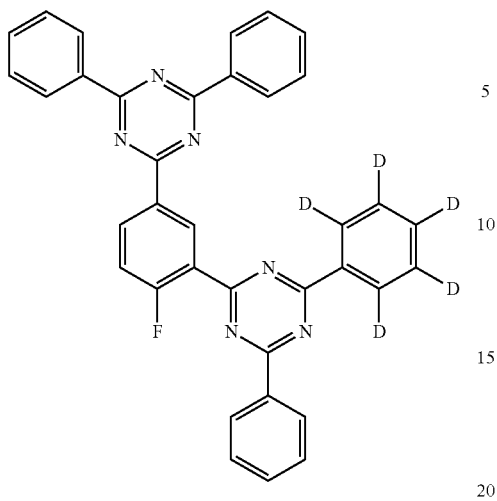

Sub 1

Compound 1-2 (30 g, 66.2 mmol) and Compound T-2 (18 g, 66.2 mmol) were added to 600 ml of tetrahydrofuran under a nitrogen atmosphere, and the mixture was stirred and refluxed. Then, potassium carbonate (27.4 g, 198.6 mmol) was dissolved in 27 ml of water, added thereto and sufficiently stirred, and then tetrakistriphenyl-phosphinopalladium (2.3 g, 2 mmol) was added. After reacting for 3 hours, the reaction mixture was cooled to room temperature, the organic layer and the aqueous layer were separated, and the organic layer was distilled. This was added again to 746 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a white solid compound sub 1 (20.5 g, yield: 55%, MS: [M+H]+=564.2).

Preparation Example 3: Preparation of Intermediate Compound Sub 2

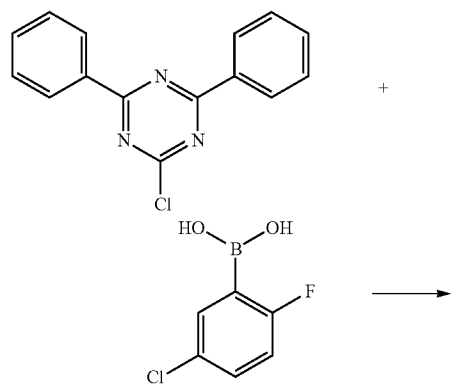

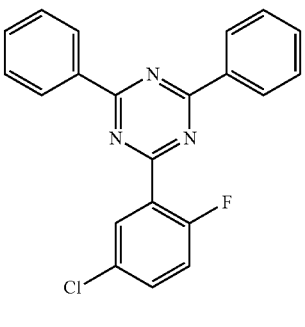

2-1

2-Chloro-4,6-diphenyl-1,3,5-triazine (30 g, 112.3 mmol) and (5-chloro-2-fluorophenyl)boronic acid (19.5 g, 112.3 mmol) were added to 600 ml of tetrahydrofuran under a nitrogen atmosphere, and the mixture was stirred and refluxed. Then, potassium carbonate (46.6 g, 337 mmol) was dissolved in 47 ml of water, added thereto and sufficiently stirred, and then tetrakistriphenyl-phosphinopalladium (3.9 g, 3.4 mmol) was added. After reacting for 1 hour, the reaction mixture was cooled to room temperature, the organic layer and the aqueous layer were separated, and the organic layer was distilled. This was added again to 811 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a white solid compound 2-1 (30.8 g, yield: 76%, MS: [M+H]+=362.1).

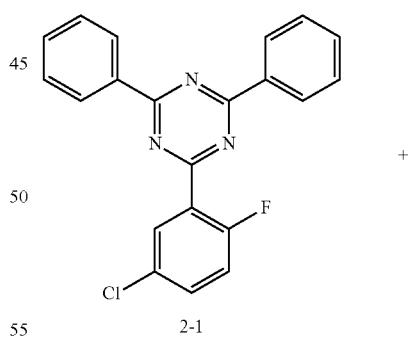

2-1

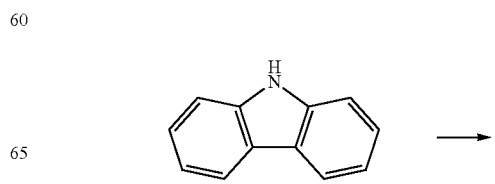

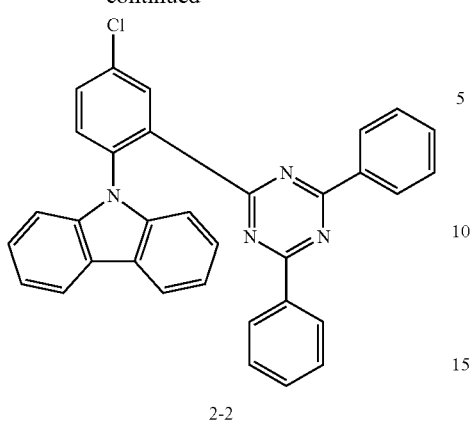

2-2

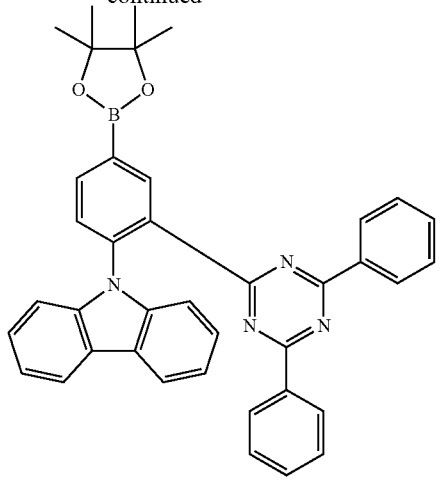

Sub 2

Compound 2-1 (20 g, 55.4 mmol) and 9H-carbazole (9.3 g, 55.4 mmol) were added to 400 ml of xylene under a nitrogen atmosphere, and the mixture was stirred and refluxed. Then, sodium tert-butoxide (16 g, 166.2 mmol) was added thereto and sufficiently stirred, and then bis(tri-tert-butylphosphine)palladium (0.8 g, 1.7 mmol) was added. After reacting for 5 hours, the reaction mixture was cooled to room temperature and then the produced solid was filtered. The solid was added to 844 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a white solid compound 2-2 (20.8 g, yield: 74%, MS: [M+H]+=509.2).

Compound 2-2 (20 g, 39.4 mmol) and bis(pinacolato)diboron (20 g, 78.7 mmol) were added to 400 ml of dioxane under a nitrogen atmosphere, and the mixture was stirred and refluxed. Then, potassium acetate (11.3 g, 118.1 mmol) was added thereto and sufficiently stirred, and then palladium dibenzylidene acetone palladium (0.7 g, 1.2 mmol) and tricyclohexylphosphine (0.7 g, 2.4 mmol) were added. After reacting for 7 hours, the reaction mixture was cooled to room temperature and then the organic layer was subjected to filtration treatment to remove a salt, and then the filtered organic layer was distilled. This was added again to 178 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound sub 2 (14.4 g, yield: 81%, MS: [M+H]+=454.2).

Preparation Example 4: Preparation of Intermediate Compound Sub 3

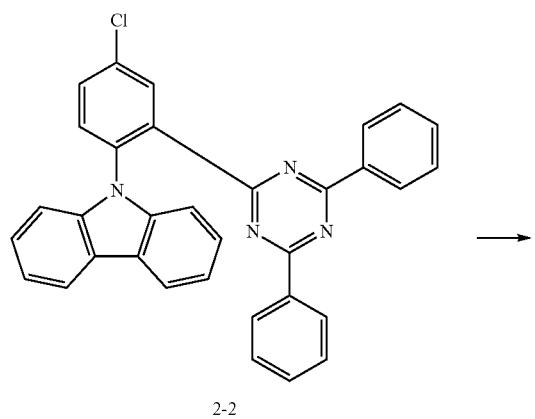

2-2

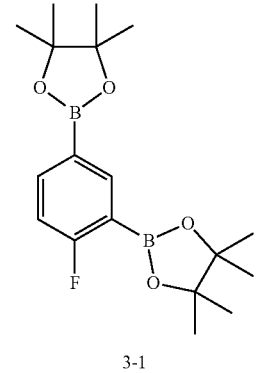

3-1

2,4-Dibromo-1-fluorobenzene (50 g, 98.4 mmol) and bis(pinacolato)diboron (50 g, 196.8 mmol) were added to 1000 ml of dioxane under a nitrogen atmosphere, and the mixture was stirred and refluxed. Then, potassium acetate (28.4 g, 295.2 mmol) was added thereto and sufficiently stirred, and then palladium dibenzylidene acetone palladium (1.7 g, 3 mmol) and tricyclohexylphosphine (1.7 g, 5.9 mmol) were added. After reacting for 3 hours, the reaction mixture was cooled to room temperature and then the organic layer was subjected to filtration treatment to remove a salt, and then the filtered organic layer was distilled. This was added again to 343 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound 3-1 (30.2 g, yield: 88%, MS: [M+H]+=349.2).

under a nitrogen atmosphere, and the mixture was stirred and refluxed. Then, potassium carbonate (35.7 g, 258.5 mmol) was dissolved in 36 ml of water, added thereto and sufficiently stirred, and then tetrakistriphenyl-phosphinopalladium (3 g, 2.6 mmol) was added. After reacting for 1 hour, the reaction mixture was cooled to room temperature, the organic layer and the aqueous layer were separated, and then the organic layer was distilled. This was added again to 997 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a white solid compound sub 3 (34.4 g, yield: 69%, MS: [M+H]+=579.3).

Preparation Example 5: Preparation of Intermediate Compound Sub 4

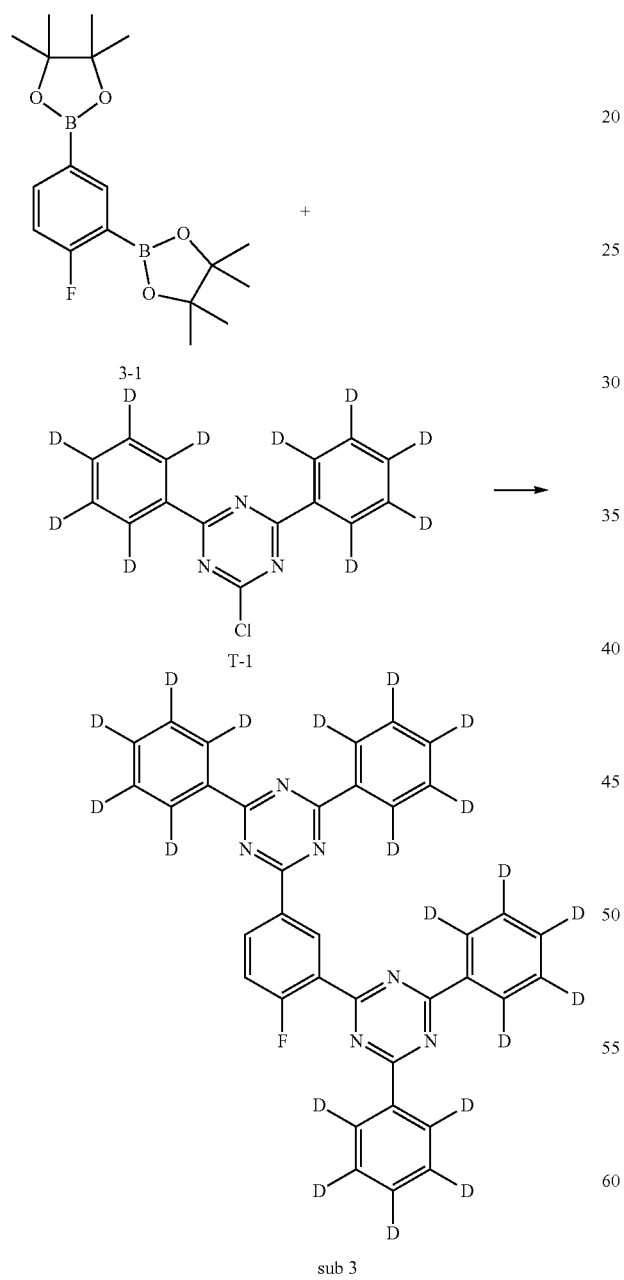

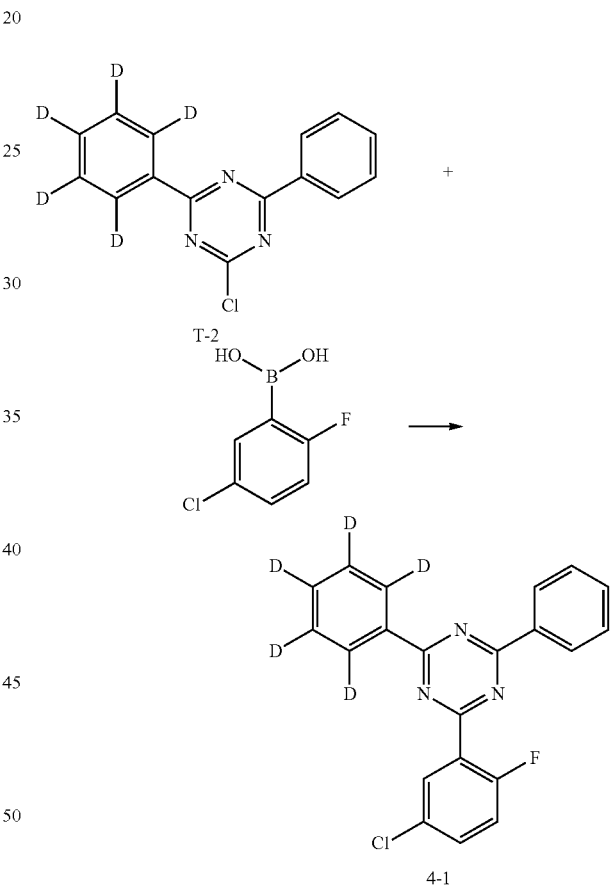

Compound T-2 (50 g, 183.8 mmol) and (5-chloro-2-fluorophenyl)boronic acid (32 g, 183.8 mmol) were added to 1000 ml of tetrahydrofuran under a nitrogen atmosphere, and the mixture was stirred and refluxed. Then, potassium carbonate (76.2 g, 551.3 mmol) was dissolved in 76 ml of water, added thereto and sufficiently stirred, and then tetrakistriphenyl-phosphinopalladium (6.4 g, 5.5 mmol) was added. After reacting for 3 hours, the reaction mixture was cooled to room temperature, the organic layer and the aqueous layer were separated, and then the organic layer was distilled. This was added again to 1346 ml of chloroform, dissolved and washed twice with water. The organic layer was then separated, anhydrous magnesium sulfate was Compound 3-1 (30 g, 86.2 mmol) and Compound T-1 (23.9 g, 86.2 mmol) were added to 600 ml of tetrahydrofuran added, stirred and then filtered. The filtrate was distilled under reduced pressure. The concentrated compound was purified by a silica column using chloroform and ethyl acetate to give a white solid compound 4-1 (41.7 g, yield: 62%, MS: [M+H]+=367.1).

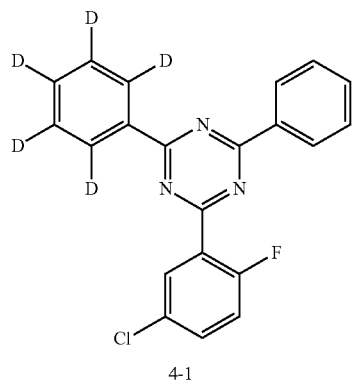

4-1

+

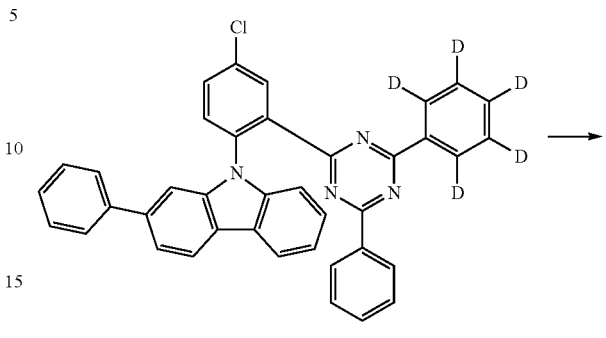

4-2

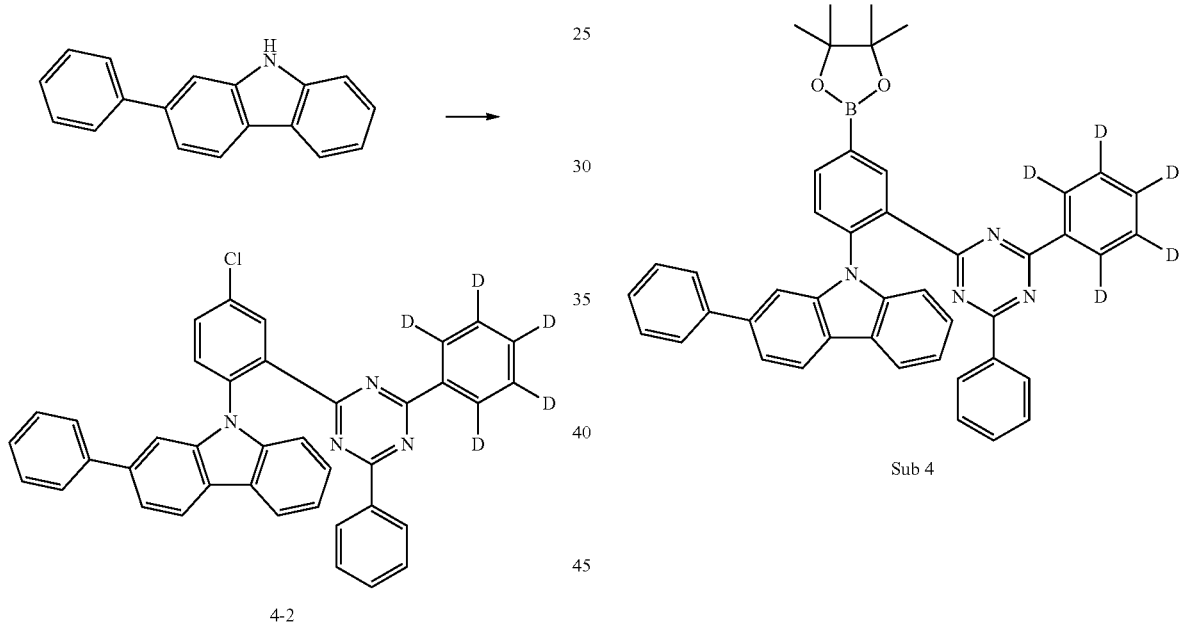

Compound 4-1 (20 g, 54.6 mmol) and 2-phenyl-9H-carbazole (20.0 g, 54.6 mmol) were added to 400 ml of xylene under a nitrogen atmosphere, and the mixture was stirred and refluxed. Then, sodium tert-butoxide (15.8 g, 163.9 mmol) was added thereto and sufficiently stirred, and then bis(tri-tert-butylphosphine)palladium (0.8 g, 1.6 mmol) was added. After reacting for 1 hour, the reaction mixture was cooled to room temperature and then the produced solid was filtered. The solid was added to 966 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a white solid compound 4-2 (21.9 g, yield: 68%, MS: [M+H]+=590.2).

Compound 4-2 (20 g, 33.9 mmol) and bis(pinacolato)diboron (17.3 g, 67.9 mmol) were added to 400 ml of dioxane under a nitrogen atmosphere, and the mixture was stirred and refluxed. Then, potassium acetate (9.8 g, 101.8 mmol) was added thereto and sufficiently stirred, and then palladium dibenzylidene acetone palladium (0.6 g, 1 mmol) and tricyclohexylphosphine (0.6 g, 2 mmol) were added. After reacting for 7 hours, the reaction mixture was cooled to room temperature and then the organic layer was subjected to filtration treatment to remove a salt, and then the filtered organic layer was distilled. This was added again to 231 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound sub 4 (12.3 g, yield: 53%, MS: [M+H]+=682.4).

Preparation Example 6: Preparation of Intermediate Compound Sub 5

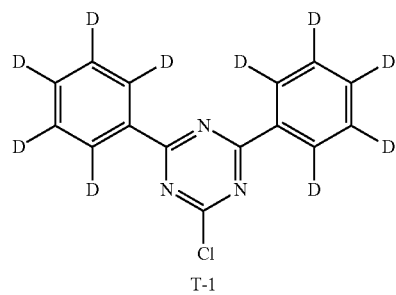

T-1

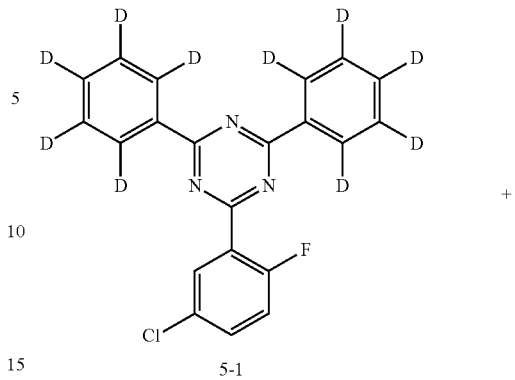

5-1

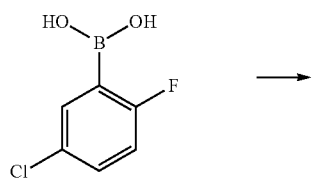

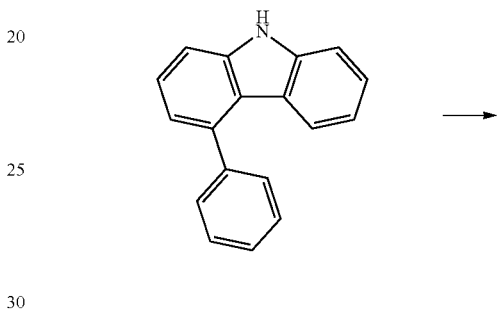

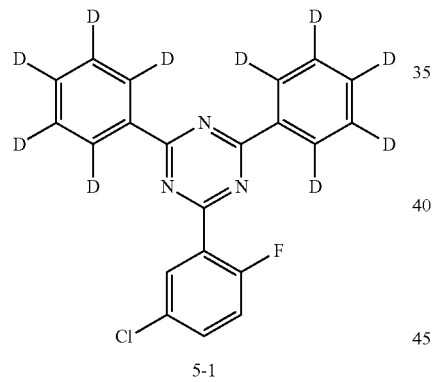

5-1

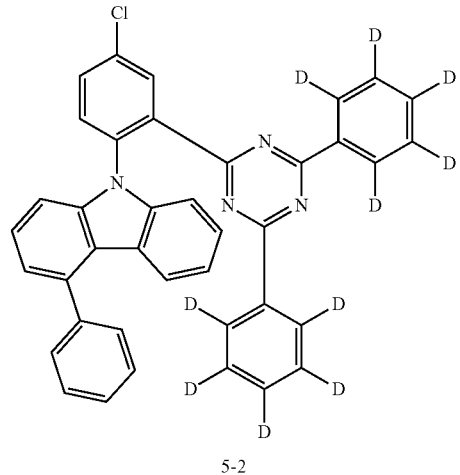

5-2

Compound T-1 (50 g, 180.4 mmol) and (5-chloro-2-fluorophenyl)boronic acid (31.4 g, 180.4 mmol) were added to 1000 ml of tetrahydrofuran under a nitrogen atmosphere, and the mixture was stirred and refluxed. Then, potassium carbonate (74.8 g, 541.3 mmol) was dissolved in 75 ml of water, added thereto and sufficiently stirred, and then tetrakistriphenyl-phosphinopalladium (6.3 g, 5.4 mmol) was added. After reacting for 3 hours, the reaction mixture was cooled to room temperature, the organic layer and the aqueous layer were separated, and then the organic layer was distilled. This was added again to 1339 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound 5-1 (39.5 g, yield: 59%, MS: [M+H]$^+$=372.1).

Compound 5-1 (30 g, 80.8 mmol) and 4-phenyl-9H-carbazole (30 g, 80.8 mmol) were added to 600 ml of xylene under a nitrogen atmosphere, and the mixture was stirred and refluxed. Then, sodium tert-butoxide (23.3 g, 242.5 mmol) was added thereto and sufficiently stirred, and then bis(tri-tert-butylphosphine)palladium (1.2 g, 2.4 mmol) was added. After reacting for 1 hour, the reaction mixture was cooled to room temperature and then the produced solid was filtered. The solid was added to 1441 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a white solid compound 5-2 (31.2 g, yield: 65%, MS: [M+H]+=595.2).

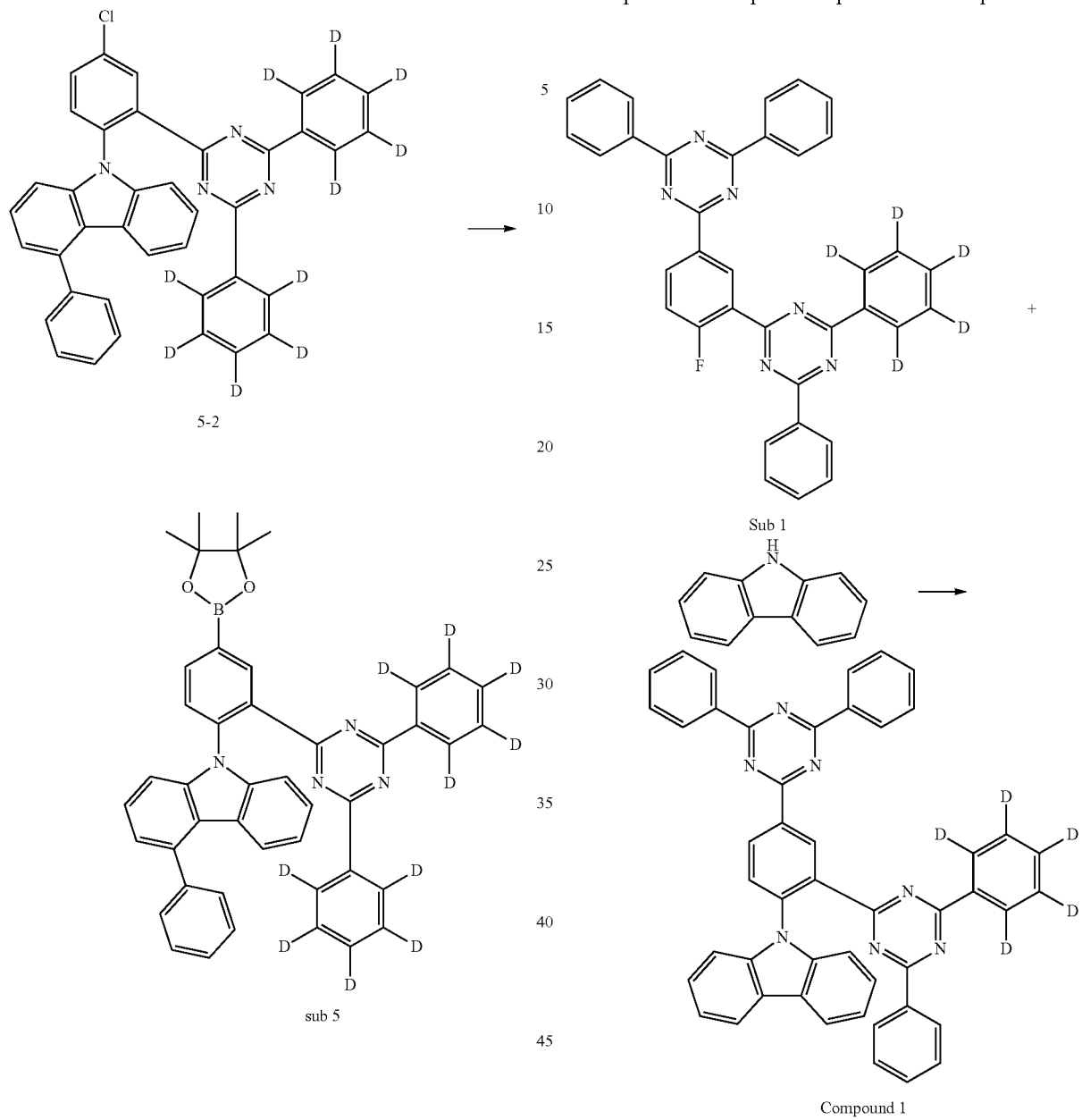

Preparation Example 7: Preparation of Compound 1

Compound 5-2 (20 g, 33.7 mmol) and bis(pinacolato) diboron (17.1 g, 67.3 mmol) were added to 400 ml of dioxane under a nitrogen atmosphere, and the mixture was stirred and refluxed. Then, potassium acetate (9.7 g, 101 mmol) was added thereto and sufficiently stirred, and then palladium dibenzylidene acetone palladium (0.6 g, 1 mmol) and tricyclohexylphosphine (0.6 g, 2 mmol) were added. After reacting for 5 hours, the reaction mixture was cooled to room temperature and then the organic layer was subjected to filtration treatment to remove a salt, and then the filtered organic layer was distilled. This was added again to 231 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound sub 5 (13.4 g, yield: 58%, MS: [M+H]+=687.4).

Compound sub 1 (10 g, 17.8 mmol) and 9H-carbazole (3 g, 17.8 mmol) were added to 200 ml of dimethylformamide under a nitrogen atmosphere, and the mixture was stirred and refluxed. Then, sodium tert-butoxide (11.3 g, 53.3 mmol) was added thereto and sufficiently stirred, and then bis(tri-tert-butylphosphine)palladium (0.3 g, 0.5 mmol) was added. After reacting for 6 hours, the reaction mixture was cooled to room temperature and then the organic layer was subjected to filtration treatment to remove a salt, and then the filtered organic layer was distilled. This was added again to 126 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 1 (7.2 g, yield: 57%, MS: [M+H]+=711.3).

Preparation Example 8: Preparation of Compound 2

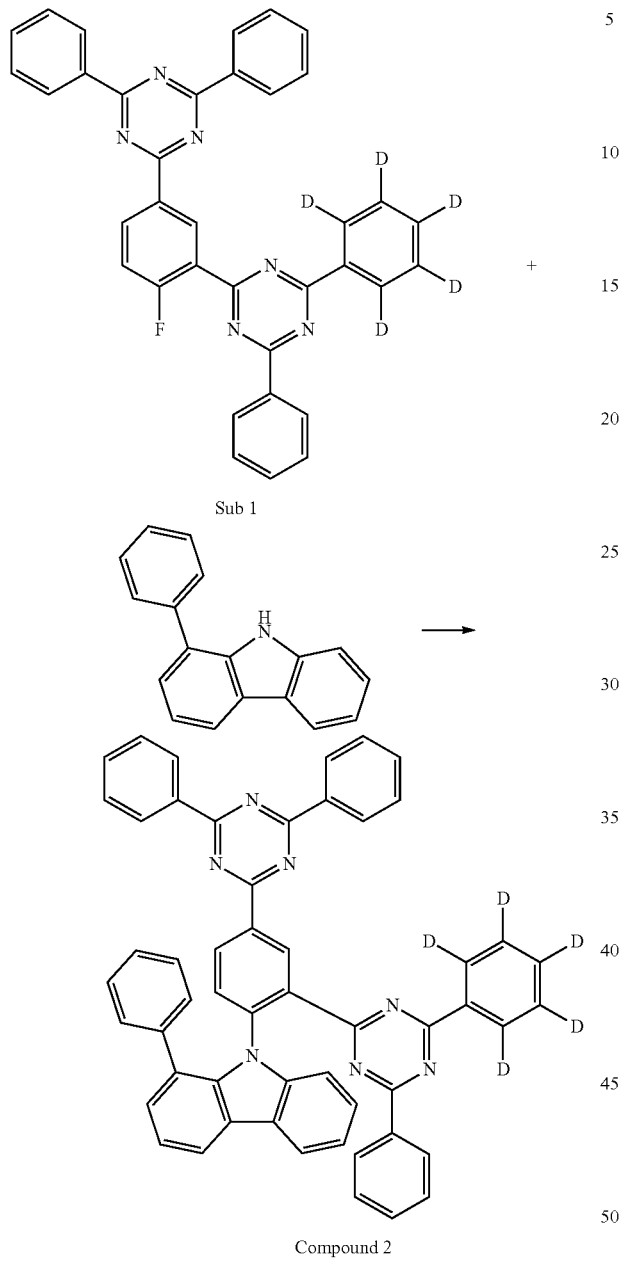

Sub 1

Compound 2

Preparation Example 9: Preparation of Compound 3

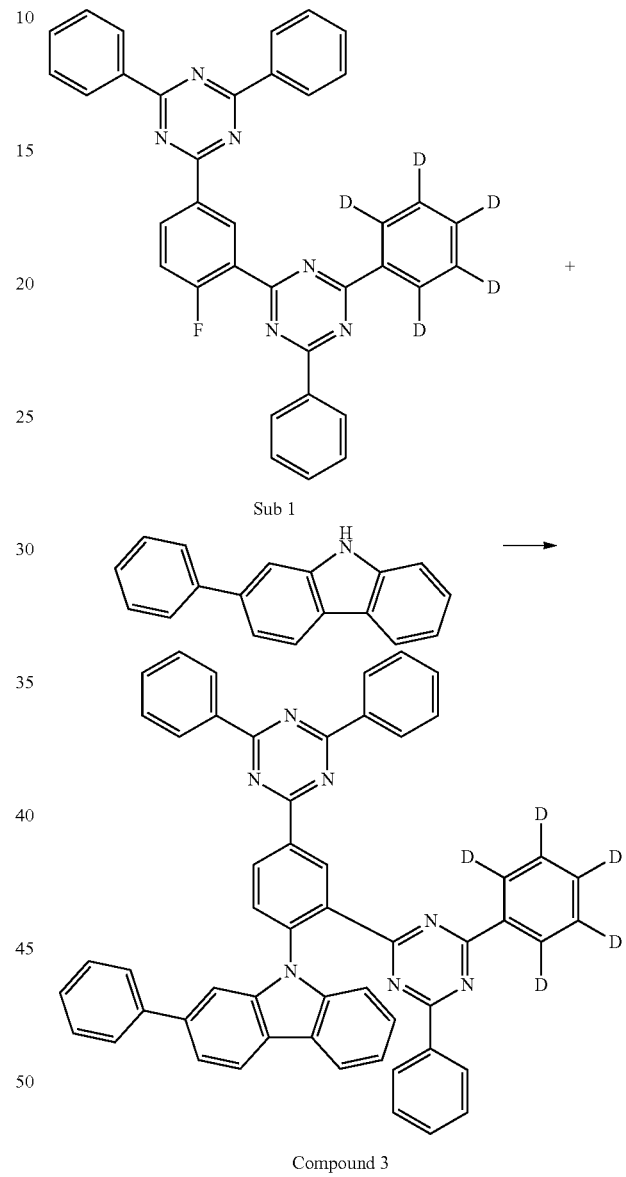

Sub 1

Compound 3

Compound sub 1 (10 g, 17.8 mmol) and 1-pheny-9H-carbazole (4.3 g, 17.8 mmol) were added to 200 ml of dimethylformamide under a nitrogen atmosphere, and the mixture was stirred and refluxed. Then, sodium tert-butoxide (11.3 g, 53.3 mmol) was added thereto and sufficiently stirred, and then bis(tri-tert-butylphosphine)palladium (0.3 g, 0.5 mmol) was added. After reacting for 7 hours, the reaction mixture was cooled to room temperature and then the organic layer was subjected to filtration treatment to remove a salt, and then the filtered organic layer was distilled. This was added again to 140 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 2 (7.7 g, yield: 55%, MS: [M+H]+=787.3).

Compound sub 1 (10 g, 17.8 mmol) and 2-pheny-9H-carbazole (8.9 g, 17.8 mmol) were added to 200 ml of dimethylformamide under a nitrogen atmosphere, and the mixture was stirred and refluxed. Then, sodium tert-butoxide (11.3 g, 53.3 mmol) was added thereto and sufficiently stirred, and then bis(tri-tert-butylphosphine)palladium (0.3 g, 0.5 mmol) was added. After reacting for 4 hours, the reaction mixture was cooled to room temperature and then the organic layer was subjected to filtration treatment to remove a salt, and then the filtered organic layer was distilled. This was added again to 140 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 3 (10.9 g, yield: 78%, MS: [M+H]+=787.3).

Preparation Example 10: Preparation of Compound 4

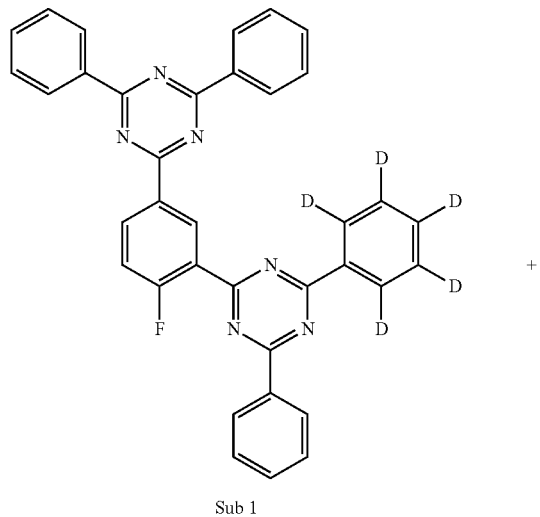

Compound sub 1 (10 g, 17.8 mmol) and 3-pheny-9H-carbazole (10.7 g, 17.8 mmol) were added to 200 ml of dimethylformamide under a nitrogen atmosphere, and the mixture was stirred and refluxed. Then, sodium tert-butoxide (11.3 g, 53.3 mmol) was added thereto and sufficiently stirred, and then bis(tri-tert-butylphosphine)palladium (0.3 g, 0.5 mmol) was added. After reacting for 6 hours, the reaction mixture was cooled to room temperature and then the organic layer was subjected to filtration treatment to remove a salt, and then the filtered organic layer was distilled. This was added again to 140 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 4 (8 g, yield: 57%, MS: [M+H]+=787.3).

Preparation Example 11: Preparation of Compound 5

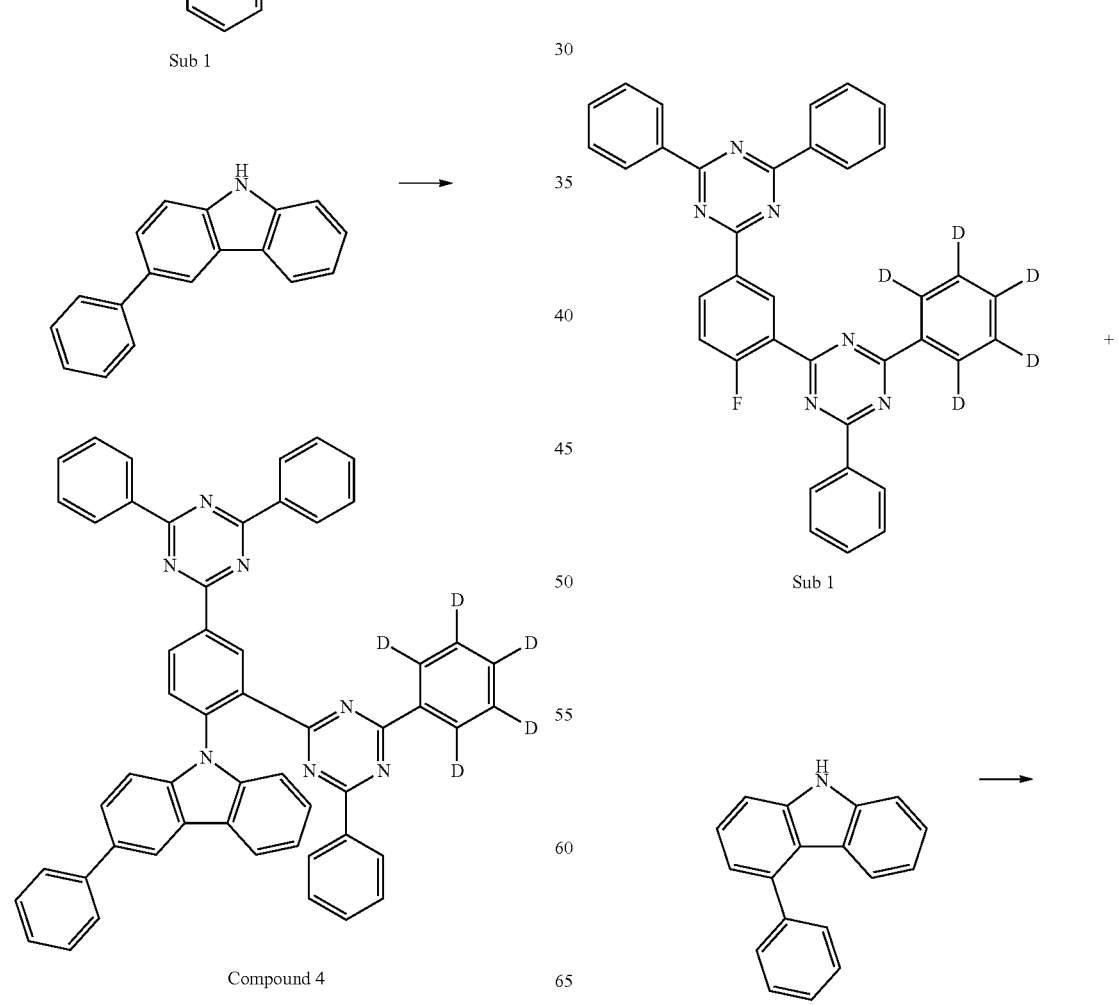

Preparation Example 12: Preparation of Compound 6

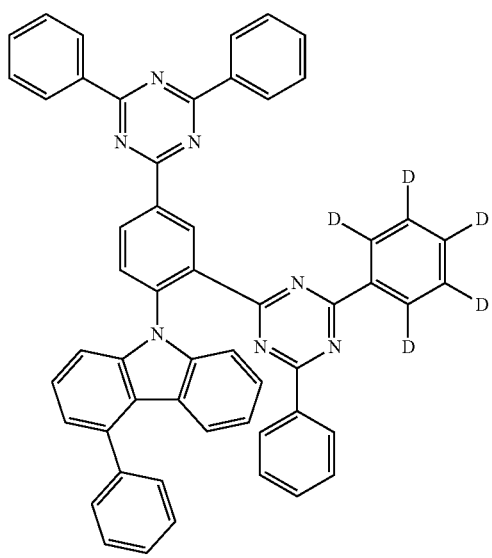

Compound 5

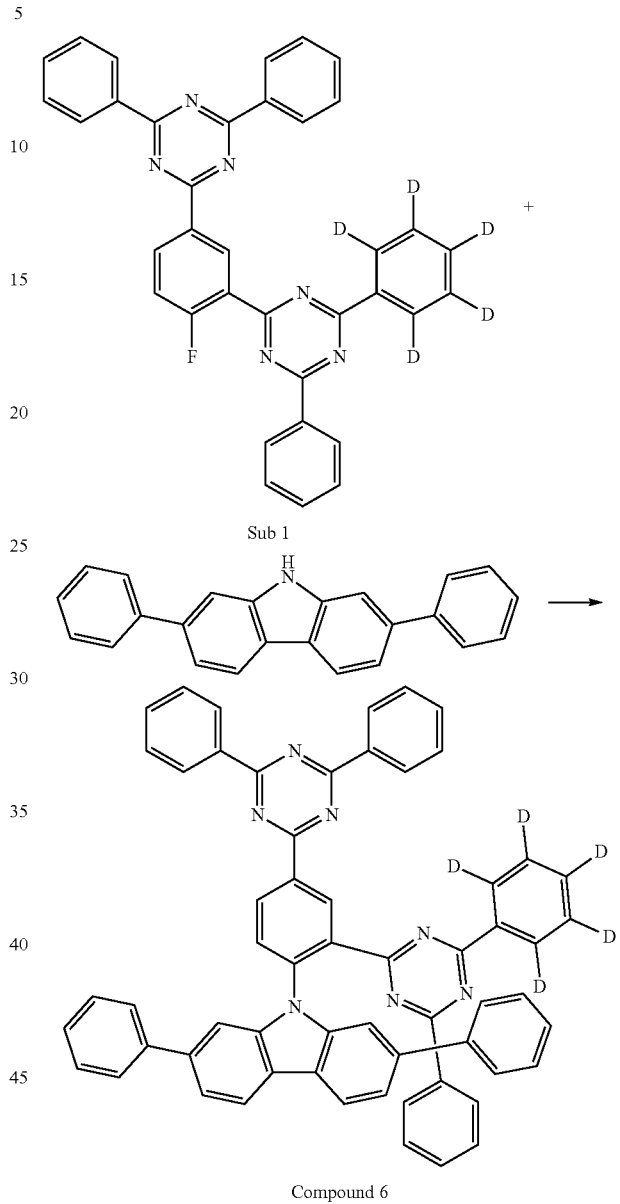

Compound sub 1 (10 g, 17.8 mmol) and 4-pheny-9H-carbazole (12.4 g, 17.8 mmol) were added to 200 ml of dimethylformamide under a nitrogen atmosphere, and the mixture was stirred and refluxed. Then, sodium tert-butoxide (11.3 g, 53.3 mmol) was added thereto and sufficiently stirred, and then bis(tri-tert-butylphosphine)palladium (0.3 g, 0.5 mmol) was added. After reacting for 5 hours, the reaction mixture was cooled to room temperature and then the organic layer was subjected to filtration treatment to remove a salt, and then the filtered organic layer was distilled. This was added again to 160 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 5 (11.5 g, yield: 72%, MS: [M+H]+=901).

Compound sub 1 (10 g, 17.8 mmol) and 2,7-dipheny-9H-carbazole (5.7 g, 17.8 mmol) were added to 200 ml of dimethylformamide under a nitrogen atmosphere, and the mixture was stirred and refluxed. Then, sodium tert-butoxide (11.3 g, 53.3 mmol) was added thereto and sufficiently stirred, and then bis(tri-tert-butylphosphine)palladium (0.3 g, 0.5 mmol) was added. After reacting for 3 hours, the reaction mixture was cooled to room temperature and then the organic layer was subjected to filtration treatment to remove a salt, and then the filtered organic layer was distilled. This was added again to 153 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 6 (11.6 g, yield: 76%, MS: [M+H]+=863.4).

Preparation Example 13: Preparation of Compound 7

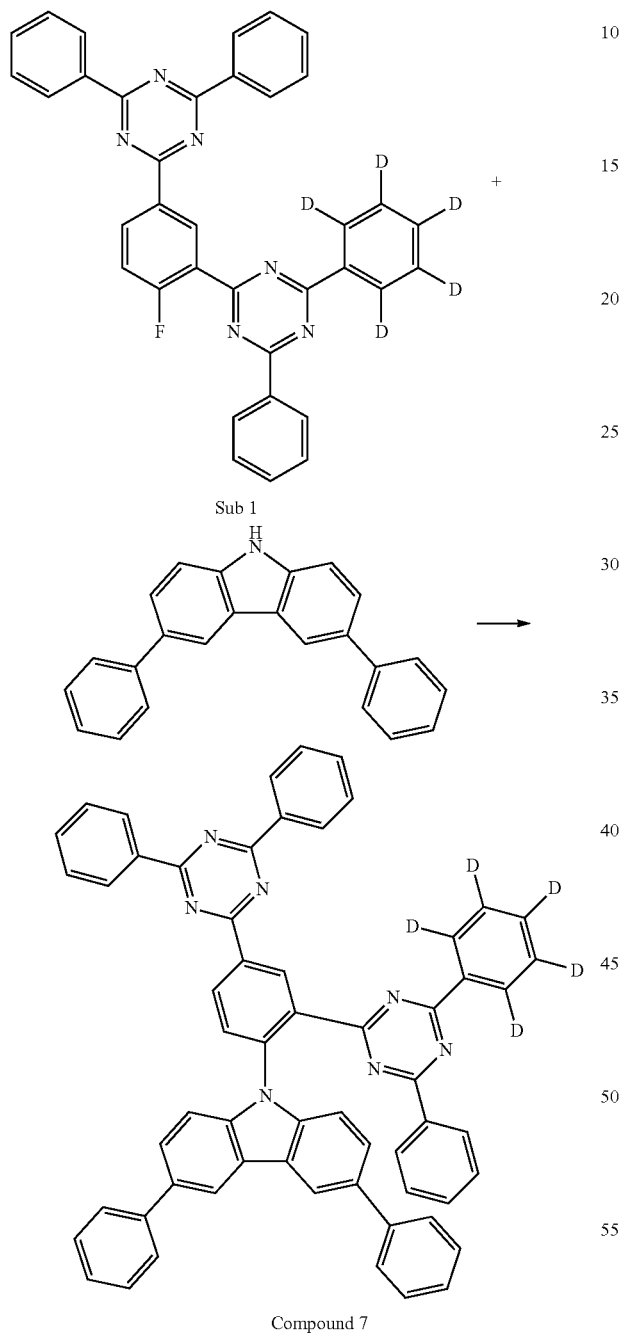

Compound 7

Compound sub 1 (10 g, 17.8 mmol) and 3,6-dipheny-9H-carbazole (5.7 g, 17.8 mmol) were added to 200 ml of dimethylformamide under a nitrogen atmosphere, and the mixture was stirred and refluxed. Then, sodium tert-butoxide (11.3 g, 53.3 mmol) was added thereto and sufficiently stirred, and then bis(tri-tert-butylphosphine)palladium (0.3 g, 0.5 mmol) was added. After reacting for 3 hours, the reaction mixture was cooled to room temperature and then the organic layer was subjected to filtration treatment to remove a salt, and then the filtered organic layer was distilled. This was added again to 153 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 7 (10.9 g, yield: 71%, MS: [M+H]+=863.4).

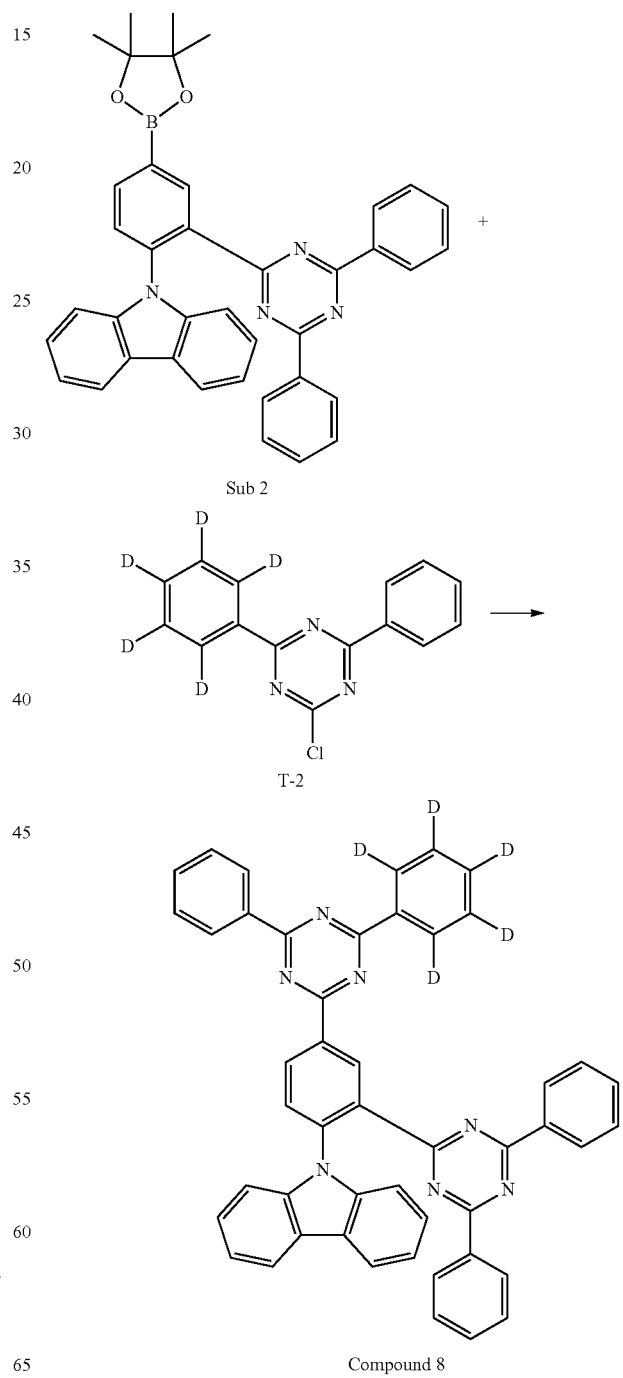

Compound 8

Compound sub 2 (50 g, 83.3 mmol) and Compound T-2 (22.7 g, 83.3 mmol) were added to 1000 ml of tetrahydrofuran under a nitrogen atmosphere, and the mixture was stirred and refluxed. Then, potassium carbonate (34.5 g, 249.9 mmol) was dissolved in 35 ml of water, added thereto and sufficiently stirred, and then tetrakistriphenyl-phosphinopalladium (2.9 g, 2.5 mmol) was added. After reacting for 3 hours, the reaction mixture was cooled to room temperature, the organic layer and the aqueous layer were separated, and then the organic layer was distilled. This was added again to 1183 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound 8 (39.6 g, yield: 67%, MS: [M+H]$^+$=711.3).

Preparation Example 15: Preparation of Compound 9

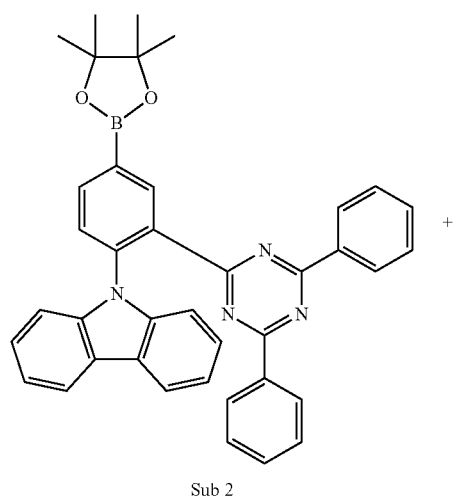

Sub 2

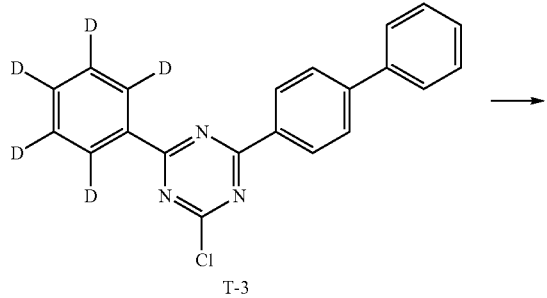

T-3

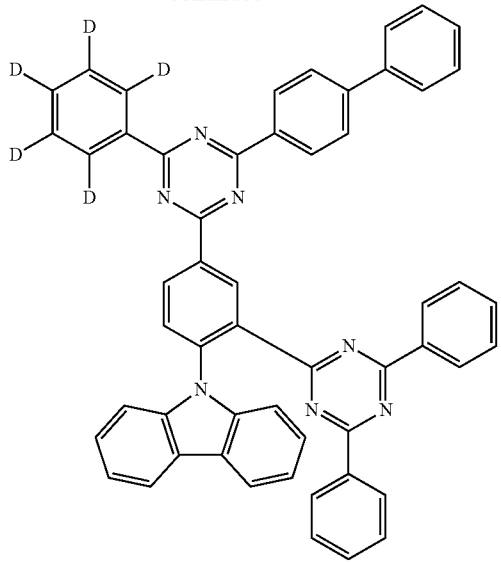

Ccompound 9

Compound sub 2 (50 g, 83.3 mmol) and Compound T-3 (29 g, 83.3 mmol) were added to 1000 ml of tetrahydrofuran under a nitrogen atmosphere, and the mixture was stirred and refluxed. Then, potassium carbonate (34.5 g, 249.9 mmol) was dissolved in 35 ml of water, added thereto and sufficiently stirred, and then tetrakistriphenyl-phosphinopalladium (2.9 g, 2.5 mmol) was added. After reacting for 3 hours, the reaction mixture was cooled to room temperature, the organic layer and the aqueous layer were separated, and then the organic layer was distilled. This was added again to 1310 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound 9 (43.2 g, yield: 66%, MS: [M+H]$^+$=787.3).

Preparation Example 16: Preparation of Compound 10

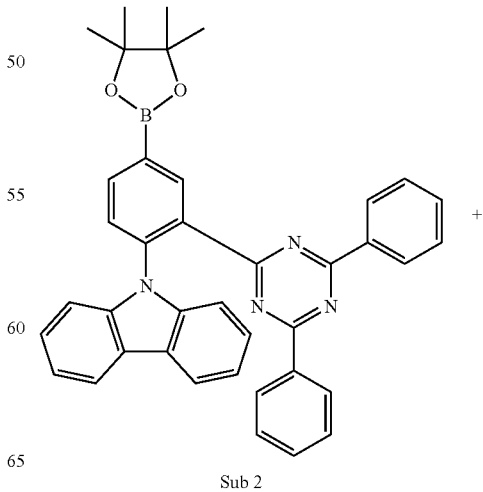

Sub 2

Preparation Example 17: Preparation of Compound 11

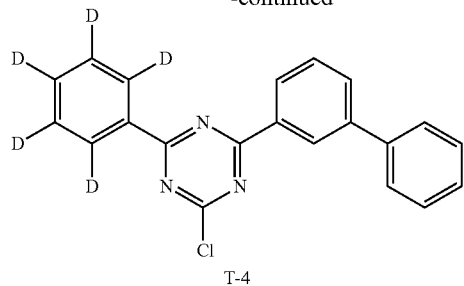
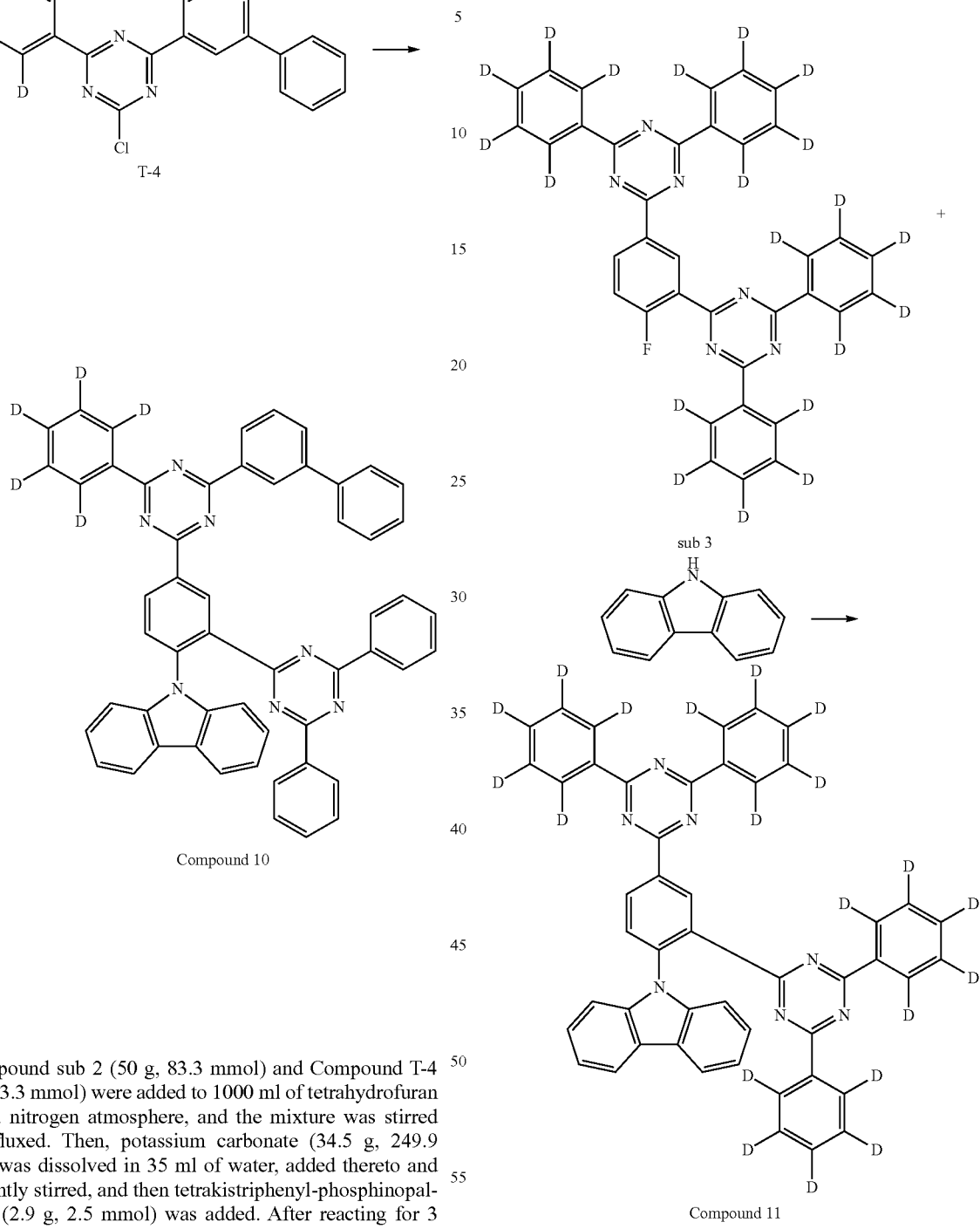

Compound sub 2 (50 g, 83.3 mmol) and Compound T-4 (29 g, 83.3 mmol) were added to 1000 ml of tetrahydrofuran under a nitrogen atmosphere, and the mixture was stirred and refluxed. Then, potassium carbonate (34.5 g, 249.9 mmol) was dissolved in 35 ml of water, added thereto and sufficiently stirred, and then tetrakistriphenyl-phosphinopalladium (2.9 g, 2.5 mmol) was added. After reacting for 3 hours, the reaction mixture was cooled to room temperature, the organic layer and the aqueous layer were separated, and then the organic layer was distilled. This was added again to 1310 ml of chloroform, dissolved and washed twice with water. The organic layer was then separated, anhydrous magnesium sulfate was added thereto, stirred, and then filtered. The filtrate was distilled under reduced pressure. The concentrated compound was purified by a silica column using chloroform and ethyl acetate to give a white solid compound 10 (51.7 g, yield: 79%, MS: [M+H]$^+$=787.3).

Compound sub 3 (10 g, 17.3 mmol) and 9H-carbazole (2.9 g, 17.3 mmol) were added to 200 ml of dimethylformamide under a nitrogen atmosphere, and the mixture was stirred and refluxed. Then, sodium tert-butoxide (11 g, 51.9 mmol) was added thereto and sufficiently stirred, and then bis(tri-tert-butylphosphine)palladium (0.3 g, 0.5 mmol) was added. After reacting for 6 hours, the reaction mixture was cooled to room temperature and then the organic layer was subjected to filtration treatment to remove a salt, and then the filtered organic layer was distilled. This was added again to 149 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 11 (7.6 g, yield: 51%, MS: [M+H]+=863.4).

Preparation Example 18: Preparation of Compound 12

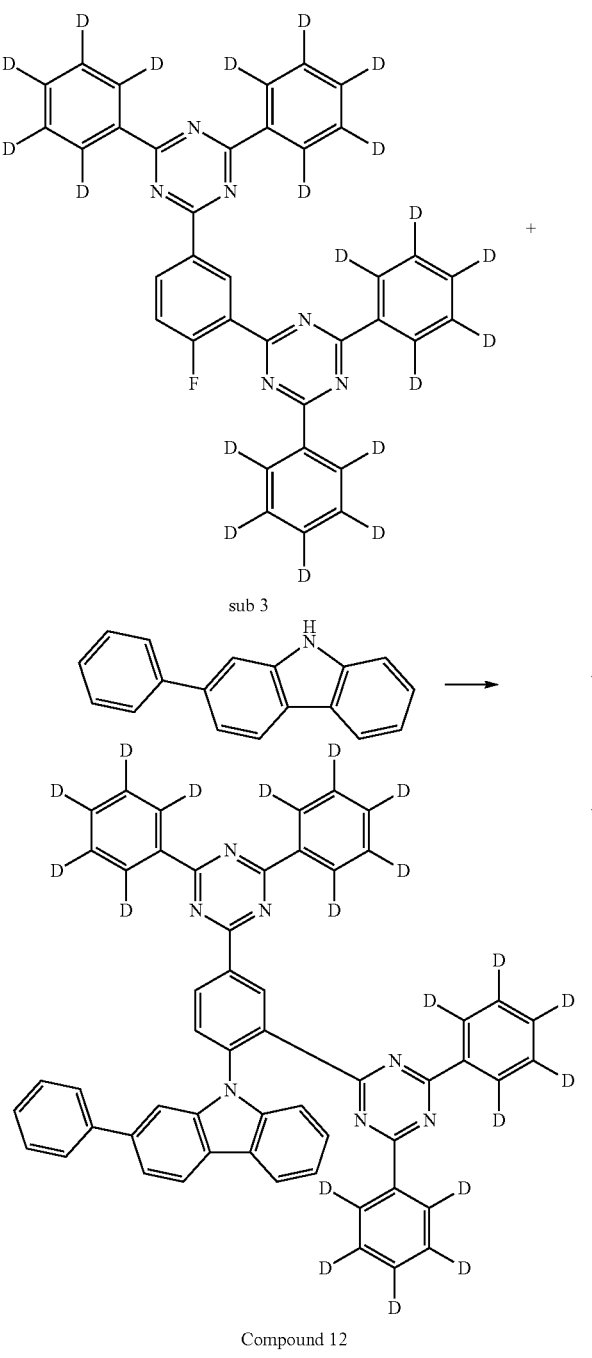

Compound sub 3 (10 g, 17.3 mmol) and 2-phenyl-9H-carbazole (4.2 g, 17.3 mmol) were added to 200 ml of dimethylformamide under a nitrogen atmosphere, and the mixture was stirred and refluxed. Then, sodium tert-butoxide (11 g, 51.9 mmol) was added thereto and sufficiently stirred, and then bis(tri-tert-butylphosphine)palladium (0.3 g, 0.5 mmol) was added. After reacting for 5 hours, the reaction mixture was coaled to roam temperature and then the organic layer was subjected to filtration treatment to remove a salt, and then the filtered organic layer was distilled. This was added again to 139 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 12 (7.8 g, yield: 56%, MS: [M+H]+=802.4).

Preparation Example 19: Preparation of Compound 13

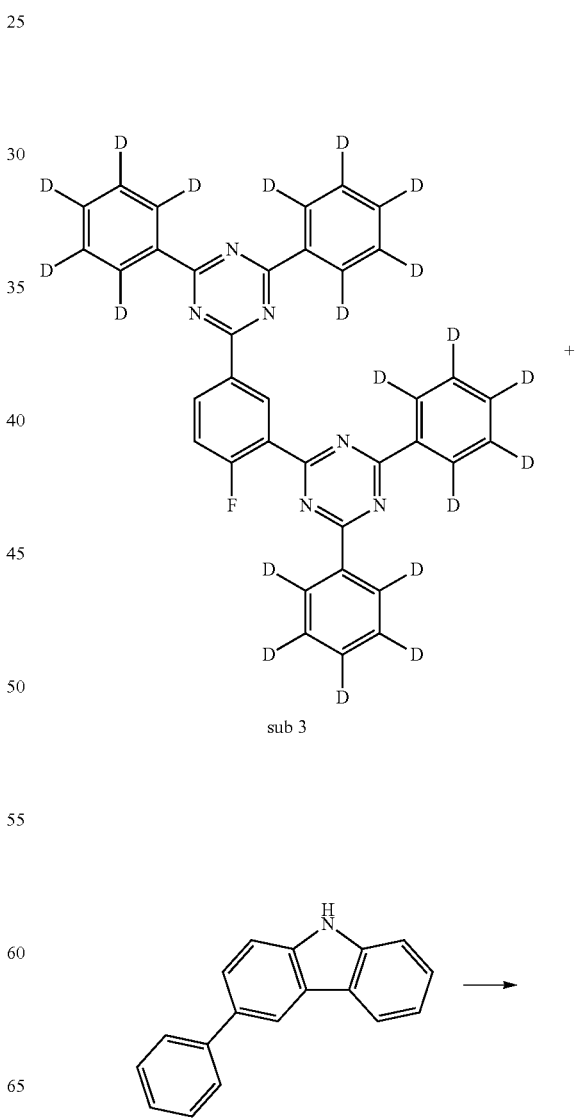

Preparation Example 20: Preparation of Compound 14

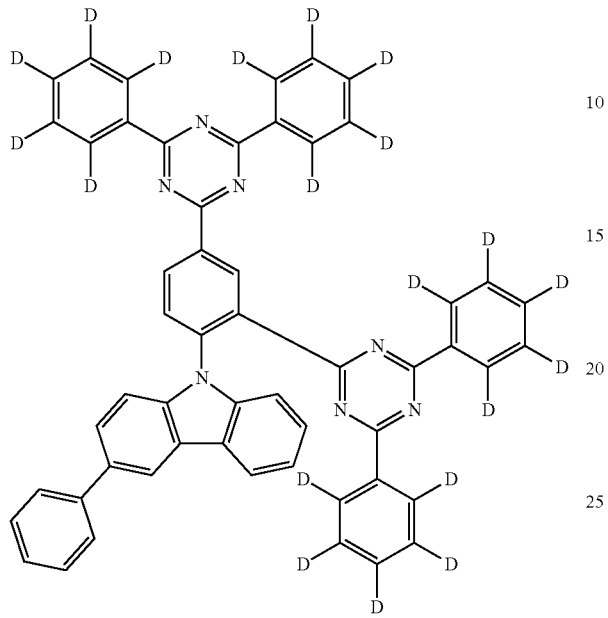

Compound 13

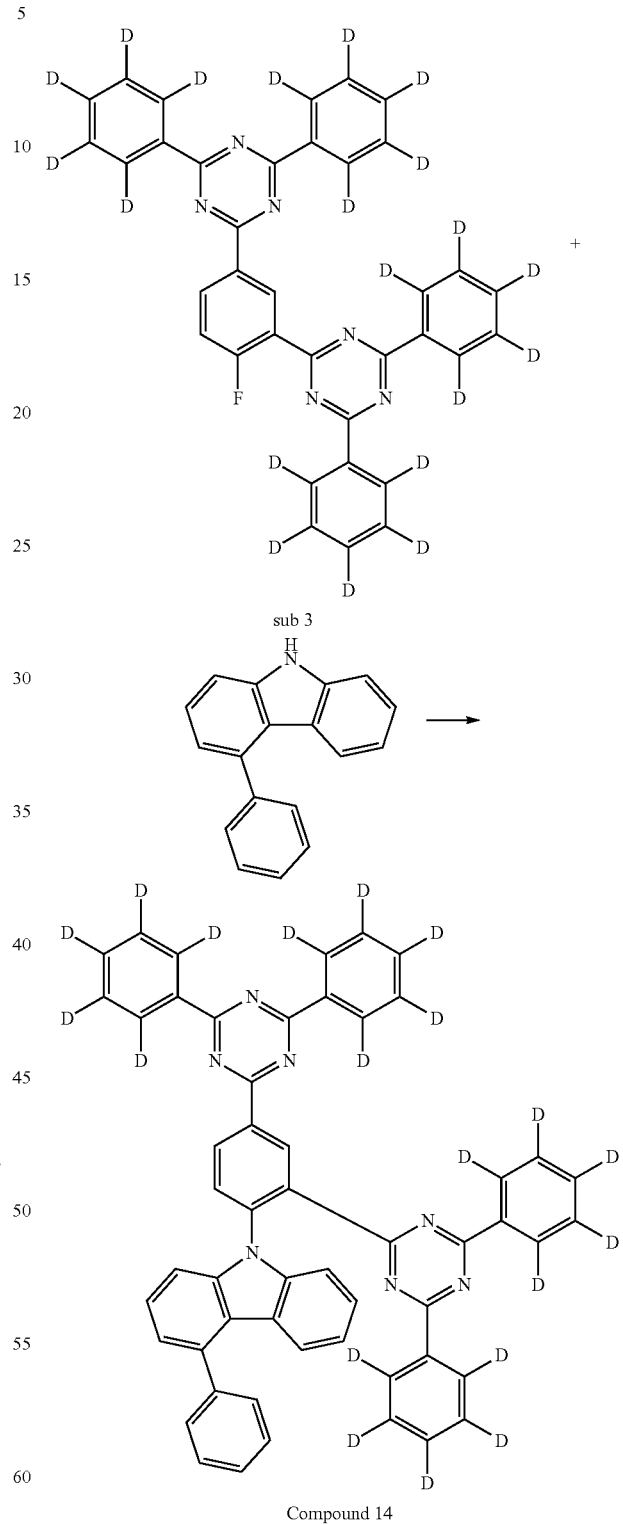

Compound sub 3 (10 g, 17.3 mmol) and 3-phenyl-9H-carbazole (4.2 g, 17.3 mmol) were added to 200 ml of dimethylformamide under a nitrogen atmosphere, and the mixture was stirred and refluxed. Then, sodium tert-butoxide (11 g, 51.9 mmol) was added thereto and sufficiently stirred, and then bis(tri-tert-butylphosphine)palladium (0.3 g, 0.5 mmol) was added. After reacting for 7 hours, the reaction mixture was cooled to room temperature and then the organic layer was subjected to filtration treatment to remove a salt, and then the filtered organic layer was distilled. This was added again to 139 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 13 (10.4 g, yield: 75%, MS: [M+H]+=802.4).

Compound sub 3 (10 g, 17.3 mmol) and 4-phenyl-9H-carbazole (4.2 g, 17.3 mmol) were added to 200 ml of dimethylformamide under a nitrogen atmosphere, and the mixture was stirred and refluxed. Then, sodium tert-butoxide (11 g, 51.9 mmol) was added thereto and sufficiently stirred, and then bis(tri-tert-butylphosphine)palladium (0.3 g, 0.5 mmol) was added. After reacting for 6 hours, the reaction mixture was cooled to room temperature and then the organic layer was subjected to filtration treatment to remove a salt, and then the filtered organic layer was distilled. This was added again to 139 ml of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 14 (10.3 g, yield: 74%, MS: [M+H]+=802.4).

Preparation Example 21: Preparation of Compound 15

Compound sub 4 (10 g, 14.7 mmol) and 2-bromo-4,6-diphenylpyridine (4.5 g, 14.7 mmol) were added to 200 ml of tetrahydrofuran under a nitrogen atmosphere, and the mixture was stirred and refluxed. Then, potassium carbonate (6.1 g, 44 mmol) was dissolved in 6 ml of water, added thereto and sufficiently stirred, and then tetrakistrphenylphosphinopalladium (0.5 g, 0.4 mmol) was added. After reacting for 2 hours, the reaction mixture was cooled to room temperature, the organic layer and the aqueous layer were separated, and then the organic layer was distilled. This was added again to 230 ml of chloroform, dissolved and washed twice with water. The organic layer was then separated, anhydrous magnesium sulfate was added thereto, stirred, and then filtered. The filtrate was distilled under reduced pressure. The concentrated compound was recrystallized from chloroform and ethyl acetate to give a yellow solid compound 15 (8.9 g, yield: 77%, MS: [M+H]$^+$=785.3).

Preparation Example 22: Preparation of Compound 16

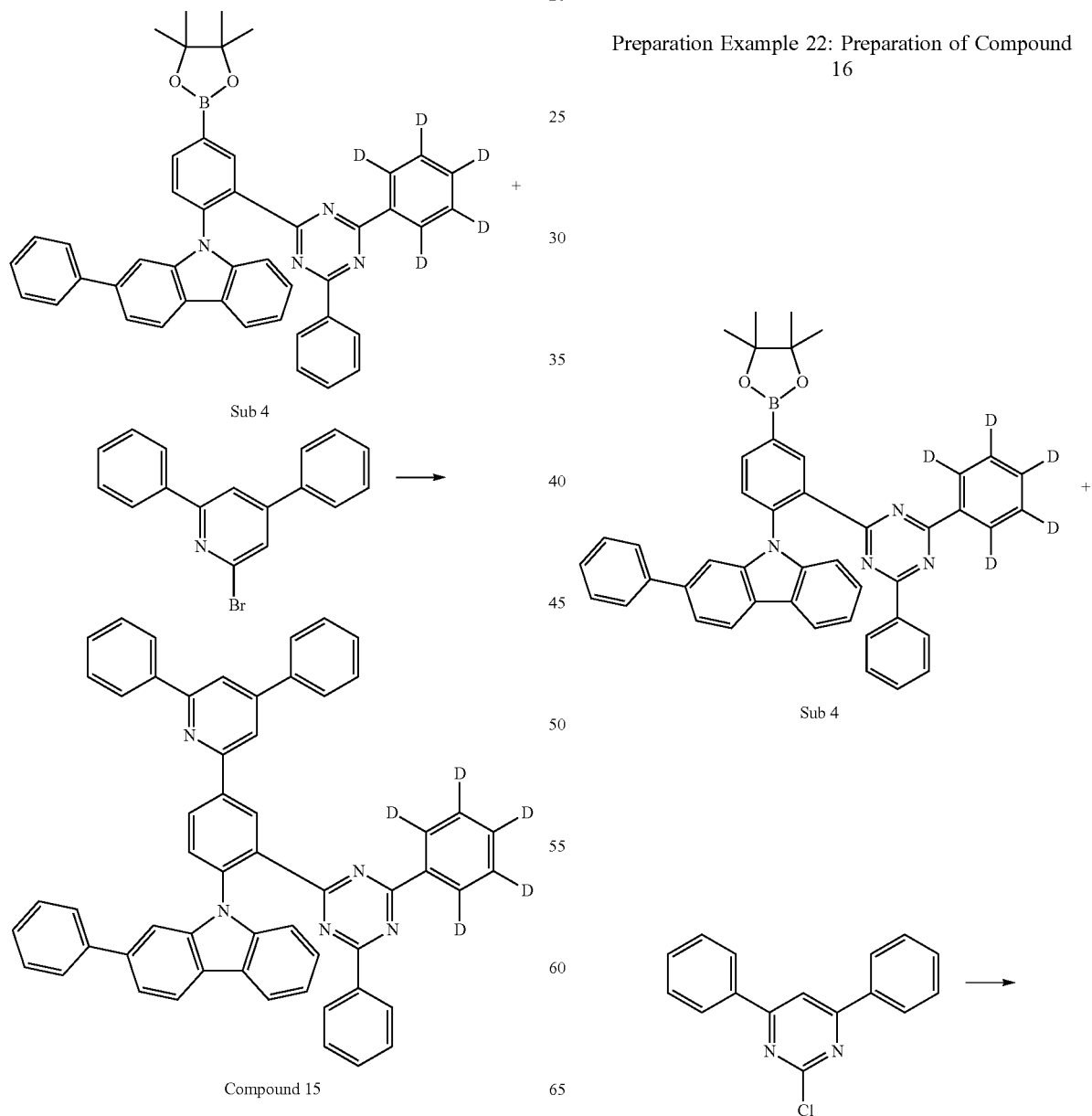

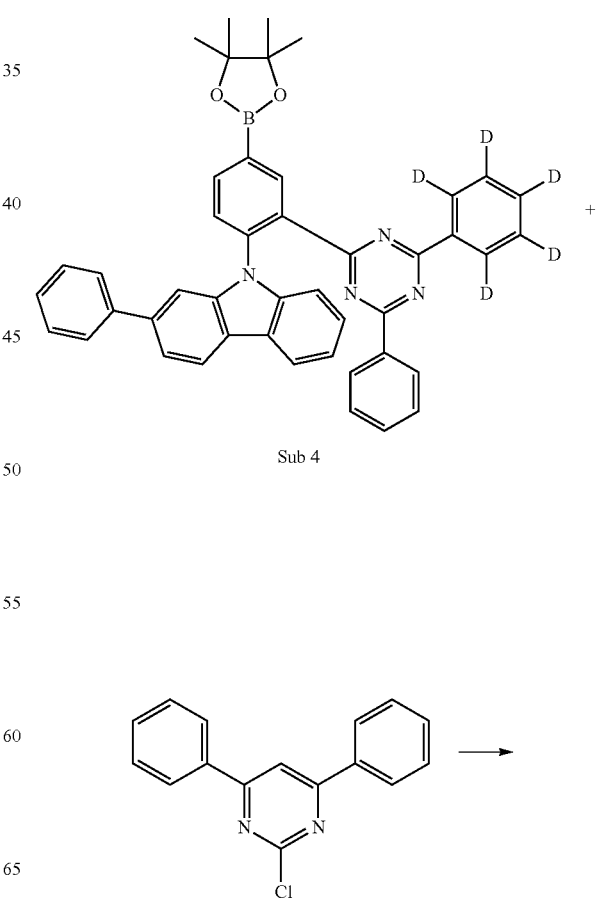

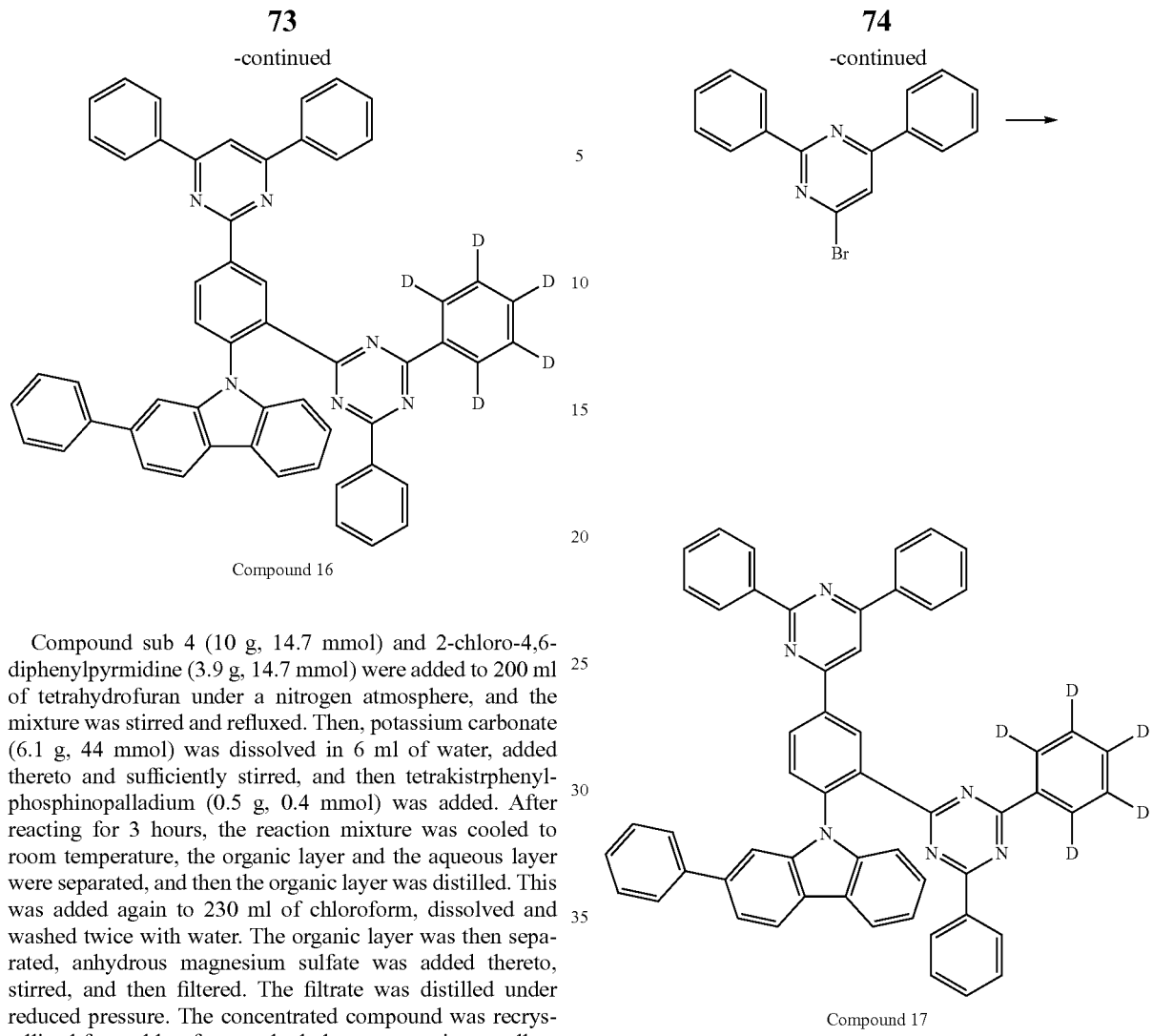

Compound 16

Compound sub 4 (10 g, 14.7 mmol) and 2-chloro-4,6-diphenylpyrmidine (3.9 g, 14.7 mmol) were added to 200 ml of tetrahydrofuran under a nitrogen atmosphere, and the mixture was stirred and refluxed. Then, potassium carbonate (6.1 g, 44 mmol) was dissolved in 6 ml of water, added thereto and sufficiently stirred, and then tetrakistrphenyl-phosphinopalladium (0.5 g, 0.4 mmol) was added. After reacting for 3 hours, the reaction mixture was cooled to room temperature, the organic layer and the aqueous layer were separated, and then the organic layer was distilled. This was added again to 230 ml of chloroform, dissolved and washed twice with water. The organic layer was then separated, anhydrous magnesium sulfate was added thereto, stirred, and then filtered. The filtrate was distilled under reduced pressure. The concentrated compound was recrystallized from chloroform and ethyl acetate to give a yellow solid compound 16 (8.5 g, yield: 74%, MS: [M+H]$^+$=786.3).

Preparation Example 23: Preparation of Compound 17

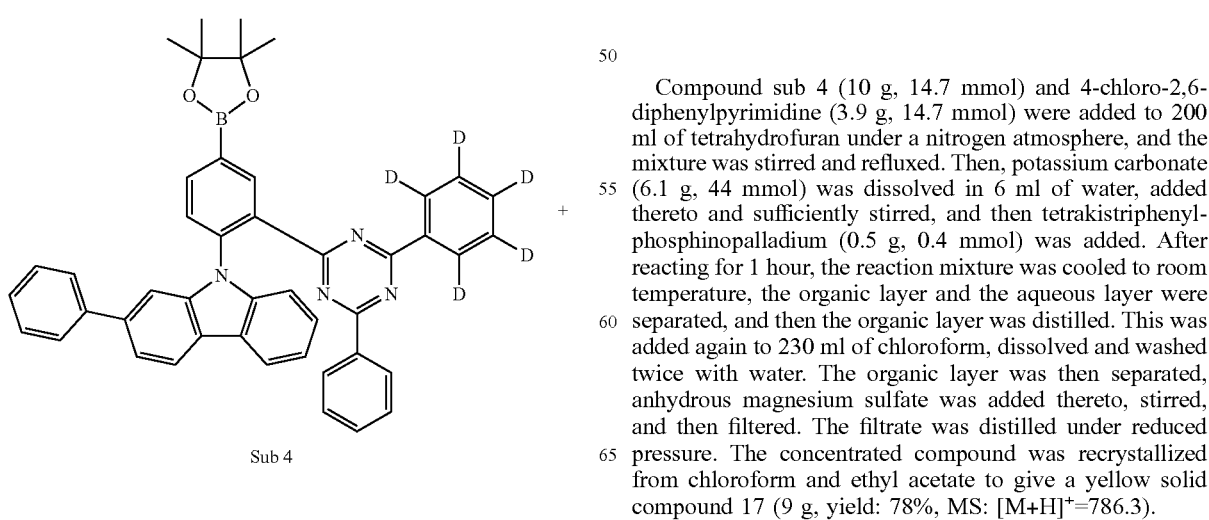

Compound 17

Compound sub 4 (10 g, 14.7 mmol) and 4-chloro-2,6-diphenylpyrimidine (3.9 g, 14.7 mmol) were added to 200 ml of tetrahydrofuran under a nitrogen atmosphere, and the mixture was stirred and refluxed. Then, potassium carbonate (6.1 g, 44 mmol) was dissolved in 6 ml of water, added thereto and sufficiently stirred, and then tetrakistriphenyl-phosphinopalladium (0.5 g, 0.4 mmol) was added. After reacting for 1 hour, the reaction mixture was cooled to room temperature, the organic layer and the aqueous layer were separated, and then the organic layer was distilled. This was added again to 230 ml of chloroform, dissolved and washed twice with water. The organic layer was then separated, anhydrous magnesium sulfate was added thereto, stirred, and then filtered. The filtrate was distilled under reduced pressure. The concentrated compound was recrystallized from chloroform and ethyl acetate to give a yellow solid compound 17 (9 g, yield: 78%, MS: [M+H]$^+$=786.3).

Preparation Example 24: Preparation of Compound 18

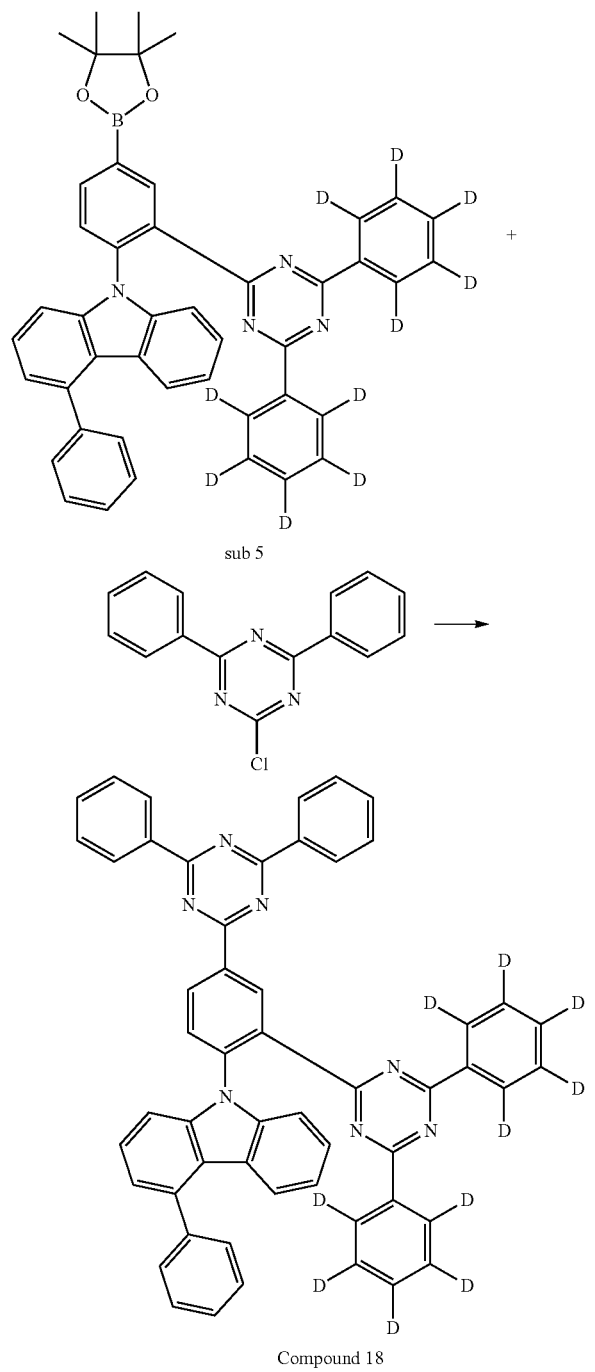

Compound sub 5 (10 g, 14.6 mmol) and 2-chloro-4,6-diphenyl-1,3,5-triazine (3.9 g, 14.6 mmol) were added to 200 ml of tetrahydrofuran under a nitrogen atmosphere, and the mixture was stirred and refluxed. Then, potassium carbonate (6 g, 43.7 mmol) was dissolved in 6 ml of water, added thereto and sufficiently stirred, and then tetrakistriphenyl-phosphinopalladium (0.5 g, 0.4 mmol) was added. After reacting for 3 hours, the reaction mixture was coaled to roam temperature, the organic layer and the aqueous layer were separated, and then the organic layer was distilled. This was added again to 231 ml of chloroform, dissolved and washed twice with water. The organic layer was then separated, anhydrous magnesium sulfate was added thereto, stirred, and then filtered. The filtrate was distilled under reduced pressure. The concentrated compound was recrystallized from chloroform and ethyl acetate to give a yellow solid compound 18 (8.5 g, yield: 74%, MS: $[M+H]^+$=792.4).

Preparation Example 25: Preparation of Compound 19

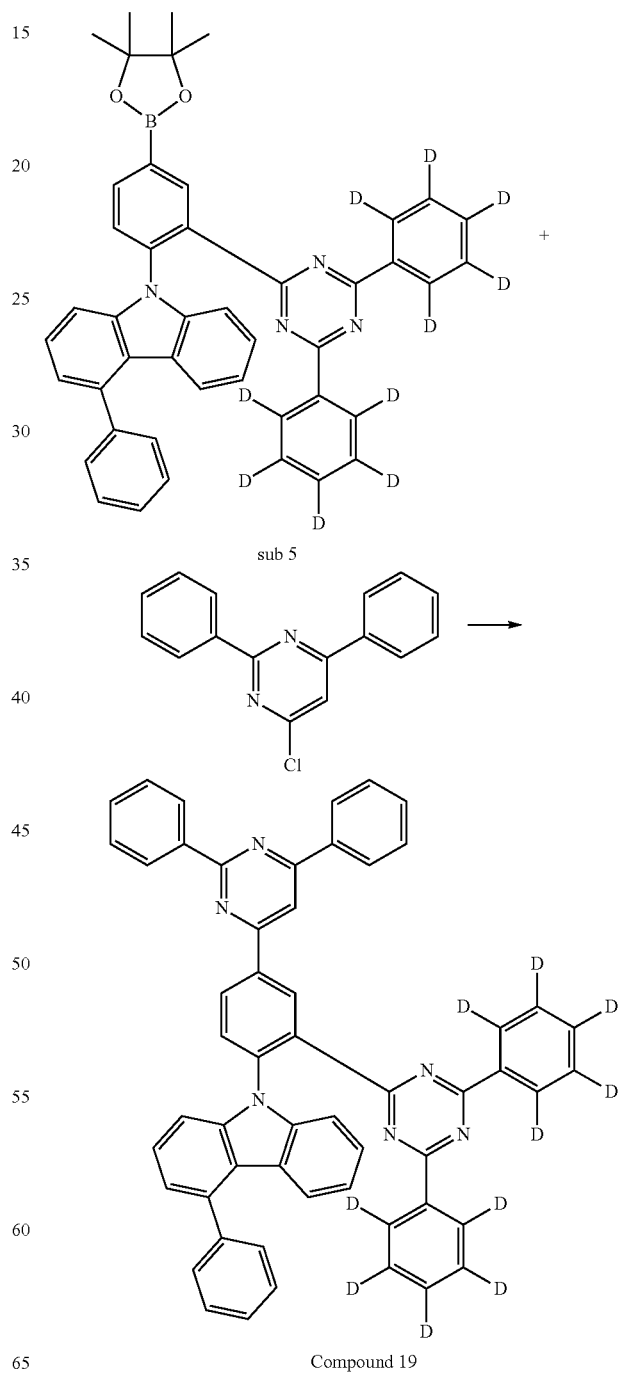

Compound sub 5 (10 g, 14.6 mmol) and 4-chloro-2,6-diphenylpyrimidine (3.9 g, 14.6 mmol) were added to 200 ml of tetrahydrofuran under a nitrogen atmosphere, and the mixture was stirred and refluxed. Then, potassium carbonate (6 g, 43.7 mmol) was dissolved in 6 ml of water, added thereto and sufficiently stirred, and then tetrakistrphenyl-phosphinopalladium (0.5 g, 0.4 mmol) was added. After reacting for 2 hours, the reaction mixture was cooled to room temperature, the organic layer and the aqueous layer were separated, and then the organic layer was distilled. This was added again to 230 ml of chloroform, dissolved and washed twice with water. The organic layer was then separated, anhydrous magnesium sulfate was added thereto, stirred, and then filtered. The filtrate was distilled under reduced pressure. The concentrated compound was recrystallized from chloroform and ethyl acetate to give a yellow solid compound 19 (8.6 g, yield: 75%, MS: [M+H]$^+$=791.4).

Preparation Example 26: Preparation of Compound 20

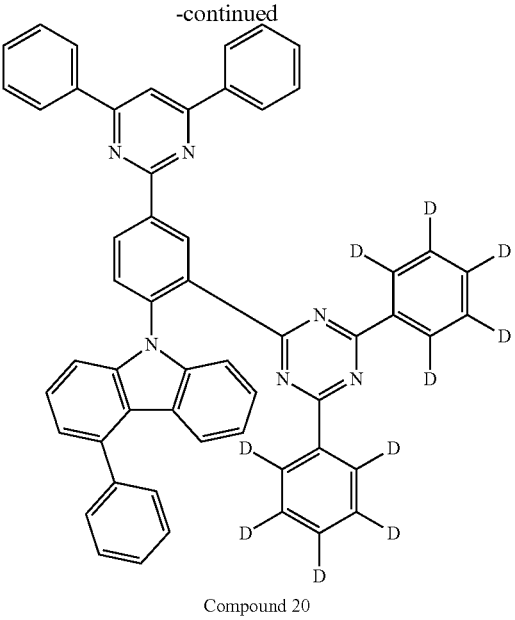

Compound 20

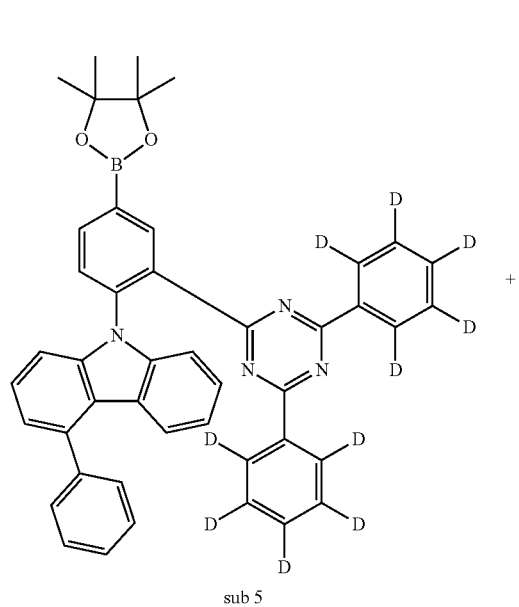

sub 5

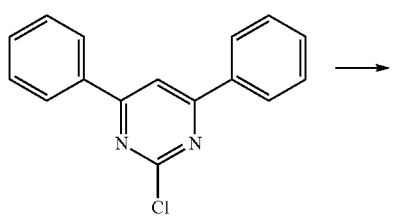

Compound sub 5 (10 g, 14.6 mmol) and 2-chloro-4,6-diphenylpyrimidine (3.9 g, 14.6 mmol) were added to 200 ml of tetrahydrofuran under a nitrogen atmosphere, and the mixture was stirred and refluxed. Then, potassium carbonate (6 g, 43.7 mmol) was dissolved in 6 ml of water, added thereto and sufficiently stirred, and then tetrakistrphenyl-phosphinopalladium (0.5 g, 0.4 mmol) was added. After reacting for 1 hour, the reaction mixture was cooled to room temperature, the organic layer and the aqueous layer were separated, and then the organic layer was distilled. This was added again to 230 ml of chloroform, dissolved and washed twice with water. The organic layer was then separated, anhydrous magnesium sulfate was added thereto, stirred, and then filtered. The filtrate was distilled under reduced pressure. The concentrated compound was recrystallized from chloroform and ethyl acetate to give a yellow solid compound 20 (9.2 g, yield: 80%, MS: [M+H]$^+$=791.4).

EXAMPLES

Example 1

A glass substrate on which ITO (indium tin oxide) was coated as a thin film to a thickness of 1,300 Å was put into distilled water in which a detergent was dissolved, and ultrasonically cleaned. A product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the ITO transparent electrode thus prepared, a compound HI-1 below was thermally vacuum-deposited to a thickness of 50 Å to form a hole injection layer. A compound HT-1 below was thermally vacuum-deposited to a thickness of 250 Å on the hole injection layer to form a hole transport layer, and a compound HT-2 below was vacuum-deposited to a thickness of 50 Å on the HT-1 deposited layer to form an electron blocking layer. Compound 1 prepared in the previous Preparation Example 7, a compound YGH-1 below and a phosphorescent dopant YGD-1 below were co-deposited in a weight ratio of 44:44:12 on the HT-2 deposited layer to form a light emitting layer with a thickness of 400 Å. A compound ET-1 below was vacuum-deposited to a thickness of 250 Å on the light emitting layer to form an electron transport layer, and a compound ET-2 below and Li were vacuum-deposited in a weight ratio of 98:2 on the electron transport layer to form an electron injection layer with a thickness of 100 Å. Aluminum was deposited to a thickness of 1000 Å on the electron injection layer to form a cathode.

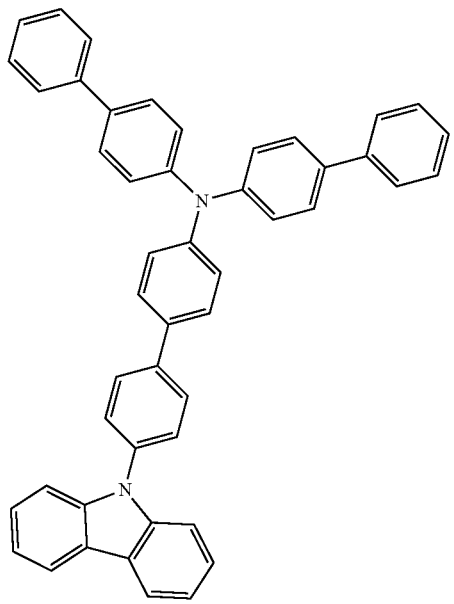

HT-2

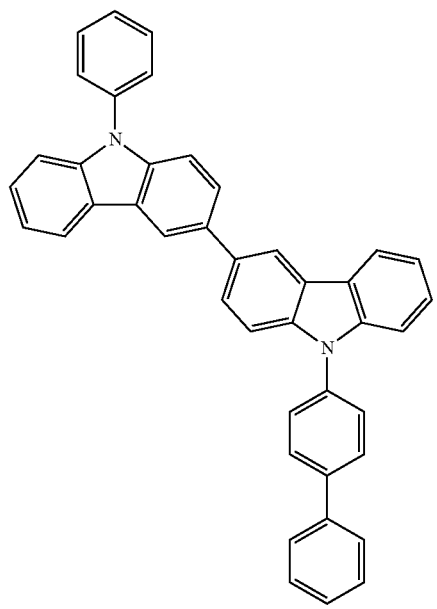

YGH-1

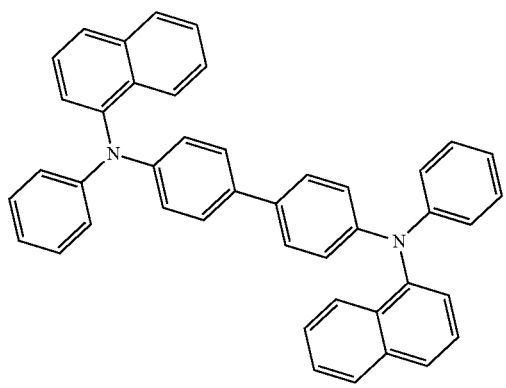

HI-1

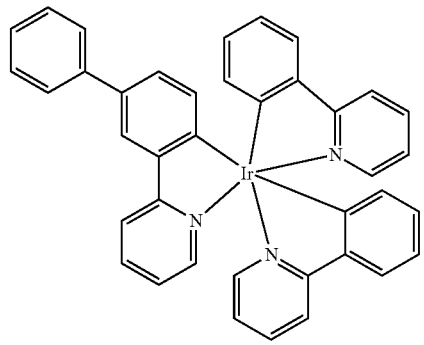

HT-1

YGD-1

-continued

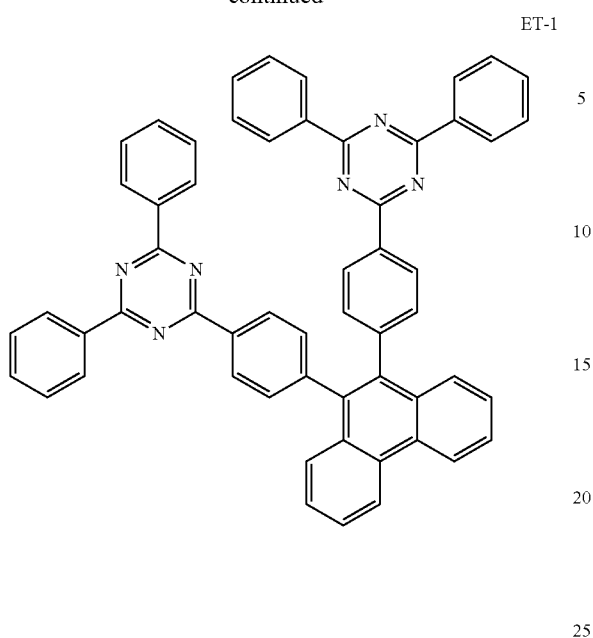

ET-1

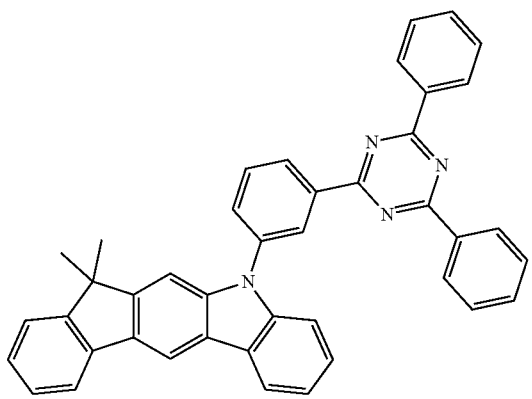

CE1

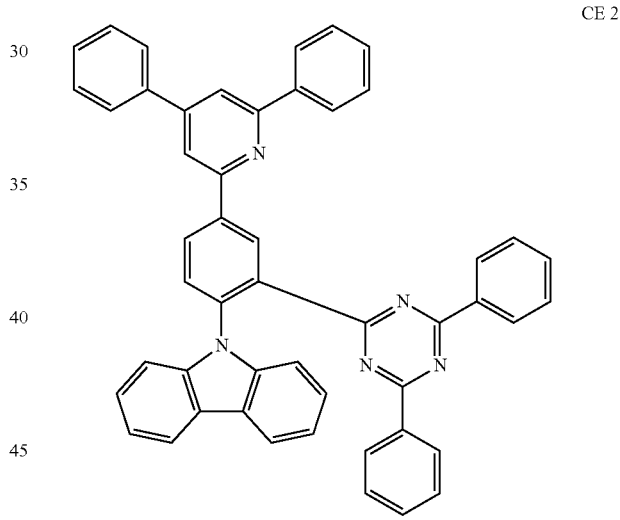

CE 2

ET-2

In the above-mentioned process, the vapor deposition rate of the organic material was maintained at 0.4 to 0.7 Å/sec, the deposition rate of aluminum was maintained at 2 Å/sec, and the degree of vacuum during the deposition was maintained at $1 \times 10^{-7}$ to $5 \times 10^{-8}$ torr.

Examples 2 to 20

The organic light emitting devices were manufactured in the same manner as in Example 1, except that the compounds shown in Table 1 below were used instead of Compound 1 of Preparation Example 7 in Example 1.

Comparative Examples 1 and 2

The organic light emitting devices were manufactured in the same manner as in Example 1, except that the compounds shown in Table 1 below were used instead of Compound 1 of Preparation Example 7 in Example 1. In Table 1, the compounds CE1 and CE2 are as follows.

Experimental Example

The voltage and efficiency of the organic light emitting devices manufactured in Examples and Comparative Examples were measured at a current density of 10 mA/cm², and the lifetime was measured at a current density of 50 mA/cm². The results are shown in Table 1 below. At this time, $LT_{95}$ means the time required for the luminance to be reduced to 95% of the initial luminance.

TABLE 1

| | Compound | Voltage (V) (@10 mA/cm$^2$) | Efficiency (Cd/A) (@10 mA/cm$^2$) | Color coordinate (x, y) | Lifetime(hr) (LT$_{95}$ @50 mA/cm$^2$) |
|---|---|---|---|---|---|
| Example 1 | Compound 1 | 4.4 | 85 | 0.44, 0.51 | 165 |
| Example 2 | Compound 2 | 4.4 | 87 | 0.46, 0.53 | 183 |
| Example 3 | Compound 3 | 4.4 | 88 | 0.46, 0.54 | 189 |
| Example 4 | Compound 4 | 4.4 | 89 | 0.46, 0.54 | 199 |
| Example 5 | Compound 5 | 4.4 | 86 | 0.46, 0.53 | 225 |
| Example 6 | Compound 6 | 4.3 | 85 | 0.46, 0.53 | 189 |
| Example 7 | Compound 7 | 4.4 | 89 | 0.46, 0.54 | 219 |
| Example 8 | Compound 8 | 4.5 | 85 | 0.46, 0.54 | 160 |
| Example 9 | Compound 9 | 4.4 | 86 | 0.44, 0.51 | 173 |
| Example 10 | Compound 10 | 4.4 | 87 | 0.44, 0.51 | 180 |
| Example 11 | Compound 11 | 4.4 | 85 | 0.46, 0.53 | 181 |
| Example 12 | Compound 12 | 4.4 | 88 | 0.46, 0.54 | 220 |
| Example 13 | Compound 13 | 4.4 | 89 | 0.46, 0.54 | 235 |
| Example 14 | Compound 14 | 4.4 | 86 | 0.46, 0.53 | 261 |
| Example 15 | Compound 15 | 4.4 | 82 | 0.46, 0.53 | 129 |
| Example 16 | Compound 16 | 4.4 | 84 | 0.46, 0.54 | 145 |
| Example 17 | Compound 17 | 4.3 | 88 | 0.46, 0.54 | 100 |
| Example 18 | Compound 18 | 4.5 | 87 | 0.46, 0.54 | 250 |
| Example 19 | Compound 19 | 4.5 | 84 | 0.46, 0.54 | 160 |
| Example 20 | Compound 20 | 4.5 | 88 | 0.46, 0.54 | 115 |
| Comparative Example 1 | CE1 | 4.6 | 74 | 0.46, 0.54 | 45 |
| Comparative Example 2 | CE2 | 4.4 | 82 | 0.46, 0.55 | 92 |

As shown in Table above, when the compound of the present disclosure was used as a light emitting layer material, it was confirmed that it exhibited excellent efficiency and lifetime as compared with Comparative Examples. This is considered to be because deuterium was further substituted for the derivative, and thereby the orbital stability for electron transport in molecules was increased.

On the other hand, when comparing Examples to 4 and Example 5, or Examples 11 to 13 and Example 14, it was confirmed that in the case of the organic light emitting device including, as a host, a compound having a substituent at position 4 of parent carbazole, lifetime characteristics are significantly increased. From this, it can be inferred that when the position 4 of the carbazole is substituted, the orbital stability is significantly increased and the lifetime characteristic is increased.

EXPLANATION OF THE SYMBOLS

1: substrate
2: anode
3: light emitting layer
4: cathode
5: hole injection layer
6: hole transport layer
7: electron blocking layer
8: electron transport layer
9: electron injection layer

The invention claimed is:
1. A compound of any one of Chemical Formulae 1-2 to 1-7:

Chemical Formula 1-2

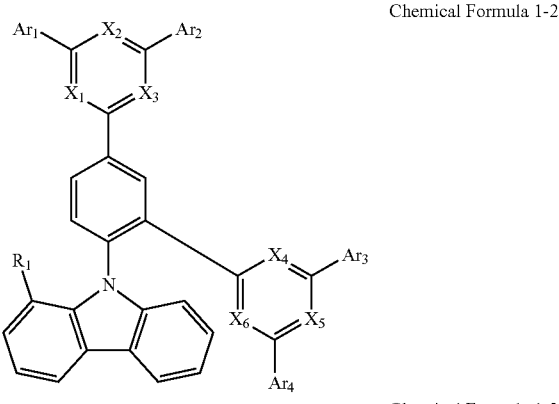

Chemical Formula 1-3

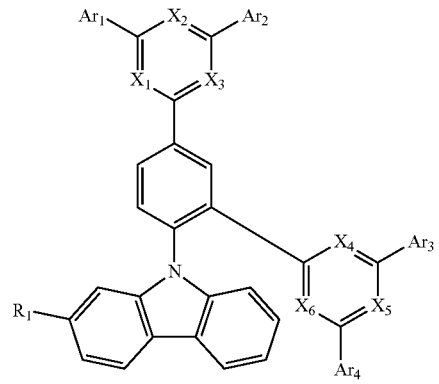

Chemical Formula 1-4

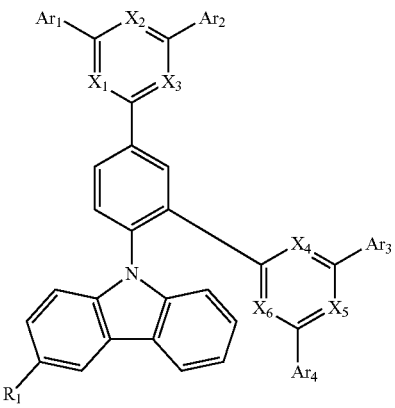

Chemical Formula 1-5

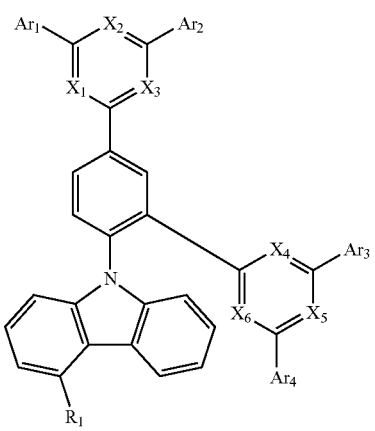

Chemical Formula 1-6

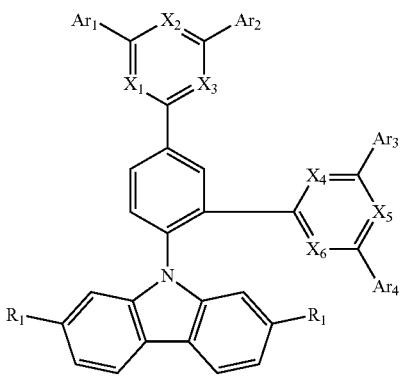

Chemical Formula 1-7

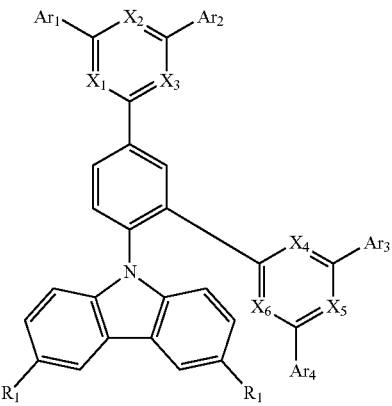

wherein, in Chemical Formulae 1-2 to 1-7:

$X_1$ to $X_6$ are each N;

$Ar_1$ to $Ar_4$ are each independently a phenyl, biphenylyl, or phenyl substituted with five deuterium, with the proviso that at least one of $Ar_1$ to $Ar_4$ is a phenyl substituted with five deuterium; and $R_1$ is phenyl.

2. The compound of claim 1, wherein $Ar_1$ to $Ar_4$ are each independently a phenyl or phenyl substituted with five deuteriums, with the proviso that at least one of $Ar_1$ to $Ar_4$ is phenyl substituted with five deuteriums.

3. The compound of claim 1, wherein the compound is any one compound selected from the group consisting of the following compounds:

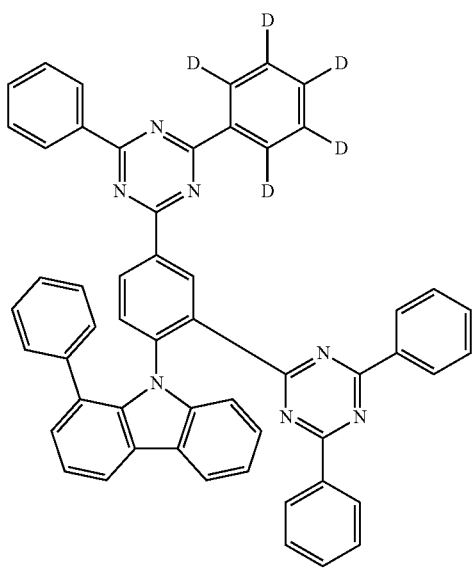

87
-continued
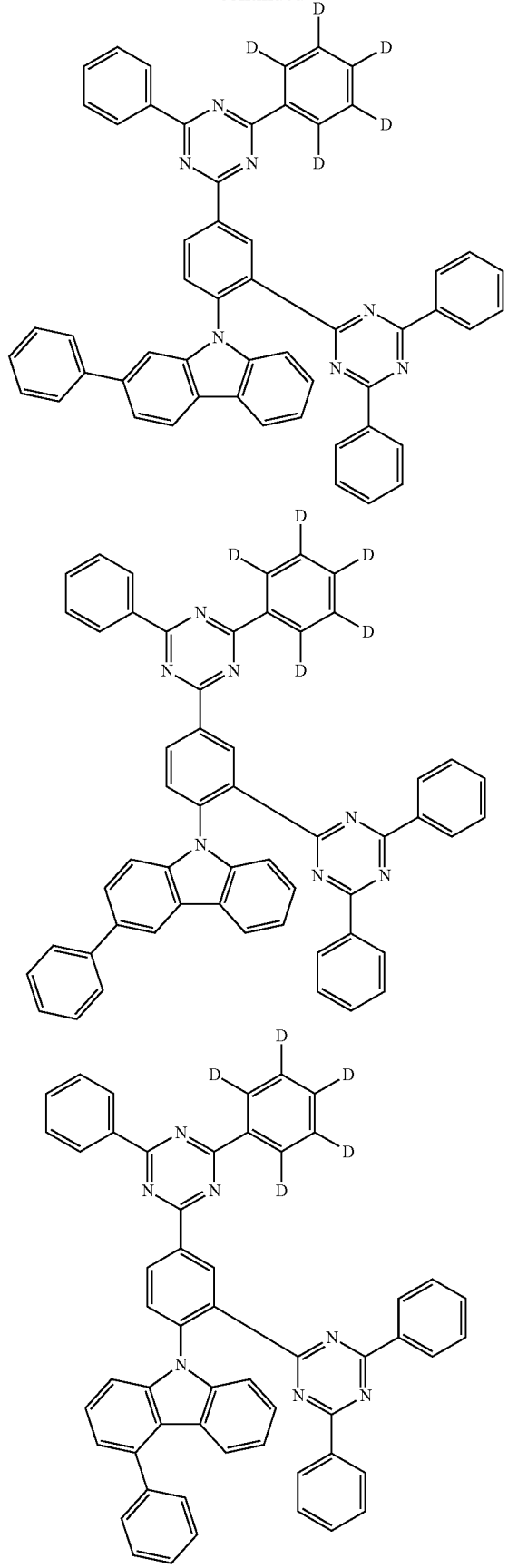
88
-continued
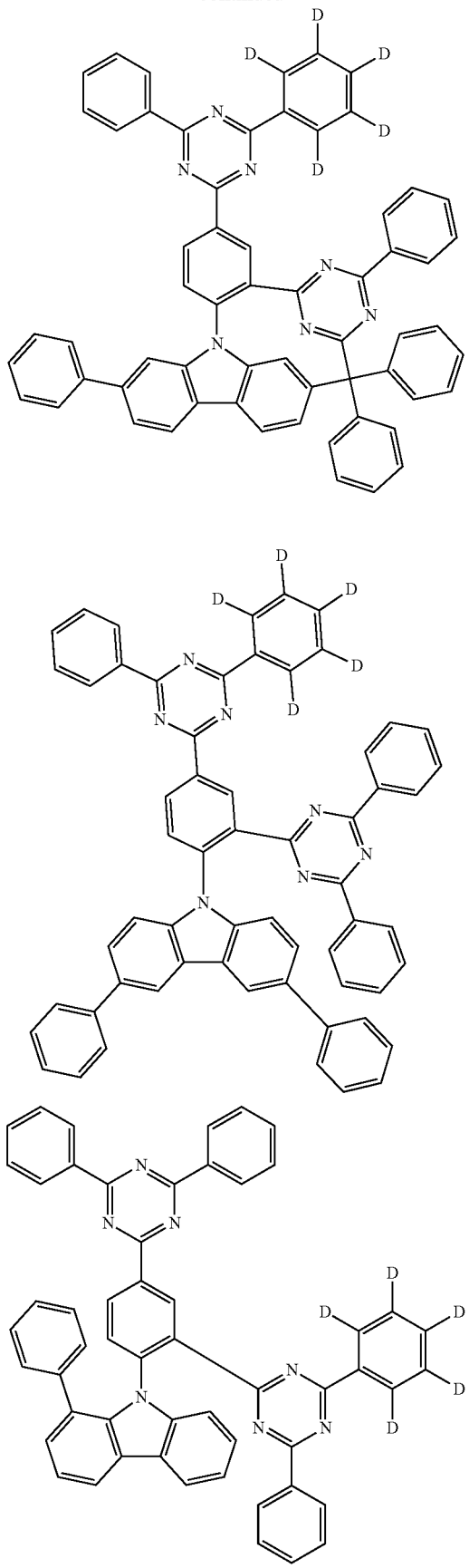

89
-continued
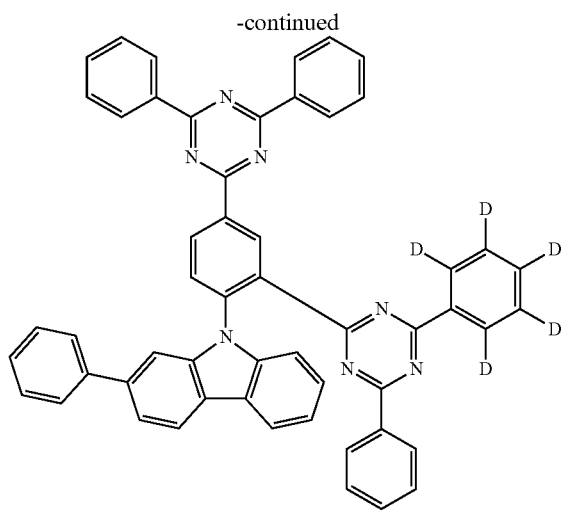
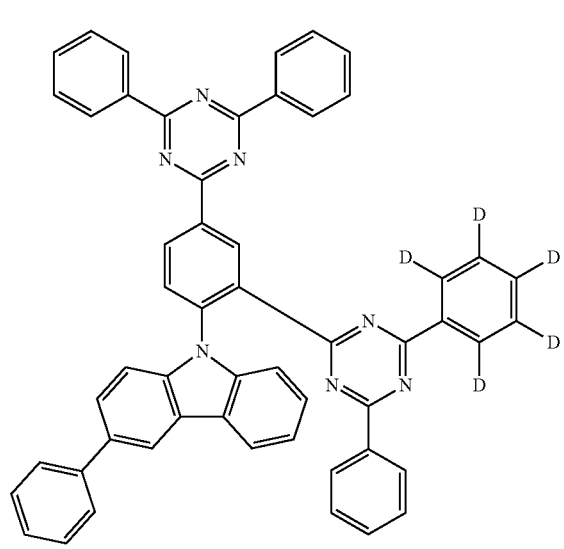
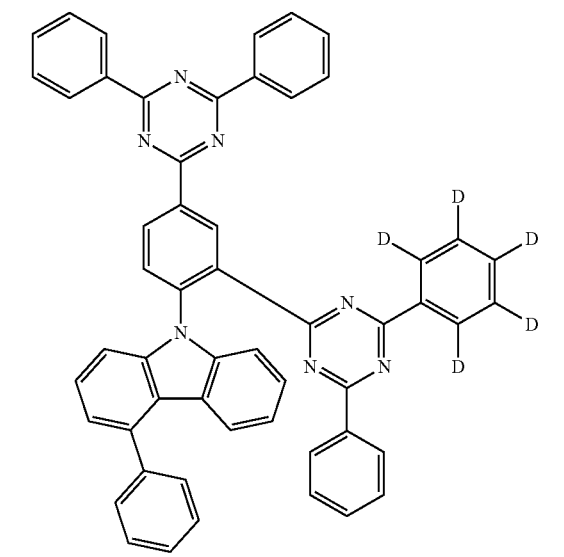
90
-continued
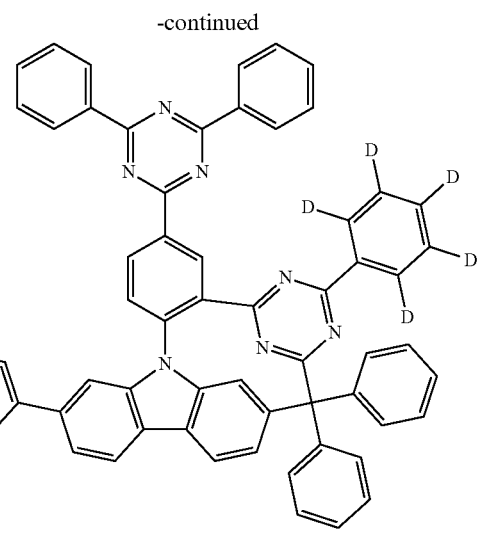
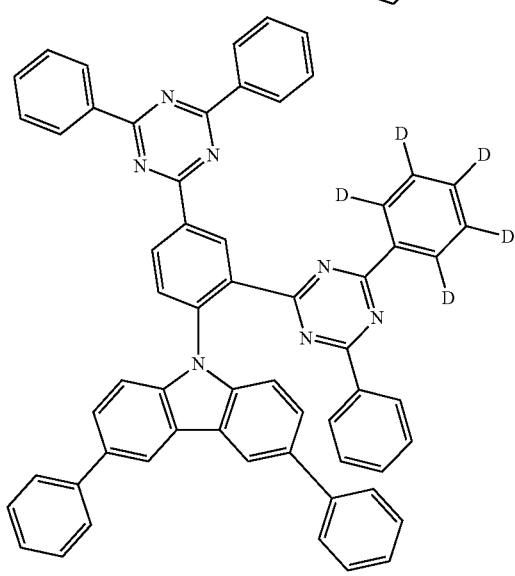
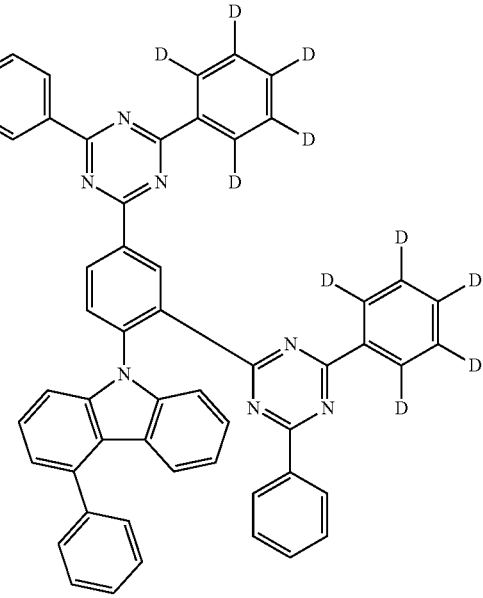

91
-continued
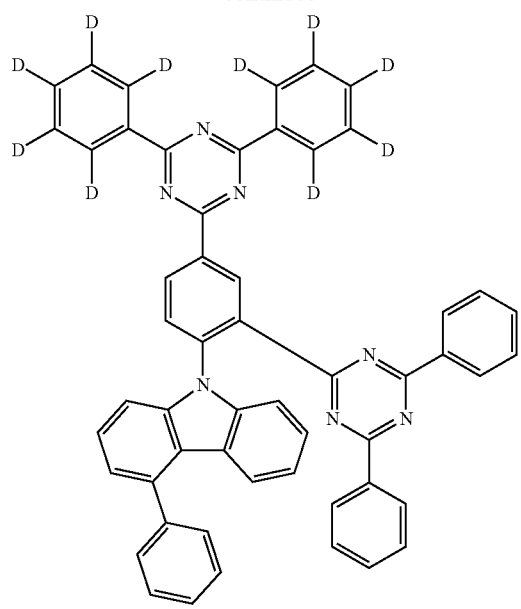
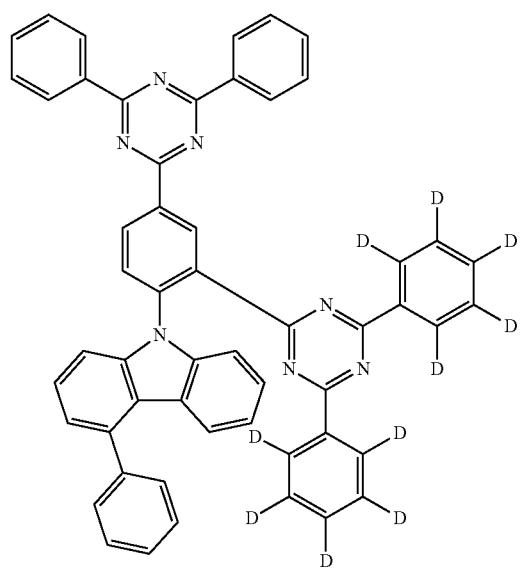
92
-continued
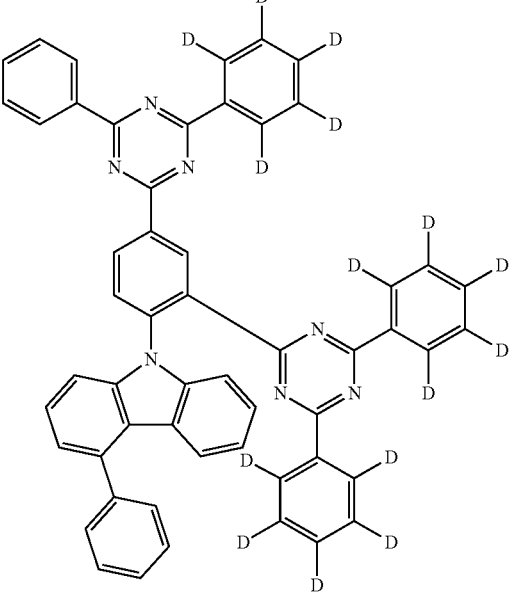
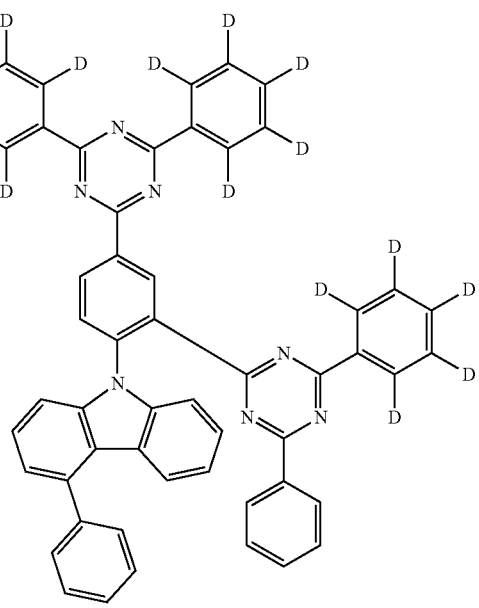

93
-continued
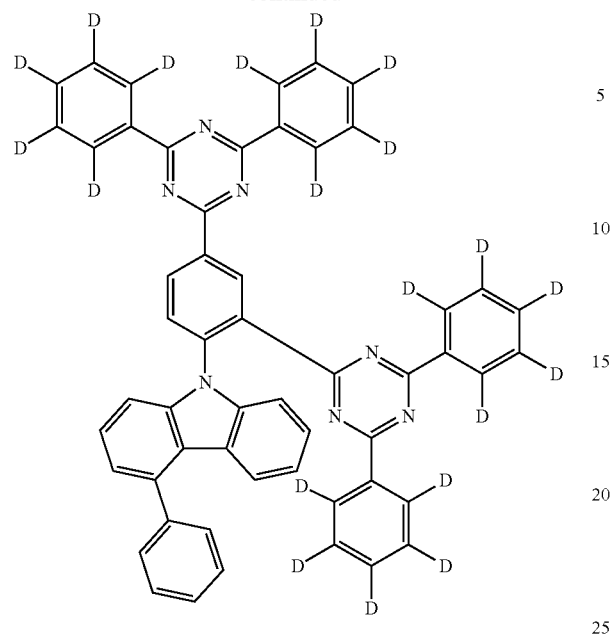
94
-continued
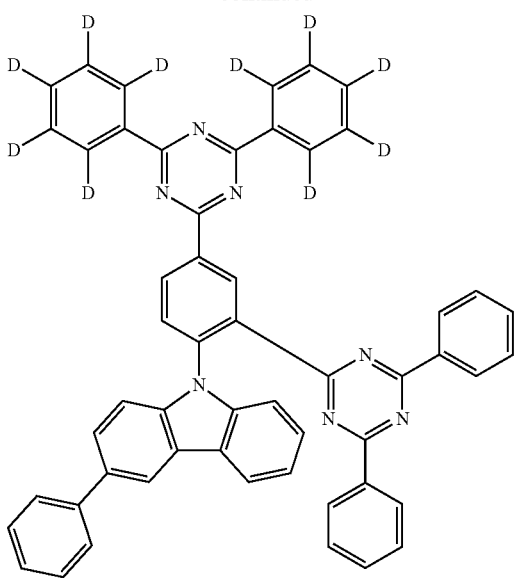
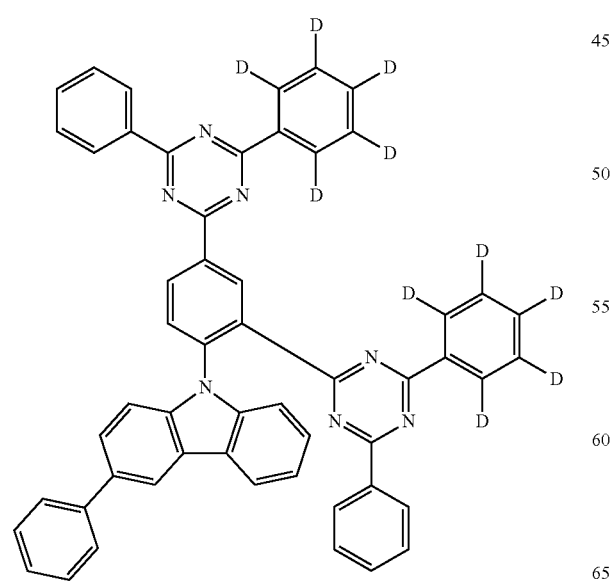

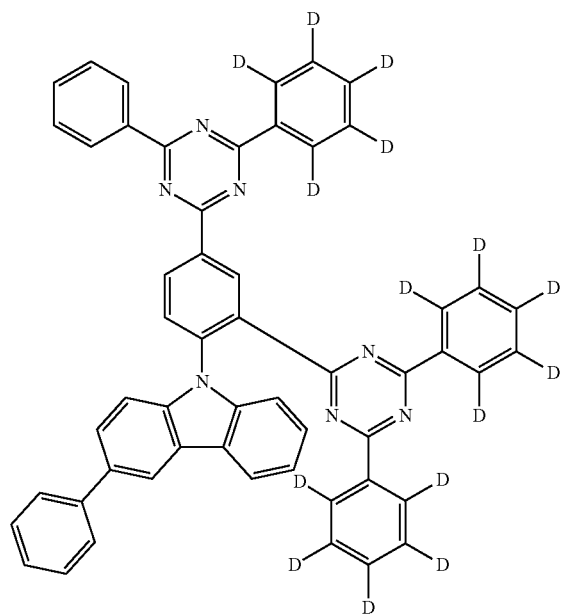
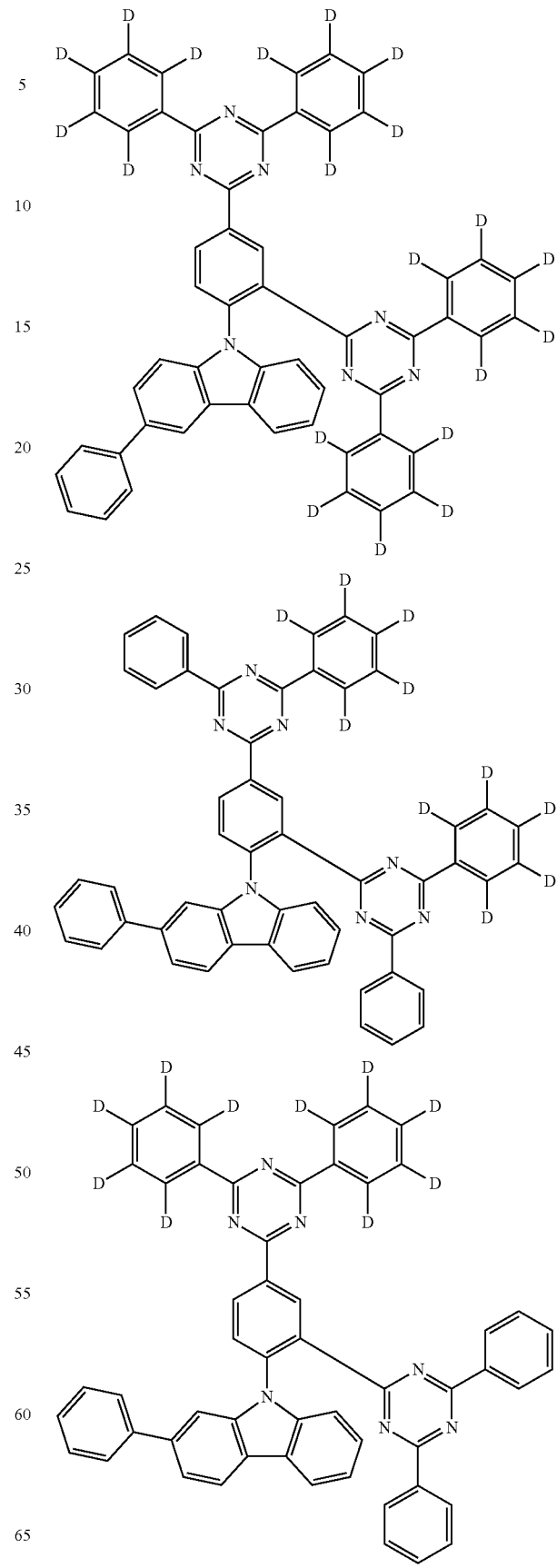

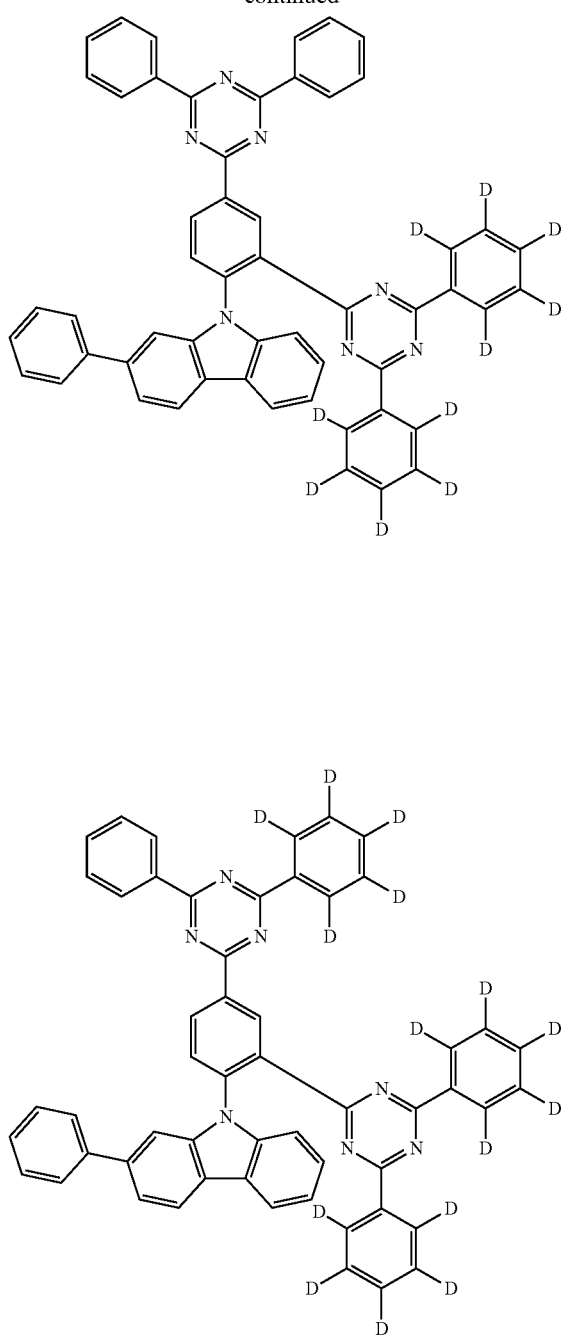
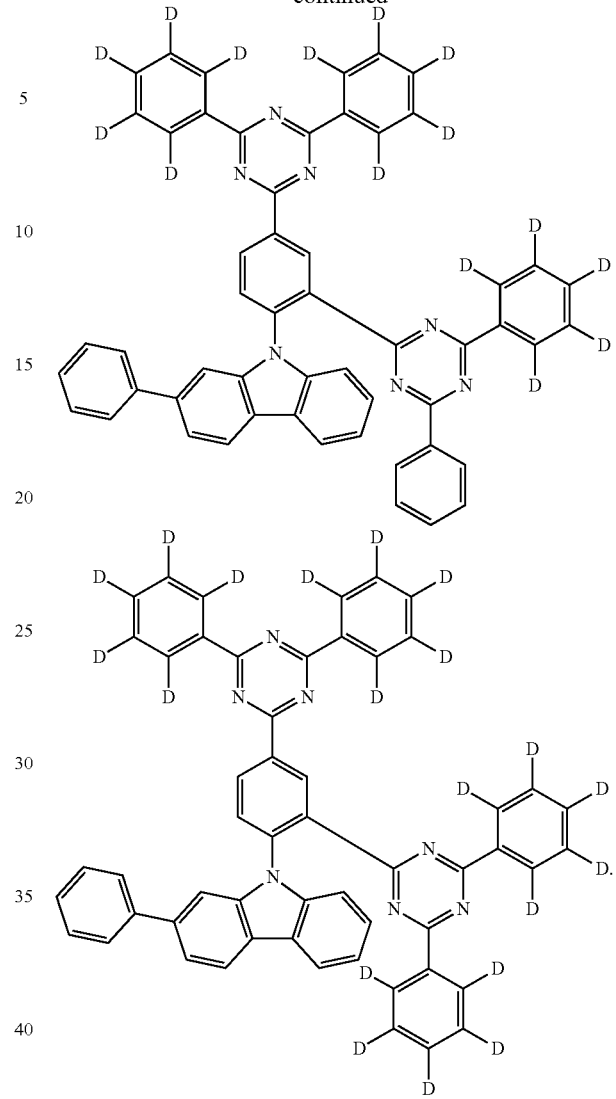
4. An organic light emitting device, comprising:
   a first electrode;
   a second electrode provided opposite to the first electrode; and
   one or more organic material layers provided between the first electrode and the second electrode, wherein one or more layers of the one or more organic material layers include the compound of claim 1.
* * * * *

UNITED STATES PATENT AND TRADEMARK OFFICE
CERTIFICATE OF CORRECTION

PATENT NO. : 12,022,730 B2
APPLICATION NO. : 17/278757
DATED : June 25, 2024
INVENTOR(S) : Jung et al.

It is certified that error appears in the above-identified patent and that said Letters Patent is hereby corrected as shown below:

In the Claims

In Claim 3, at Column 88, the following two compounds should be inserted after the compound at Lines 24-47:

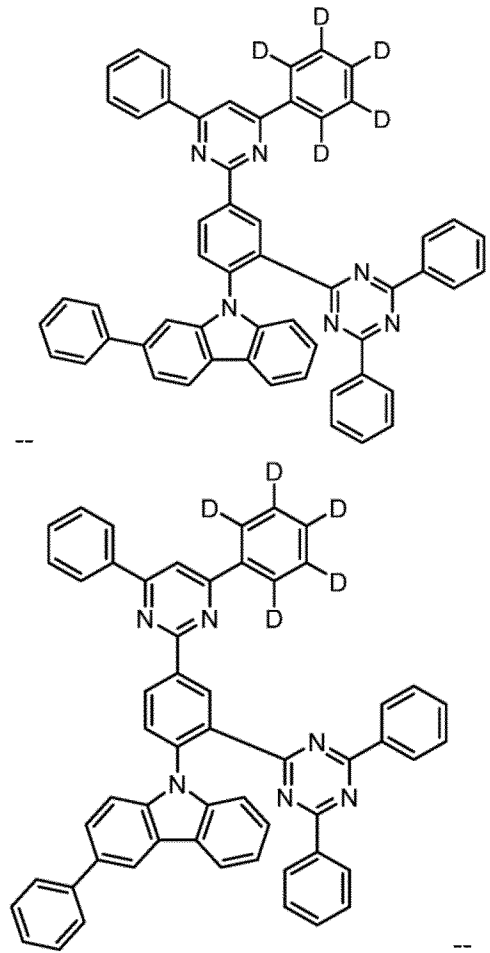

Signed and Sealed this
Thirtieth Day of July, 2024

Katherine Kelly Vidal
Director of the United States Patent and Trademark Office